(12) United States Patent
Alekseyev et al.

(10) Patent No.: US 12,415,996 B2
(45) Date of Patent: *Sep. 16, 2025

(54) SUBTILISIN VARIANTS

(71) Applicant: DANISCO US INC, Palo Alto, CA (US)

(72) Inventors: Viktor Yuryevich Alekseyev, Palo Alto, CA (US); Lilia Maria Babe, Palo Alto, CA (US); H. Billur Engin, Palo Alto, CA (US); David A. Estell, Palo Alto, CA (US); Frits Goedegebuur, Leiden (NL); Thijs Kaper, Palo Alto, CA (US); Harm Mulder, Leiden (NL); Sina Pricelius, Leiden (NL); Sander Van Stigt Thans, Leiden (NL)

(73) Assignee: Danisco US Inc., Palo Alto, CA (US)

( * ) Notice: Subject to any disclaimer, the term of this patent is extended or adjusted under 35 U.S.C. 154(b) by 965 days.

This patent is subject to a terminal disclaimer.

(21) Appl. No.: 17/251,014

(22) PCT Filed: May 24, 2019

(86) PCT No.: PCT/US2019/033873
§ 371 (c)(1),
(2) Date: Dec. 10, 2020

(87) PCT Pub. No.: WO2019/245704
PCT Pub. Date: Dec. 26, 2019

(65) Prior Publication Data
US 2021/0214703 A1  Jul. 15, 2021

Related U.S. Application Data

(60) Provisional application No. 62/686,809, filed on Jun. 19, 2018.

(51) Int. Cl.
C12N 9/56 (2006.01)
C11D 3/386 (2006.01)
C12N 9/54 (2006.01)

(52) U.S. Cl.
CPC ............... C12N 9/54 (2013.01); C11D 3/386 (2013.01); C11D 2111/12 (2024.01); C12Y 304/21062 (2013.01)

(58) Field of Classification Search
CPC ...................................................... C12N 9/54
See application file for complete search history.

(56) References Cited

U.S. PATENT DOCUMENTS 11,499,146 B2 * 11/2022 Babe ............... C12Y 304/21062
2019/0185789 A1 * 6/2019 Souter ..................... C12N 9/54
(Continued)

FOREIGN PATENT DOCUMENTS

WO  WO-2016205755 A1 * 12/2016 ............. A61P 43/00
WO  2017/192692 A1    11/2017
(Continued)

OTHER PUBLICATIONS

Martinez. Increasing activity and thermal resistance of Bacillus gibsonii alkaline protease (BgAP) by directed evolution. Biotechnol. Bioeng., 110: 711-720. (2013).*
(Continued)

Primary Examiner — Yong D Pak

(57) ABSTRACT

Disclosed herein is one or more subtilisin variant, nucleic acid encoding same, and compositions and methods related to the production and use thereof, including one or more subtilisin variant that has improved stability and/or soil removal compared to one or more reference subtilisin.

8 Claims, 1 Drawing Sheet

Specification includes a Sequence Listing.

(56) References Cited

U.S. PATENT DOCUMENTS

| | | | | |
|---|---|---|---|---|
| 2019/0330610 | A1* | 10/2019 | Babe | C12Y 304/21062 |
| 2022/0098524 | A1* | 3/2022 | Souter | C11D 3/38618 |

FOREIGN PATENT DOCUMENTS

| | | | | |
|---|---|---|---|---|
| WO | WO-2018118950 A1 * | 6/2018 | | C11D 3/386 |
| WO | WO-2019125984 A1 * | 6/2019 | | C11D 11/0023 |
| WO | WO-2019125985 A1 * | 6/2019 | | C11D 11/0023 |
| WO | WO-2019125986 A1 * | 6/2019 | | C11D 11/0023 |

OTHER PUBLICATIONS

Fransceus (J Ind Microbiol Biotechnol. May 2017;44(4-5):687-695.*

Sanavia. Computational and Structural Biotechnology Journal, vol. 18, 2020, pp. 1968-1979.*

Studer. Residue mutations and their impact on protein structure and function: detecting beneficial and pathogenic changes. Biochem. J. (2013) 449, 581-594.*

A0A1H9VK28_9BACI. UniProtKB/TrEMBL Database. Nov. 22, 2017.*

Deng, Aihua et al., Secretory Expression, Functional Characterization, and Molecular Genetic Analysis of Novel Halo-Solvent-Tolerant Protease from Bacillus gibsonii, Journal of Microbiology and Biotechnology, Feb. 28, 2014, pp. 197-208, vol. 24, No. 2.

Jakob, Felix et al., Surface charge engineering of a Bacillus gibsonii subtilisin protease, Applied Microbiology and Biotechnology, Nov. 21, 2012, pp. 6793-6802, vol. 97, No. 15.

Martinez, Ronny et al., Increasing Activity and Thermal Resistance of Bacillus gibsonii Alkaline Protease (BgAP) by Directed Evolution, Biotechnology and Bioengineering, Nov. 1, 2012, pp. 711-720, vol. 110, No. 3.

Vojcic, Ljubica et al., Advances in protease engineering for laundry detergents, New Biotechnology, Dec. 1, 2015, pp. 629-634, vol. 32, No. 6.

PCT/US2019/033873—International Search Report and Written Opinion—mailed Sep. 17, 2019.

* cited by examiner

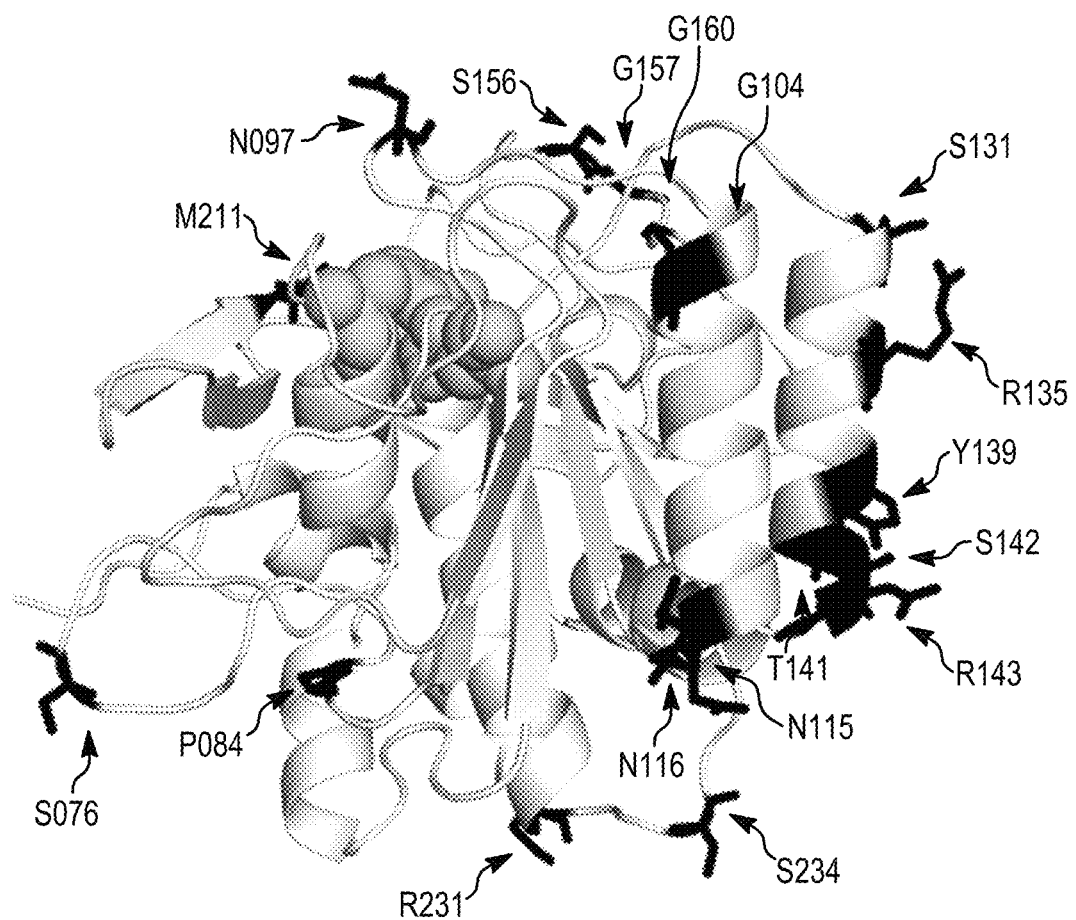

SEQUENCE LISTING

```
<160> NUMBER OF SEQ ID NOS: 10

<210> SEQ ID NO 1
<211> LENGTH: 269
<212> TYPE: PRT
<213> ORGANISM: Bacillus gibsonii

<400> SEQUENCE: 1

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Glu Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95
```

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
            165                 170                 175

Asn Asn Arg Arg Ala Asn Phe Ser Gln Tyr Gly Thr Gly Ile Asp Ile
        180                 185                 190

Val Ala Pro Gly Val Asn Val Gln Ser Thr Tyr Pro Gly Asn Arg Tyr
    195                 200                 205

Val Ser Met Asn Gly Thr Ser Met Ala Thr Pro His Val Ala Gly Ala
210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
            245                 250                 255

Phe Gly Ser Gly Leu Val Asn Ala Glu Ala Ala Thr Arg
        260                 265

<210> SEQ ID NO 2
<211> LENGTH: 1052
<212> TYPE: DNA
<213> ORGANISM: Bacillus subtilis

<400> SEQUENCE: 2
gcaaaacgcg gatcattgga agagacgacc gtacccgcag catcaatgcc taaaataagc      60
ggatactctc tgacgatatt gcctcctgct tttccggcca gaccatcttt gtaattaatg     120
ccggaataag caactttaat caggacacca tccttcggca aatcctctgt tgatatggtt     180
ttcacatgga ctgaaacatc atcggcattt ttttctgcct gcaaggcttg aaataacgtt     240
gacattcggc acactccttt tcatttatat cgtaaccgaa gaacgttcaa aaaccaaat     300
catcaagccg ccattttcac ttcgccggca cattgagaca ataatggaca aatccggtat     360
cctcttcata gccgttttgc tcatacaagc ttcttgcctt ccggttgtgg tgctcagtct     420
gaagtgttaa acattttgcc ccgttttgcc ctgcataatc ctttgcggca gaaagcagcc     480
ggccgccggc tcccttgta cgcgcatgag gaacgacaaa taagtcattt aatatgtata     540
tccttttcat tgacacagaa gaaaacgttg gatagagctg ggtaaagcct atgaattctc     600
cattttcttc tgctatcaaa ataacagact cgtgattttc caaacgagct ttcaaaaaag     660
cctctgcccc ttgcaaatcg gatgcctgtc tataaaattc ccgatattgg ttaaacagcg     720
gcgcaatggc ggccgcatct gatgtctttg cttggcgaat gttcatctta tttcttcctc     780
cctctcaata attttttcat tctatccctt ttctgtaaag tttatttttc agaatacttt     840
tatcatcatg ctttgaaaaa atatcacgat aatatccatt gttctcacgg aagcacacgc     900
gtcgctgata aacagctgac atcaactaaa agcttcatta aatactttga aaaagttgt      960
tgacttaaaa gaagctaaat gttatagtaa taaacagaa tagtcttttta agtaagtcta    1020
ctctgaattt ttttaaaagg agagggtaaa ga                                   1052

<210> SEQ ID NO 3
<211> LENGTH: 87
<212> TYPE: DNA
<213> ORGANISM: Bacillus subtilis

<400> SEQUENCE: 3
gtgagaagca aaaaattgtg gatcagcttg ttgtttgcgt taacgttaat ctttacgatg    60
gcgttcagca acatgtctgc gcaggct                                        87

<210> SEQ ID NO 4
<211> LENGTH: 252
<212> TYPE: DNA
<213> ORGANISM: Bacillus lentus

<400> SEQUENCE: 4
gctgaagaag caaaagaaaa atatttaatt ggctttaatg agcaggaagc tgtcagtgag    60
tttgtagaac aagtagaggc aaatgacgag gtcgccattc tctctgagga agaggaagtc   120
gaaattgaat tgcttcatga atttgaaacg attcctgttt tatccgttga gttaagccca   180
gaagatgtgg acgcgcttga actcgatcca gcgatttctt atattgaaga ggatgcagaa   240
gtaacgacaa tg                                                       252

<210> SEQ ID NO 5
<211> LENGTH: 810
<212> TYPE: DNA
<213> ORGANISM: Bacillus gibsonii

<400> SEQUENCE: 5
caacaaacag tgccatgggg aattactcgt gtgcaagccc cagctgttca taaccgtgga    60
attacaggtt ctggtgtaag agttgctatc ctcgattcag gtatttccgc acatgaagac   120
ttaaatattc gtggtggcgc aagctttgta ccaggggaac aacgactgc tgatttaaat    180 gggcatggca cgcatgtggc tgggacggta gctgctttaa acaattcgat tggcgttatt   240
ggcgtagcac cgaatgcgga actatacgct gttaaagtat taggggcgaa tggtagcggt   300
tcggtcagcg ggattgccca aggattggaa tgggcagcaa caaataacat gcacattgct   360
aatatgagtt taggaagcga ttttccaagt tctacacttg agcgtgctgt taattatgcg   420
acttctagag atgttcttgt tattgcggca actgggaata cggttctgg ctcagtaggc    480 tatccggccc gttatgcgaa cgcaatggca gtcggagcta ctgaccaaaa caacagacgc   540
gccaactttt cacagtatgg cacggggatt gacattgtcg caccaggtgt aaacgtgcag   600
agcacatacc aggtaaccg ttatgtgagc atgaacggta tcgatggc tactcctcat      660 gttgcaggtg cagcagccct tgttaaacaa cgctatccat cttggaatgc gactcaaatc   720
cgcaatcatc taaagaatac ggcaacgaat ttaggaaact cttcacaatt tggaagcgga   780
cttgtcaatg cagaagcggc aacacgctaa                                    810

<210> SEQ ID NO 6
<211> LENGTH: 253
<212> TYPE: DNA
<213> ORGANISM: Bacillus amyloliquefaciens

<400> SEQUENCE: 6
tctagataca taaaaaaccg gccttggccc cgccggtttt ttattatttt tcttcctccg    60
catgttcaat ccgctccata atcgacggat ggctccctct gaaaattta acgagaaacg   120 gcgggttgac ccggctcagt cccgtaacgg ccaagtcctg aaacgtctca atcgccgctt   180

| cccggtttcc | ggtcagctca | atgccgtaac | ggtcggcggc | gttttcctga | taccgggaga | 240 |
| cggcattcgt | aat | | | | | 253 |

<210> SEQ ID NO 7
<211> LENGTH: 855
<212> TYPE: DNA
<213> ORGANISM: Staphylococcus aureus

<400> SEQUENCE: 7

| ttagtgacat | tagaaaaccg | actgtaaaaa | gtacagtcgg | cattatctca | tattataaaa | 60 |
| gccagtcatt | aggcctatct | gacaattcct | gaatagagtt | cataaacaat | cctgcatgat | 120 |
| aaccatcaca | aacagaatga | tgtacctgta | agatagcgg | taaatatatt | gaattacctt | 180 |
| tattaatgaa | ttttcctgct | gtaataatgg | gtagaaggta | attactatta | ttattgatat | 240 |
| ttaagttaaa | cccagtaaat | gaagtccatg | gaataataga | aagagaaaaa | gcattttcag | 300 |
| gtataggtgt | tttgggaaac | aatttccccg | aaccattata | tttctctaca | tcagaaaggt | 360 |
| ataaatcata | aaactctttg | aagtcattct | ttacaggagt | ccaaatacca | gagaatgttt | 420 |
| tagatacacc | atcaaaaatt | gtataaagtg | gctctaactt | atcccaataa | cctaactctc | 480 |
| cgtcgctatt | gtaaccagtt | ctaaaagctg | tatttgagtt | tatcacccctt | gtcactaaga | 540 |
| aaataaatgc | agggtaaaat | ttatatcctt | cttgttttat | gtttcggtat | aaaacactaa | 600 |
| tatcaatttc | tgtggttata | ctaaaagtcg | tttgttggtt | caataatga | ttaaatatct | 660 |
| cttttctctt | ccaattgtct | aaatcaattt | tattaaagtt | catttgatat | gcctcctaaa | 720 |
| ttttatcta | aagtgaattt | aggaggctta | cttgtctgct | ttcttcatta | gaatcaatcc | 780 |
| ttttttaaaa | gtcaatatta | ctgtaacata | aatatatatt | ttaaaaatat | cccactttat | 840 |
| ccaattttcg | tttgt | | | | | 855 |

<210> SEQ ID NO 8
<211> LENGTH: 994
<212> TYPE: DNA
<213> ORGANISM: artificial sequence
<220> FEATURE:
<223> OTHER INFORMATION: synthesized sequence - 3 prime AprE flanking sequence

<400> SEQUENCE: 8

| tcagccttat | tctcctgata | acgcgagaca | gcattagaaa | aaggcgtaac | cgcaaagctc | 60 |
| aaaacagaaa | acaaaagcaa | taacagcgga | agtgccgcaa | gatcatgccg | cccttctaaa | 120 |
| tgaaacatgc | tgcgggttag | gcgaaccgtc | cgcttgtaaa | gcttatcaat | gacataaaat | 180 |
| ccggcgagcg | acacgagcaa | atagccagcc | agaccgatgt | aaacgtgctt | catgacataa | 240 |
| tggcccattt | cgtggcccat | aataaacaga | atttctgaat | cgtcaagttt | gttcagcgtc | 300 |
| gtatcccaca | atacaatccg | tttattggcc | ccaattcctg | taacataggc | attcagcgca | 360 |
| tttgtttttt | ctgacatgtt | cacttcatat | acatggtcag | ccggaatatt | ggcttcatct | 420 |
| gccagctcta | aaattttgct | ttcaagctct | tgttttttca | gcggataaaa | atcattgtat | 480 |
| aaaggatcga | taatgaccgg | ctgaataaaa | aacagaaaca | gcgaaaacgg | cactgttaac | 540 |
| agccaggcgt | ataaccacca | ttttttttca | tgccttttga | tcagccaata | aaaaacgaga | 600 |
| acgcaaagcg | taagattgg | aaagctgatc | caaaagctga | taacctgatc | cttagcccag | 660 |
| ctggccgttg | tctgtgtgga | aatgttatag | tcaagcgata | cttgatagcc | tatccaatct | 720 |
| aaaggcagcg | tcaccaatgt | tgtaatcagc | gaaagcacaa | acacaaaacc | aacggtctgc | 780 |

```
aaaaaccgaa aaggcacggc cgcttcgatc catttcttga ttttctttga aacaccgctg    840
acaagcagaa caaaaaacag aaaccaatca agtggtaccc cgataaaaaa taaaaaattc    900
ttgacattcg aatactgctc ggccactgcc aactcagacg gcttcatgaa agaagccgga    960
tcagcctgcg tccctttcac ggcttccggt attg                                994

<210> SEQ ID NO 9
<211> LENGTH: 29
<212> TYPE: PRT
<213> ORGANISM: Bacillus subtilis

<400> SEQUENCE: 9

Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala
            20                  25

<210> SEQ ID NO 10
<211> LENGTH: 84
<212> TYPE: PRT
<213> ORGANISM: Bacillus lentus

<400> SEQUENCE: 10

Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
            20                  25                  30

Ile Leu Ser Glu Glu Glu Val Glu Ile Glu Leu Leu His Glu Phe
        35                  40                  45

Glu Thr Ile Pro Val Leu Ser Val Glu Leu Ser Pro Glu Asp Val Asp
    50                  55                  60

Ala Leu Glu Leu Asp Pro Ala Ile Ser Tyr Ile Glu Glu Asp Ala Glu
65                  70                  75                  80

Val Thr Thr Met
```

US 12,415,996 B2

SUBTILISIN VARIANTS

This application claims the benefit of U.S. Application No. 62/686,909, filed Jun. 19, 2018, and is herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named 20190523_NB41510PCT_SeqLst_ST25.txt created on May 23. 2019 and having a size of 11 kilobytes and is filed concurrently with the specification. The sequence listing contained in this ASCII formatted document is part of the specification and is herein incorporated by reference in its entirety.

Disclosed herein is one or more subtilisin variant, nucleic acid encoding same, and compositions and methods related to the production and use thereof, including one or more subtilisin variant that has improved stability and/or soil removal compared to one or more reference subtilisin.

BACKGROUND

A protease (also known as a proteinase) is an enzyme that has the ability to break down other proteins. A protease has the ability to conduct proteolysis, which begins protein catabolismby hydrolysis of peptide bonds that link amino acids together in a peptide or polypeptide chain forming the protein. This activity of a protease as a protein-digesting enzyme is termed a proteolytic activity. Many well-known procedures exist for measuring proteolytic activity (Kalisz, "Microbial Proteinases," In: Fiechter (ed.), Advances in Biochemical Engineering/Biotechnology, (1988)). For example, proteolytic activity may be ascertained by comparative assays which analyze the respective protease's ability to hydrolyze an off the shelf protease substrate.

Serine proteases are enzymes (EC No. 3.4.21) possessing an active site serine that initiates hydrolysis of peptide bonds of proteins. Serine proteases comprise a diverse class of enzymes having a wide range of specificities and biological functions that are further divided based on their structure into chymotrypsin-like (trypsin-like) and subtilisin-like. The prototypical subtilisin (EC No. 3.4.21.62) was initially obtained from *Bacillus subtilis*. Subtilisins and their homologues are members of the S8 peptidase family of the MEROPS classification scheme (Rawlings, N. D. et al (2016) Twenty years of the MEROPS database of proteolytic enzymes, their substrates and inhibitors. Nucleic Acids Res 44, D343-D350). Members of family S8 have a catalytic triad in the order Asp, His and Ser in their amino acid sequence. Although a number of useful variant proteases have been developed for cleaning applications, there remains a need for improved protease variants.

SUMMARY

One embodiment is directed to one or more subtilisin variant comprising an amino acid sequence having a glutamate at a position corresponding to position 39 of SEQ ID NO: 1 and further comprising one or more amino acid substitutions selected from: (i) X003V, X004T, X008V, X009A/C/E/G/H/K/M/N/Q/W/Y, X010A/K/M/N/Q/W, X011A/I/S/T, X012A/C/D/G/M/N/R/S/T/V/W, X014D, X015D/E/F/H/I/K/M/P/Q/V/W/Y, X016L/M/S, X017C/E/F/ G/I/L/N/V/W/Y, X018A/C/D/E/F/G/L/M/Q/T, X019A/C/D/ E/F/H/I/K/L/N/Q/S/T/W/Y, X020A/C/D/M/N/T, X024A/E, X025A/C/D/E/M/N, X026A/I, X033T, X036C/E/I/L/M/Q/ T/V, X042C/D/E/M/Q, X043L, X044C/E/F/G/H/I/K/L/N/Q/ T/V/W/Y, X047I/Y, X050I, X052A/C/D/H/L/M/N/S/T/Y, X054A/C/G/L/M/N/T/V, X055A/C/D/E/H/N/S/Y, X057D/ E/H/M/N/Q/T, X059A/C/D/E/M/N/Q/T, X060S, X069S, X076A/D/E/F/H/K/L/M/N/R/T/Y, X082A, X084D/F/H/Y, X095A/N, X096M/Q, X097E/H/K, X101T, X102L/M, X104A/D/H/M/N/T/V/W/Y, X105V, X107K/M, X110L, X113T/V, X114V, X115E/H/Q, X116E/H, X118D/E/N, X120V, X128G, X129A/H/N/Y, X131A/D/E/I/M/N/P/Q/V, X133M, X135A/E/F/H/I/K/L/M/S/T/V/W/Y, X136M, X137L, X139E/S, X141E/H/N, X142A/D/E/H/M/N/Q, X143E/H/M/N/V, X144E/N, X145C, X147C, X148L/V, X1SOM, X156C/D/N/T, X157A/C/D/E/N/Q, X158A/C/F/ L/M/N/Q/V/W/Y, X159L, X160A/C/D/M/T, X161W, X164A/K/M/Q/Y, X166D/E/I/P/Q/V, X167E, X170G, X174V, X176A/C/D/L/M/N/S, X177A/C/D/E/G/H/K/L/M/ Q/S/W/Y, X178D, X179A/C/E/F/G/H/I/K/M/Q/S/V/W/Y, X180K, X182A/C/D/E/G/H/I/K/L/P/Q/T/V/W/Y, X186F, X188C/D/E/I/L/M/N/Q/S/V/W/Y, X189C/D/E, X190M, X191E, X192C/M, X193A/M, X198D/E, X200H/I/K/M/V/ Y, X207K/L/N/Q/T, X209P, X210C/D/E/F/G/L/N/P/Q/Y, X211E/L/Q/R, X212A/C/Q, X218C/S, X227M/Q, X228L, X231C/E/H/I/L/N/Q/S/T, X232F/H/Q/R/W, X234A/D/E/M/ T/W/Y, X236G/S/T, X238A/D/E/M/V, X239D/E/L/M/N/T, X242A, X245E, X246A/L, X247E/Q, X249C/D/E/F/I/L/S/ Y, X250S/T, X253E, X254P/Y, X255A/C/D/E/F/I/M/V/W, X256C/F/H/M/W/Y, X257C/M, X259D/E/M/N, X262L, X263D/Q, X264T, X265A/M/N/Q, X266L/M/N/Q/R, X268A/C/D/E, and X269H/P/W; (ii) X008V, X011S, X012A/C/D/G/M/N/S/T/V, X014D, X016M, X017C/I/N/W, X018T, X019A/D/F/H/I/L/Q/S/W/Y, X024A/E, X025M/N, X042D/E/M, X044E/G/I/N/T, X052T, X054T/V, X055E, X059D/E, X060S, X069S, X096Q, X115E, X128G, X129H, X131D, X135E/F/H/I/S/T/V, X137L, X139E/S, X141E/H/ N, X143E/H/M/N/V, X156C, X157D/E, X158C/V, X161W, X164M/Q/Y, X166V, X167E, X176D/M/N/S, X177C/E, X1791/S/V/W, X182D/E/P/Q/T, X188D/E/S/V, X190M, X193M, X198D, X207K/N/T, X210D/E, X211E/Q, X2311/ S, X234D, X238D, X249D, X250T, and X269H; (iii) X003V, X009Q/W, X012R/W, X015M/Q, X016M, X024A, X042M, X054N, X057M/Q, X059N, X076R, X104A, X131A/M/P/Q, X142N/Q, X144E, X145C, X147C, X157A/ Q, X158A/N/Q, X160A, X166Q, X176A, X177Q, X186F, X190M, X211Q, X212A, X227Q, X232F/Q/R, X234A, X238A, X256M, X257M, X259M, X265M/N/Q, and X266Q/R; (iv) X009H/K/N/W, X011A/I, X012A/M/N/R/S/ V, X015F/I/K/V, X016L/M, X017F/G/I/L/N/V/W, X018F, X019C/K/L/Q. X020A/D/M/N/T, X024A, X025A/D/N, X036L, X052D/H, X054A/G/L/M/V, X055A/D/H/S/Y, X059A/M/N, X060S, X069S, X076K/L, X095N, X096Q, X097K, X102L/M, X107K, X110L, X113T, X118D, X120V, X128G, X129A/H/N/Y, X131M/N/P, X136M, X143N, X144N, X145C, X157A/D, X158Q, X159L, X160D/M, X166I, X170G, X176L, X177A/D/G/K/L/M/S/ Y, X179A/K, X182A/D/Y, X188M, X191E, X207L, X210E/ G/Q, X211E/Q/R, X218S, X227M, X232F/W, X256Y, X263Q, X265A/M/Q, and X268A; (v) X009A/C/E/M/N/Y, X010A/K/M/N/Q/W, X011A/T, X012A/C/D/M, X014D, X015D/E/H/I/M/V/W/Y, X016L/M, X017C/E, X018C/D/E/ M, X019A/C/D/E/F/H/I/K/L/N/Q/S/T/W/Y, X020C/D, X024A/E, X025A/C/D/E/M/N, X026A, X036C/E/Q/V, X042C/D/E, X043L, X044C/E/G/H/I/L/N/Q/T, X052A/C/ D/L/M/N, X054A/C/L/M/V, X055A/C/D/E, X057D/E, X059A/C/D/E/M/N/Q/T, X060S, X076D/E/N, X082A, X084D, X096Q, X097E/H, X104A/D/H/N/V/Y, X115H, X116E, X128G, X129H, X131D/E, X135A/E/F/H/I/K/L/M/S/T/V/W/Y, X139E, X141E, X142D/E, X143E, X144E, X147C, X148L, X156C/D/N/T, X157C/D/E, X158C/L/Q/Y, X159L, X164A/K/M/Q/Y, X166D/E, X167E, X174V, X176A/C/D/N, X177C/D/E, X178D, X179A/C/E/F/G/H/I/J/K/M/Q/S/V/W/Y, X180K, X182C/D/E, X188C/D/E, X189C/D/E, X193A/M, X198D/E, X207K/L/N/Q/T, X209P, X210C/D/E/L/N/Y, X211E/L/Q, X212C/Q, X228L, X231C/E/L/N/Q, X232F, X234D/E/T/W/Y, X236T, X238A/D/E/M/V, X239D/E/M/N, X245E, X246A/L, X247E/Q, X249C/D/E/L/Y, X253E, X254Y, X255A/C/D/E, X256C/Y, X257C, X259D/E/M/N, X262L, X263D, X268C/D/E, and X269H/P/W; (vi) X009N, X011A, X012A/M, X015I/V, X016L/M, X019C/K/L/Q, X020D, X024A, X025A/D/N, X052D, X054A/L/M/V, X055A/D, X059A/M/N, X060S, X096Q, X128G, X129H, X157D, X158Q, X159L, X177D, X179A/K, X182D, X207L, X210E, X211E/Q, X232F, and X256Y; (vii) X003V, X004T, X008V, X009A/E/G/H/K/N/Q/W/Y, X010Q, X011A, X012A/C/G/M/N/T, X015F/H/M/P/Q/W, X016S, X017C/E/F/I/L/N/V/W/Y, X018A/D/E/L/M/Q, X019C/D/Y, X020C/D/M/N, X024A/E, X025C/D/N, X026I, X033T, X036C/I/L/M/Q/V, X042C/D/E/M/Q, X044C/E/F/G/H/I/K/L/N/Q/T/V/W/Y, X0471/Y, X0501, X052A/M/N/S/T/Y, X054N/V, X055C/D/E/N, X057E/H/M/N/Q/T, X059N, X076A/D/E/F/H/K/L/M/N/R/T/Y, X082A, X084D/F/H/Y, X095A/N, X096M, X097K, X101T, X102L/M, X104M/N/T/V/W, X105V, X107M, X113V, X114V, X115Q, X116E/H, X118D/E/N, X131A/D/E/I/M/N/P/Q/V, X133M, X135A/H/I/K/L/M/S/T/V/W/Y, X136M, X142A/D/E/H/M/N/Q, X143E/H/M/N, X147C, X148V, X150M, X156N/T, X157A/C/N, X158C/F/L/M/N/Q/V/W/Y, X159L, X160A/C/M/T, X166D/E/P/Q, X170G, X176C/M, X177A/C/D/H/L/M/Q/W/Y, X179M/Q, X180K, X182A/C/B/G/H/I/K/L/P/Q/T/V/W/Y, X188C/D/E/I/L/M/N/Q/V/W/Y, X189D, X192C/M, X193M, X200H/I/K/M/V/Y, X209P, X210E/F/P, X218C/S, X228L, X231C/E/H/N/T, X232F/H, X234D/M, X236G/S/T, X238A/D/E/M/V, X239E/L/M/T, X242A, X246A/L, X249E/F/I/L/S/Y, X250S, X253E, X254P, X255C/D/E/F/I/M/V/W, X256C/F/H/W/Y, X264T, X266L/M/N, and X268C; (viii) X009A/E/H/K/N/W/Y, X010Q, X011A, X012A/C/M/N, X015F/H/M/W, X017C/E/F/I/L/N/V/W, X018D/E/M, X019C/D/Y, X020C/D/M/N, X024A/E, X025C/D/N, X036C/L/Q/V, X042C/D/E, X044C/E/G/H/I/L/N/Q/T, X052A/M/N, X054V, X055C/D/E, X057E, X059N. X076D/E/K/L/N, X082A, X084D, X095N, X097K, X102L/M, X104N/V, X116E, X118D, X131D/E/M/N/P, X135A/H/I/K/L/M/S/T/V/W/Y, X136M, X142D/E, X143E/N, X147C, X156N/T, X157A/C, X158C/L/Q/Y, X159L, X160M, X166D/E, X170G, X176C, X177A/C/D/L/M/Y, X179M/Q, X180K, X182A/C/E/Y, X188C/D/E/M, X189D, X193M. X209P, X210E, X218S, X228L, X231C/E/N, X232F, X234D, X236T, X238A/D/E/M/V, X239E/M, X246A/L, X249E/L/Y, X253E, X255C/D/E, X256C/Y, and X268C; (ix) X003V, X008V, X009Q/W, X012A/C/G/M/N/T, X015M/Q, X017C/I/N/W, X019D/Y, X024A/E, X025N, X042D/E/M, X044E/G/I/N/T, X052T, X054N/V, X05SE, X057M/Q, X059N, X076R, X131A/D/M/P/Q, X135H/I/S/T/V, X142N/Q, X143E/H/M/N, X147C, X157A, X158C/N/Q/V, X160A, X166Q, X176M, X177C/Q, X182E/P/Q/T, X188D/E/V, X193M, X210E, X232F, X234D, and X238A/D; (x) X009C/E/Y, X010A/K/M/N/Q/W, X012C/D, X014D, X015D/E/Y, X017C/E, X018C/D/E, X019A/C/D/E/F/H/I/K/L/N/Q/S/T/W/Y, X020C/D, X024E, X025C/D/E, X036C/E, X042C/D/E, X044C/E/G/H/I/L/N/Q/T, X052C/D, X054C, X055C/D/E, X057D/E, X059C/D/E, X076D/E, X084D, X097E, X104D/Y, X116E, X131D/E, X135A/E/F/H/I/K/L/M/S/T/V/W/Y, X139E, X141E, X142D/E, X143E, X147C, X156C/D, X157C/D/E, X158C/Y, X164A/K/M/Q/Y, X166D/E, X167E, X176C/D, X177C/D/E, X178D, X179A/C/E/F/G/H/I/K/M/Q/S/V/W/Y, X180K, X182C/D/E, X188C/D/E, X189C/D/E, X198D/E, X207K/L/N/Q/T, X210C/D/E/Y, X211E, X212C, X231C/E/L/N/Q, X234D/E/Y, X238D/E, X239D/E, X245E, X247E, X249C/D/E/Y, X253E, X254Y, X255C/D/E, X256C/Y, X257C, X259D/E, X263D, X268C/D/E, and X269H/P/W; (xi) X012C/D, X014D, X017C/I/N/W, X019A/D/F/H/I/L/Q/S/W/Y, X024E, X042D/E, X044E/G/I/N/T, X055E, X059D/E, X115E, X131D, X135E/F/H/I/S/T/V, X139E, X141E, X143E/H/M/N/V, X156C, X157D/E, X158C, X164M/Q/Y, X167B, X176D, X177C/E, X1791/S/V/W, X182D/E, X188D/E, X198D, X207K/N/T, X210D/E, X211E, X231I/S, X234D, X238D, X249D, and X269H; and (xii) X012R, X076R, X186F, X232F/Q/R, X265M/N/Q, and X266R, where the amino acid positions of the variant are numbered by correspondence with the amino acid sequence of SEQ ID NO: 1.

Other embodiments are directed to methods of cleaning, comprising contacting a surface or an item in need of cleaning with an effective amount of one or more subtilisin variant comprising an amino acid sequence having a glutamate at a position corresponding to position 39 of SEQ ID NO: 1 and further comprising one or more amino acid substitutions selected from, (i) X003V, X004T, X008V, X009A/C/E/G/H/K/M/N/Q/W/Y, X010A/K/M/N/Q/W, X011A/I/S/T, X012A/C/D/G/M/N/R/S/T/V/W, X014D, X015D/E/F/H/I/K/M/P/Q/V/W/Y, X016L/M/S, X017C/E/F/G/I/L/N/V/W/Y, X018A/C/D/E/F/G/L/M/Q/T, X019A/C/D/E/F/H/I/K/L/N/Q/S/T/W/Y, X020A/C/D/M/N/T, X024A/E, X025A/C/D/E/M/N, X026A/I, X033T, X036C/E/I/L/M/Q/T/V, X042C/D/E/M/Q, X043L, X044C/E/F/G/H/I/K/L/N/Q/T/V/W/Y, X047I/Y, X050I, X052A/C/D/H/L/M/N/S/T/Y, X054A/C/G/L/M/N/T/V, X055A/C/D/E/H/N/S/Y, X057D/E/H/M/N/Q/T, X059A/C/D/E/M/N/Q/T, X060S, X069S, X076A/D/E/F/H/K/L/M/N/R/T/Y, X082A, X084D/F/H/Y, X095A/N, X096M/Q, X097E/H/K, X101T, X102L/M, X104A/D/H/M/N/T/V/W/Y, X105V, X107K/M, X110L, X113T/V, X114V, X11SE/H/Q, X116E/H, X118D/E/N, X120V, X128G, X129A/H/N/Y, X131A/D/E/I/M/N/P/Q/V, X133M, X135A/E/F/H/I/K/L/M/S/T/V/W/Y, X136M, X137L, X139E/S, X141E/H/N, X142A/D/E/H/M/N/Q, X143E/H/M/N/V, X144E/N, X145C, X147C, X148L/V, X150M, X156C/D/N/T, X157A/C/D/E/N/Q, X158A/C/F/L/M/N/Q/V/W/Y, X159L, X160A/C/D/M/T, X161W, X164A/K/M/Q/Y, X166D/E/I/P/Q/V, X167E, X170G, X174V, X176A/C/D/L/M/N/S, X177A/C/D/E/G/H/K/L/M/Q/S/W/Y, X178D, X179A/C/E/F/G/H/I/K/M/Q/S/V/W/Y,X180K, X182A/C/D/E/G/H/I/K/L/P/Q/T/V/W/Y, X186F. X188C/D/E/I/L/M/N/Q/S/V/W/Y, X189C/D/E, X190M, X191E, X192C/M, X193A/M, X198D/E, X200H/I/K/M/V/Y, X207K/L/N/Q/T, X209P, X210C/D/E/F/G/L/N/P/Q/Y, X211E/L/Q/R, X212A/C/Q, X218C/S, X227M/Q, X228L, X231C/E/H/I/L/N/Q/S/T, X232F/H/Q/R/W, X234A/D/E/M/T/W/Y, X236G/S/T, X238A/D/E/M/V, X239D/E/L/M/N/T, X242A, X245E, X246A/L, X247E/Q, X249C/D/E/F/I/L/S/Y, X250S/T, X253E, X254P/Y, X255A/C/D/E/F/I/M/V/W, X256C/F/H/M/W/Y, X257C/M, X259D/E/M/N, X262L, X263D/Q, X264T, X265A/M/N/Q, X266L/M/N/Q/R, X268A/C/D/E, and X269H/P/W; (ii) X008V, X011S, X012A/C/D/G/M/N/S/T/V, X014D, X016M, X017C/I/N/W, X018T, X019A/D/F/H/I/L/Q/S/W/Y, X024A/E, X025M/N, X042D/E/M, X044E/G/I/N/T, X052T, X054T/V, X05SE, X059D/E, X060S, X069S, X096Q, X115E, X128G, X129H, X131D, X135E/F/H/I/S/T/V, X137L, X139E/S, X141E/H/

N, X143E/H/M/N/V, X156C, X157D/E, X158C/V, X161W, X164M/Q/Y, X166V, X167E, X176D/M/N/S, X177C/E, X179I/S/V/W, X182D/E/P/Q/T, X188D/E/S/V, X190M, X193M, X198D, X207K/N/T, X210D/E, X211E/Q, X231I/S, X234D, X238D, X249D, X250T, and X269H; (iii) X003V, X009Q/W, X012R/W, X015M/Q, X016M, X024A, X042M, X054N, X057M/Q, X059N, X076R, X104A, X131A/M/P/Q, X142N/Q, X144E, X145C, X147C, X157A/Q, X158A/N/Q, X160A, X166Q, X176A, X177Q, X186F, X190M, X211Q, X212A, X227Q, X232F/Q/R, X234A, X238A, X256M, X257M, X259M, X265M/N/Q, and X266Q/R; (iv) X009H/K/N/W, X011A/I, X012A/M/N/R/S/V, X015F/I/K/V, X016L/M, X017F/G/I/L/N/V/W, X018F, X019C/K/L/Q, X020A/D/M/N/T, X024A, X025A/D/N, X036L, X052D/H, X054A/G/L/M/V, X055A/D/H/S/Y, X059A/M/N, X060S, X069S, X076K/L, X095N, X096Q, X097K, X102L/M, X107K, X110L, X113T, X118D, X120V, X128G, X129A/H/N/Y, X131M/N/P, X136M, X143N, X144N, X145C, X157A/D, X158Q, X159L, X160D/M, X166I, X170G, X176L, X177A/D/G/K/L/M/S/Y, X179A/K, X182A/D/Y, X188M, X191E, X207L, X210E/G/Q, X211E/Q/R, X218S, X227M, X232F/W, X256Y, X263Q, X265A/M/Q, and X268A; (v) X009A/C/E/M/N/Y, X010A/K/M/N/Q/W, X011A/T, X012A/C/D/M, X014D, X01SD/E/H/I/M/V/W/Y, X016L/M, X017C/E, X018C/D/E/M, X019A/C/D/E/F/H/I/K/L/N/Q/S/T/W/Y, X020C/D, X024A/E, X025A/C/D/E/M/N, X026A, X036C/E/Q/V, X042C/D/E, X043L, X044C/E/G/H/I/L/N/Q/T, X052A/C/D/L/M/N, X054A/C/L/M/V, X055A/C/D/E, X057D/E, X059A/C/D/E/M/N/Q/T, X060S, X076D/E/N, X082A, X084D, X096Q, X097E/H, X104A/D/H/N/V/Y, X115H, X116E, X128G, X129H, X131D/E, X135A/E/F/H/I/K/L/M/S/T/V/W/Y, X139E, X141E, X142D/E, X143E, X144E, X147C, X148L, X156C/D/N/T, X157C/D/E, X158C/L/Q/Y, X159L, X164A/K/M/Q/Y, X166D/E, X167E, X174V, X176A/C/D/N, X177C/D/E, X178D, X179A/C/E/F/G/H/I/K/M/Q/S/V/W/Y, X180K, X182C/D/E, X188C/D/E, X189C/D/E, X193A/M, X198D/E, X207K/L/N/Q/T, X209P, X210C/D/E/L/N/Y, X211E/L/Q, X212C/Q, X228L, X231C/E/L/N/Q, X232F, X234D/E/T/W/Y, X236T, X238A/D/E/M/V, X239D/E/M/N, X245E, X246A/L, X247E/Q, X249C/D/E/L/Y, X253E, X254Y, X255A/C/D/E, X256C/Y, X257C, X259D/E/M/N, X262L, X263D, X268C/D/E, and X269H/P/W; (vi) X009N, X011A, X012A/M, X015I/V, X016L/M, X019C/K/L/Q, X020D, X024A, X025A/D/N, X052D, X054A/L/M/V, X055A/D, X059A/M/N, X060S, X096Q, X128G, X129H, X157D, X158Q, X159L, X177D, X179A/K, X182D, X207L, X210E, X211E/Q. X232F, and X256Y; (vii) X003V, X004T, X008V, X009A/E/G/H/K/N/Q/W/Y, X010Q, X011A, X012A/C/G/M/N/T, X015F/H/M/P/Q/W, X016S, X017C/E/F/I/L/N/V/W/Y, X018A/D/E/L/M/Q, X019C/D/Y, X020C/D/M/N, X024A/E, X025C/D/N, X026I, X033T, X036C/I/L/M/Q/V, X042C/D/E/M/Q, X044C/E/F/G/H/I/K/L/N/Q/T/V/W/Y, X047I/Y, X050I, X052A/M/N/S/T/Y, X054N/V, X055C/D/E/N, X057E/H/M/N/Q/T, X059N, X076A/D/E/F/H/K/L/M/N/R/T/Y, X082A, X084D/F/H/Y, X095A/N, X096M, X097K, X101T, X102L/M, X104M/N/T/V/W, X105V, X107M, X113V, X114V, X115Q, X116E/H, X118D/E/N, X131A/D/E/I/M/N/P/Q/V, X133M, X135A/H/I/K/L/M/S/T/V/W/Y, X136M, X142A/D/E/H/M/N/Q, X143E/H/M/N, X147C, X148V, X150M, X156N/T, X157A/C/N, X158C/F/L/M/N/Q/V/W/Y, X159L, X160A/C/M/T, X166D/E/P/Q, X170G, X176C/M, X177A/C/D/H/L/M/Q/W/Y, X179M/Q, X180K, X182A/C/E/G/H/I/K/L/P/Q/T/V/W/Y, X188C/D/E/I/L/M/N/Q/V/W/Y, X189D, X192C/M, X193M, X200H/I/K/M/V/Y, X209P, X210E/F/P, X218C/S, X228L, X231C/E/H/N/T, X232F/H, X234D/M, X236G/S/T, X238A/D/E/M/V, X239E/L/M/T, X242A, X246A/L, X249E/F/I/L/S/Y, X250S, X253E, X254P, X255C/D/E/F/I/M/V/W, X256C/F/H/W/Y, X264T, X266L/M/N, and X268C; (viii) X009A/E/H/K/N/W/Y, X010Q X011A, X012A/C/M/N, X015F/H/M/W, X017C/E/F/I/L/N/V/W, X018D/E/M, X019C/D/Y, X020C/D/M/N, X024A/E, X025C/D/N, X036C/L/Q/V, X042C/D/E, X044C/E/G/H/I/L/N/Q/T, X052A/M/N, X054V, X055C/D/E, X057E, X059N, X076D/E/K/L/N, X082A, X084D, X095N, X097K, X102L/M, X104N/V, X116E, X118D, X131D/E/M/N/P, X135A/H/I/K/L/M/S/T/V/W/Y, X136M, X142D/E, X143E/N, X147C, X156N/T, X157A/C, X158C/L/Q/Y, X159L, X160M, X166D/E, X170G, X176C, X177A/C/D/L/M/Y, X179M/Q, X180K, X182A/C/E/Y, X188C/D/E/M, X189D, X193M, X209P, X210E, X218S, X228L, X231C/E/N, X232F, X234D, X236T, X238A/D/E/M/V, X239E/M, X246A/L, X249E/L/Y, X253E, X255C/D/E, X256C/Y, and X268C; (ix) X003V, X008V, X009Q/W, X012A/C/G/M/N/T, X015M/Q, X017C/I/N/W, X019D/Y, X024A/E, X025N, X042D/E/M, X044E/G/I/N/T, X052T, X054N/V, X055E, X057M/Q, X059N, X076R, X131A/D/M/P/Q, X135H/I/S/T/V, X142N/Q, X143E/H/M/N, X147C, X157A, X158C/N/Q/V, X160A, X166Q, X176M, X177C/Q, X182E/P/Q/T, X188D/E/V, X193M, X210E, X232F, X234D, and X238A/D; (x) X009C/E/Y, X010A/K/M/N/Q/W, X012C/D, X014D, X015D/E/Y, X017C/E, X018C/D/E, X019A/C/D/E/F/H/I/K/L/N/Q/S/T/W/Y, X020C/D, X024E, X025C/D/E, X036C/E, X042C/D/E, X044C/E/G/H/I/L/N/Q/T, X052C/D, X054C, X055C/D/E, X057D/E, X059C/D/E, X076D/E, X084D, X097E, X104D/Y, X116E, X131D/E, X135A/E/F/H/I/K/L/M/S/T/V/W/Y, X139E, X141E, X142D/E, X143E, X147C, X156C/D, X157C/D/E, X158C/Y, X164A/K/M/Q/Y, X166D/E, X167E, X176C/D, X177C/D/E, X178D, X179A/C/E/F/G/H/I/K/M/Q/S/V/W/Y, X180K, X182C/D/B, X188C/D/E, X189C/D/E, X198D/E, X207K/L/N/Q/T, X210C/D/E/Y, X211E, X212C, X231C/E/L/N/Q, X234D/E/Y, X238D/E, X239D/E, X245E, X247E, X249C/D/E/Y, X253E, X254Y, X255C/D/E, X256C/Y, X257C, X259D/E, X263D, X268C/D/E, and X269H/P/W; (xi) X012C/D, X014D, X017C/I/N/W, X019A/D/F/H/I/L/Q/S/W/Y, X024E, X042D/E, X044E/G/I/N/T, X055E, X059D/E, X115E, X131D, X135E/F/H/I/S/T/V, X139E, X141E, X143E/H/M/N/V, X156C, X157D/E, X158C, X164M/Q/Y, X167E, X176D, X177C/E, X179I/S/V/W. X182D/E, X188D/E, X198D, X207K/N/T, X210D/E, X211E, X231I/S, X234D, X238D, X249D, and X269H; and (xii) X012R, X076R, X186F, X232F/Q/R, X265M/N/Q, and X266R, where the amino acid positions of the variant are numbered by correspondence with the amino acid sequence of SEQ ID NO: 1 or a composition comprising such a variant; and optionally further comprising the step of rinsing said surface or item after contacting said surface or item with said variant or composition.

Still other embodiments are directed to a method for producing a variant described herein, comprising stably transforming a host cell with an expression vector comprising a polynucleotide encoding one or more subtilisin variant described herein. Still further embodiments are directed to a polynucleotide comprising a nucleic acid sequence encoding one or more subtilisin variant described herein.

DESCRIPTION OF THE FIGURES

FIG. 1 depicts the location of one embodiment of a subset of beneficial sites listed in Table 4 on the structure of subtilisin BSP-00801 from *B. gibsonii* (described in WO2016205755). The main chain fold of *B. gibsonii* subtilisin BSP-00801 is schematically represented in light gray, the catalytic triad is shown as gray spheres and a subset of the aforementioned sites where beneficial substitutions can be made (numbered with respect to SEQ ID NO: 1) are shown as black stick figures. These sites are surface exposed and suitable for modifications altering enzyme surface properties such as charge.

DESCRIPTION

In one embodiment, the present disclosure provides one or more subtilisin variant comprising an amino acid sequence having a glutamate at a position corresponding to position 39 of SEQ ID NO: 1 and further comprising one or more additional amino acid substitutions. The subtilisin variants provided herein demonstrate one or more improved properties, such as an improved cleaning performance, or improved stability, or both an improved cleaning performance and an improved stability when compared to a subtilisin having the amino acid sequence of SEQ ID NO: 1. The subtilisin variants provided herein find use in the preparation of cleaning compositions (e.g. laundry (HDL or HDD) compositions or automatic dishwashing compositions). In addition, the subtilisin variants provided herein also find use in methods of cleaning (e.g. laundry or dish washing methods) using such variants or compositions comprising such subtilisin variants.

Unless otherwise indicated herein, one or more subtilisin variant described herein can be made and used by a variety of techniques used in molecular biology, microbiology, protein purification, protein engineering, protein and DNA sequencing, recombinant DNA fields, and industrial enzyme use and development. Terms and abbreviations not defined should be accorded their ordinary meaning as used in the art. Unless defined otherwise herein, all technical and scientific terms used herein have the same meaning as commonly understood by one of ordinary skill in the art. Any definitions provided herein are to be interpreted in the context of the specification as a whole. As used herein, the singular "a," "an" and "the" includes the plural unless the context clearly indicates otherwise. Unless otherwise indicated, nucleic acid sequences are written left to right in 5' to 3' orientation; and amino acid sequences are written left to right in amino to carboxy orientation. Each numerical range used herein includes every narrower numerical range that falls within such broader numerical range, as if such narrower numerical ranges were all expressly written herein.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

The nomenclature of the amino acid substitutions of the one or more subtilisin variants described herein uses one or more of the following: position; position: amino acid substitution(s); or starting amino acid(s): position: amino acid substitution(s). Reference to a "position" (e.g. 5, 8, 17, 22, etc) encompasses any starting amino acid that may be present at such position, and any substitution that may be present at such position. Reference to a "position: amino acid substitution(s)" (e.g. 1S/T/G, 3G, 17T, etc) encompasses any starting amino acid that may be present at such position and the one or more amino acid(s) with which such starting amino acid may be substituted. Reference to a position can be recited in several forms, for example, position 003 can also be referred to as position 03 or 3.

Reference to a starting or substituted amino acid may be further expressed as several starting, or substituted amino acids separated by a foreslash ("/"). For example, D275S/K indicates position 275 is substituted with serine(S) or lysine (K) and P/S197K indicates that starting amino acid proline (P) or serine(S) at position 197 is substituted with lysine (K). Reference to an X as the amino acid in a position, refers to any amino acid at the recited position.

The position of an amino acid residue in a given amino acid sequence is numbered by correspondence with the amino acid sequence of SEQ ID NO: 1. That is, the amino acid sequence of SEQ ID NO: 1 serves as a reference sequence. For example, the amino acid sequence of one or more subtilisin variant described herein is aligned with the amino acid sequence of SEQ ID NO: 1 using an alignment algorithm as described herein, and each amino acid residue in the given amino acid sequence that aligns (preferably optimally aligns) with an amino acid residue in SEQ ID NO: 1 is conveniently numbered by reference to the numerical position of that corresponding amino acid residue. Sequence alignment algorithms, such as, for example, described herein will identify the location or locations where insertions or deletions occur in a subject sequence when compared to a query sequence (also sometimes referred to as a "reference sequence"). Sequence alignment with other subtilisin amino acid sequences can be determined using an amino acid alignment, for example, as provided in FIG. 1 of PCT Application No. PCT/US2018/062768, filed Nov. 28, 2018, claiming priority to U.S. Provisional Application No. 62/591,976, filed Nov. 29, 2017, entitled "Highly Stable Subtilisin Enzymes".

The terms "protease" and "proteinase" refer to an enzyme that has the ability to break down proteins and peptides. A protease has the ability to conduct "proteolysis," by hydrolysis of peptide bonds that link amino acids together in a peptide or polypeptide chain forming the protein. This activity of a protease as a protein-digesting enzyme is referred to as "proteolytic activity." Many well-known procedures exist for measuring proteolytic activity. For example, proteolytic activity may be ascertained by comparative assays that analyze the respective protease's ability to hydrolyze a suitable substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and Keratin Azure (Sigma-Aldrich K8500). Colorimetric assays utilizing these substrates are well known in the art (See e.g., WO99/34011 and U.S. Pat. No. 6,376,450). The pNA peptidyl assay (See e.g., Del Mar et al., Anal Biochem, 99:316-320, 1979) also finds use in determining the active enzyme concentration. This assay measures the rate at which p-nitroaniline is released as the enzyme hydrolyzes a soluble synthetic substrate, such as succinyl-alanine-alanine-proline-phenylalanine-p-nitroanilide (suc-AAPF-pNA). The rate of production of yellow color from the hydrolysis reaction is measured at 405 or 410 nm on a spectrophotometer and is proportional to the active enzyme concentration. In addition, absorbance measurements at 280 nanometers (nm) can be used to determine the total protein concentration in a sample of purified protein. The activity on substrate divided by protein concentration gives the enzyme specific activity.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megate-*

*rium, B. coagulans, B. circulans, B. gibsonii*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*", or *B. polymyxa*, which is now "*Paenibacillus polymyxa*". The production of resistant endospores under stressful environmental conditions is considered the defining feature of the genus *Bacillus*, although this characteristic also applies to the recently named *Alicyclobacillus*, Amphibacillus, Aneurinibacillus, Anoxybacillus, *Brevibacillus*, Filobacillus, Gracilibacillus, Halobacillus, *Paenibacillus*, Salibacillus, Thermobacillus, Ureibacillus, and Virgibacillus.

A "*B. gibsonii* subtilisin" includes any subtilisin obtained from, or derived from, a B. *gibsonii* source. In one embodiment, a *Bacillus gibsonii* subtilisin variants provided herein can be derived from a *B. gibsonii*-clade subtilisin such as those described in WO 2015/089447, as well as those described in WO2016/205755. Other *B. gibsonii* subtilisins include those described in U.S. Patent Application Publication No. 20090275493 and variants thereof, in International Patent Application Publication No. WO2016/087403 and variants thereof, and in U.S. Pat. No. 7,449,187 and variants thereof and those disclosed in co-pending International Patent Application Publication No. WO2019/245705 entitled "Subtilisin Variants" claiming priority to U.S. Provisional Application No. 62/686,817, filed Jun. 19, 2018. In other embodiments, the *B. gibsonii* subtilisins include those polypeptides having an amino acid sequence having at least 80% sequence identity to SEQ ID NO: 1. The term "vector" refers to a nucleic acid construct used to introduce or transfer nucleic acid(s) into a target cell or tissue. A vector is typically used to introduce foreign DNA into a cell or tissue. Vectors include plasmids, cloning vectors, bacteriophages, viruses (e.g., viral vector), cosmids, expression vectors, shuttle vectors, and the like. A vector typically includes an origin of replication, a multicloning site, and a selectable marker. The process of inserting a vector into a target cell is typically referred to as transformation. The present invention includes, in some embodiments, a vector that comprises a DNA sequence encoding a serine protease polypeptide (e.g., precursor or mature serine protease polypeptide) that is operably linked to a suitable prosequence (e.g., secretory, signal peptide sequence, etc.) capable of effecting the expression of the DNA sequence in a suitable host, and the folding and translocation of the recombinant polypeptide chain.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, electroporation, conjugation, and transduction. Transformation refers to the genetic alteration of a cell which results from the uptake, optional genomic incorporation, and expression of genetic material (e.g., DNA).

The term "expression" refers to the transcription and stable accumulation of sense (mRNA) or anti-sense RNA, derived from a nucleic acid molecule of the disclosure. Expression may also refer to translation of mRNA into a polypeptide. Thus, the term "expression" includes any step involved in the "production of the polypeptide" including, but not limited to, transcription, post-transcriptional modifications, translation, post-translational modifications, secretion and the like.

The phrases "expression cassette" or "expression vector" refers to a nucleic acid construct or vector generated recombinantly or synthetically for the expression of a nucleic acid of interest (e.g., a foreign nucleic acid or transgene) in a target cell. The nucleic acid of interest typically expresses a protein of interest. An expression vector or expression cassette typically comprises a promoter nucleotide sequence that drives or promotes expression of the foreign nucleic acid. The expression vector or cassette also typically includes other specified nucleic acid elements that permit transcription of a particular nucleic acid in a target cell. A recombinant expression cassette can be incorporated into a plasmid, chromosome, mitochondrial DNA, plastid DNA, virus, or nucleic acid fragment. Some expression vectors have the ability to incorporate and express heterologous DNA fragments in a host cell or genome of the host cell. Many prokaryotic and eukaryotic expression vectors are commercially available. Selection of appropriate expression vectors for expression of a protein from a nucleic acid sequence incorporated into the expression vector is within the knowledge of those of skill in the art.

As used herein, a nucleic acid is "operably linked" with another nucleic acid sequence when it is placed into a functional relationship with another nucleic acid sequence. For example, a promoter or enhancer is operably linked to a nucleotide coding sequence if the promoter affects the transcription of the coding sequence. A ribosome binding site may be operably linked to a coding sequence if it is positioned so as to facilitate translation of the coding sequence. Typically, "operably linked" DNA sequences are contiguous. However, enhancers do not have to be contiguous. Linking is accomplished by ligation at convenient restriction sites. If such sites do not exist, synthetic oligonucleotide adaptors or linkers may be used in accordance with conventional practice.

The term "gene" refers to a polynucleotide (e.g., a DNA segment), that encodes a polypeptide and includes regions preceding and following the coding regions. In some instances, a gene includes intervening sequences (introns) between individual coding segments (exons).

The term "recombinant", when used with reference to a cell typically indicates that the cell has been modified by the introduction of a foreign nucleic acid sequence or that the cell is derived from a cell so modified. For example, a recombinant cell may comprise a gene not found in identical form within the native (non-recombinant) form of the cell, or a recombinant cell may comprise a native gene (found in the native form of the cell) that has been modified and re-introduced into the cell. A recombinant cell may comprise a nucleic acid endogenous to the cell that has been modified without removing the nucleic acid from the cell; such modifications include those obtained by gene replacement, site-specific mutation, and related techniques known to those of ordinary skill in the art. Recombinant DNA technology includes techniques for the production of recombinant DNA in vitro and transfer of the recombinant DNA into cells where it may be expressed or propagated, thereby producing a recombinant polypeptide. "Recombination" and "recombining" of polynucleotides or nucleic acids refer generally to the assembly or combining of two or more nucleic acid or polynucleotide strands or fragments to generate a new polynucleotide or nucleic acid.

A nucleic acid or polynucleotide is said to "encode" a polypeptide if, in its native state or when manipulated by methods known to those of skill in the art, it can be transcribed and/or translated to produce the polypeptide or a fragment thereof. The anti-sense strand of such a nucleic acid is also said to encode the sequence.

The terms "host strain" and "host cell" refer to a suitable host for an expression vector comprising a DNA sequence of interest.

A "protein" or "polypeptide" comprises a polymeric sequence of amino acid residues. The terms "protein" and "polypeptide" are used interchangeably herein. The single and 3-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code.

The terms "prosequence" or "propeptide sequence" refer to an amino acid sequence between the signal peptide sequence and mature protease sequence that is necessary for the proper folding and secretion of the protease; they are sometimes referred to as intramolecular chaperones. Cleavage of the prosequence or propeptide sequence results in a mature active protease. Bacterial serine proteases are often expressed as pro-enzymes. Examples of modified propeptides are provided, for example, in WO 2016/205710.

The terms "signal sequence" and "signal peptide" refer to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "mature" form of a protein, polypeptide, or peptide refers to the functional form of the protein, polypeptide, or peptide without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polypeptides that are involved in post-translational activity (e.g., polypeptides cleaved therefrom to leave the mature form of a protein or peptide).

The term "wildtype", with respect to a polypeptide, refers to a naturally-occurring polypeptide that does not include a man-made substitution, insertion, or deletion at one or more amino acid positions. Similarly, the term "wildtype", with respect to a polynucleotide, refers to a naturally-occurring polynucleotide that does not include a man-made substitution, insertion, or deletion at one or more nucleotides. A polynucleotide encoding a wildtype polypeptide is, however, not limited to a naturally-occurring polynucleotide, and encompasses any polynucleotide encoding the wildtype or parental polypeptide.

The term "parent", with respect to a polypeptide, includes reference to a naturally-occurring, or wildtype, polypeptide or to a naturally-occurring polypeptide in which a man-made substitution, insertion, or deletion at one or more amino acid positions has been made. The term "parent" with respect to a polypeptide also includes any polypeptide that has protease activity that serves as the starting polypeptide for alteration, such as substitutions, additions, and/or deletions, to result in a variant having one or more alterations in comparison to the starting polypeptide. That is, a parental, or reference polypeptide is not limited to a naturally-occurring wildtype polypeptide, and encompasses any wildtype, parental, or reference polypeptide. Similarly, the term "parent," with respect to a polynucleotide, can refer to a naturally-occurring polynucleotide or to a polynucleotide that does include a man-made substitution, insertion, or deletion at one or more nucleotides. The term "parent" with respect to a polynucleotide also includes any polynucleotide that encodes a polypeptide having protease activity that serves as the starting polynucleotide for alteration to result in a variant protease having a modification, such as substitutions, additions, and/or deletions, in comparison to the starting polynucleotide. That is, a polynucleotide encoding a wildtype, parental, or reference polypeptide is not limited to a naturally-occurring polynucleotide, and encompasses any polynucleotide encoding the wildtype, parental, or reference polypeptide. In some embodiments, the parent polypeptide, as provided herein, comprises a *B. gibsonii* subtilisin having a glutamate residue (E) at a position corresponding to position 39 of SEQ ID NO: 1. Such parent polypeptides comprising a glutamate residue at a position corresponding to position 39 of SEQ ID NO: 1 may be *B. gibsonii* subtilisin engineered to have the glutamate at that position or may naturally contain a glutamate at a position corresponding to position 39 of SEQ ID NO: 1.

The term "naturally-occurring" refers to, for example, a sequence and residues contained therein (e.g., polypeptide sequence and amino acids contained therein or nucleotide sequence and nucleotides contained therein) that are found in nature. Conversely, the term "non-naturally occurring" refers to, for example, a sequence and residues contained therein (e.g., polypeptide sequences and amino acids contained therein or nucleotide sequence and nucleic acids contained therein) that are not found in nature.

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related protein or a reference protein.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question. To exemplify, "proteases derived from *Bacillus*" refers to those enzymes having proteolytic activity that are naturally produced by *Bacillus*, as well as to serine proteases like those produced by *Bacillus* sources but which through the use of genetic engineering techniques are produced by other host cells transformed with a nucleic acid encoding the serine proteases.

The term "identical" in the context of two polynucleotide or polypeptide sequences refers to the nucleotides or amino acids in the two sequences that are the same when aligned for maximum correspondence, as measured using sequence comparison or analysis algorithms described below and known in the art.

The phrases "% identity" or percent identity" or "PID" refers to protein sequence identity. Percent identity may be determined using standard techniques known in the art. The percent amino acid identity shared by sequences of interest can be determined by aligning the sequences to directly compare the sequence information, e.g., by using a program such as BLAST, MUSCLE, or CLUSTAL. The BLAST algorithm is described, for example, in Altschul et al., J Mol Biol, 215:403-410 (1990) and Karlin et al., Proc Natl Acad Sci USA, 90:5873-5787 (1993). A percent (%) amino acid sequence identity value is determined by the number of matching identical residues divided by the total number of residues of the "reference" sequence including any gaps created by the program for optimal/maximum alignment. BLAST algorithms refer to the "reference" sequence as the "query" sequence.

As used herein, "homologous proteins" or "homologous proteases" refers to proteins that have distinct similarity in primary, secondary, and/or tertiary structure. Protein homology can refer to the similarity in linear amino acid sequence when proteins are aligned. Homology can be determined by amino acid sequence alignment, e.g., using a program such as BLAST, MUSCLE, or CLUSTAL. Homologous search of protein sequences can be done using BLASTP and PSI-BLAST from NCBI BLAST with threshold (E-value cut-off) at 0.001. (Altschul et al., "Gapped BLAST and PSI BLAST a new generation of protein database search programs", Nucleic Acids Res, Set 1; 25 (17): 3389-402 (1997)). The BLAST program uses several search parameters, most of which are set to the default values. The NCBI BLAST algorithm finds the most relevant sequences in terms of biological similarity but is not recommended for query sequences of less than 20 residues (Altschul et al., Nucleic Acids Res, 25:3389-3402, 1997 and Schaffer et al., Nucleic Acids Res, 29:2994-3005, 2001). Exemplary default BLAST parameters for a nucleic acid sequence searches include: Neighboring words threshold=11; E-value cut-off=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=11; and Gap extension=1. Using this information, protein sequences can be grouped and/or a phylogenetic tree built therefrom. Amino acid sequences can be entered in a program such as the Vector NTI Advance suite and a Guide Tree can be created using the Neighbor Joining (NJ) method (Saitou and Nei, Mol Biol Evol, 4:406-425, 1987). The tree construction can be calculated using Kimura's correction for sequence distance and ignoring positions with gaps. A program such as AlignX can display the calculated distance values in parenthesis following the molecule name displayed on the phylogenetic tree.

Understanding the homology between molecules can reveal the evolutionary history of the molecules as well as information about their function; if a newly sequenced protein is homologous to an already characterized protein, there is a strong indication of the new protein's biochemical function. Two molecules are said to be homologous if they have been derived from a common ancestor. Homologous molecules, or homologs, can be divided into two classes, paralogs and orthologs. Paralogs are homologs that are present within one species. Paralogs often differ in their detailed biochemical functions. Orthologs are homologs that are present within different species and have very similar or identical functions. A protein superfamily is the largest grouping (clade) of proteins for which common ancestry can be inferred. Usually this common ancestry is based on sequence alignment and mechanistic similarity. Superfamilies typically contain several protein families which show sequence similarity within the family. The term "protein clan" is commonly used for protease superfamilies based on the MEROPS protease classification system. As used herein, the term "subtilisin" includes any member of the S8 serine protease family as described in MEROPS—The Peptidase Data base (Rawlings, N. D., et al (2016) Twenty years of the MEROPS database of proteolytic enzymes, their substrates and inhibitors. Nucleic Acids Res 44, D343-D350).

The CLUSTAL W algorithm is another example of a sequence alignment algorithm (See, Thompson et al., Nucleic Acids Res, 22:4673-4680, 1994). Default parameters for the CLUSTAL W algorithm include: Gap opening penalty=10.0; Gap extension penalty=0.05; Protein weight matrix=BLOSUM series; DNA weight matrix=IUB; Delay divergent sequences %=40; Gap separation distance=8; DNA transitions weight=0.50; List hydrophilic residues=GPSNDQEKR; Use negative matrix=OFF; Toggle Residue specific penalties=ON; Toggle hydrophilic penalties=ON; and Toggle end gap separation penalty=OFF. In CLUSTAL algorithms, deletions occurring at either terminus are included. For example, a variant with a five amino acid deletion at either terminus (or within the polypeptide) of a polypeptide of 500 amino acids would have a percent sequence identity of 99% (495/500 identical residues×100) relative to the "reference" polypeptide. Such a variant would be encompassed by a variant having "at least 99% sequence identity" to the polypeptide.

A nucleic acid or polynucleotide is "isolated" when it is at least partially or completely separated from other components, including but not limited to, for example, other proteins, nucleic acids, cells, etc. Similarly, a polypeptide, protein or peptide is "isolated" when it is at least partially or completely separated from other components, including but not limited to, for example, other proteins, nucleic acids, cells, etc. On a molar basis, an isolated species is more abundant than are other species in a composition. For example, an isolated species may comprise at least about 60%, about 65%, about 70%, about 75%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a nucleic acid or a protein sample, respectively, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than in a starting composition.

The term "cleaning activity" refers to a cleaning performance achieved by a serine protease polypeptide, variant, or reference subtilisin under conditions prevailing during the proteolytic, hydrolyzing, cleaning, or other process of the disclosure. In some embodiments, cleaning performance of a serine protease or reference subtilisin may be determined by using various assays for cleaning one or more enzyme sensitive stain on an item or surface (e.g., a stain resulting from food, grass, blood, ink, milk, oil, and/or egg protein). Cleaning performance of one or more subtilisin variant described herein or reference subtilisin can be determined by subjecting the stain on the item or surface to standard wash condition(s) and assessing the degree to which the stain is removed by using various chromatographic, spectrophotometric, or other quantitative methodologies. Exemplary cleaning assays and methods are known in the art and include, but are not limited to those described in WO99/34011 and U.S. Pat. No. 6,605,458, as well as those cleaning assays and methods included in the Examples provided below.

The term "effective amount" of one or more subtilisin variant described herein or reference subtilisin refers to the amount of protease that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, tablet, bar) composition is required, etc.

The term "adjunct material" refers to any liquid, solid, or gaseous material included in cleaning composition other than one or more subtilisin variant described herein, or recombinant polypeptide or active fragment thereof. In some embodiments, the cleaning compositions of the present disclosure include one or more cleaning adjunct materials. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the protease enzyme used in the composition.

Cleaning compositions and cleaning formulations include any composition that is suited for cleaning, bleaching, disinfecting, and/or sterilizing any object, item, and/or surface. Such compositions and formulations include, but are not limited to, for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwashing compositions (e.g., "hand" or "manual" dishwashing detergents) and automatic dishwashing compositions (e.g., "automatic dishwashing detergents"). Single dosage unit forms also find use with the present invention, including but not limited to pills, tablets, gelcaps, or other single dosage units such as pre-measured powders or liquids.

Cleaning composition or cleaning formulations, as used herein, include, unless otherwise indicated, granular or powder-form all-purpose or heavy-duty washing agents, especially cleaning detergents; liquid, granular, gel, solid, tablet, paste, or unit dosage form all-purpose washing agents, especially the so-called heavy-duty liquid (HDL) detergent or heavy-duty dry (HDD) detergent types; liquid fine-fabric detergents; hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

The term "detergent composition" or "detergent formulation" is used in reference to a composition intended for use in a wash medium for the cleaning of soiled or dirty objects, including particular fabric and/or non-fabric objects or items. In some embodiments, the detergents of the disclosure comprise one or more subtilisin variant described herein and, in addition, one or more surfactants, transferase(s), hydrolytic enzymes, oxido reductases, builders (e.g., a builder salt), bleaching agents, bleach activators, bluing agents, fluorescent dyes, caking inhibitors, masking agents, enzyme stabilizers, calcium, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some embodiments are directed to cleaning compositions or detergent compositions that do not contain any phosphate (e.g., phosphate salt or phosphate builder).

The phrase "composition(s) substantially-free of boron" or "detergent(s) substantially-free of boron" refers to composition(s) or detergent(s), respectively, that contain trace amounts of boron, for example, less than about 1000 ppm (1 mg/kg or liter equals 1 ppm (parts per million)), less than about 100 ppm, less than about 50 ppm, less than about 10 ppm, or less than about 5 ppm, or less than about 1 ppm, perhaps from other compositions or detergent constituents.

The term "bleaching" refers to the treatment of a material (e.g., fabric, laundry, pulp, etc.) or surface for a sufficient length of time and/or under appropriate pH and/or temperature conditions to effect a brightening (i.e., whitening) and/or cleaning of the material. Examples of chemicals suitable for bleaching include, but are not limited to, for example, $ClO_2$, $H_2O_2$, peracids, $NO_2$, etc. Bleaching agents also include enzymatic bleaching agents such as perhydrolase and arylesterases. Another embodiment is directed to a composition comprising one or more subtilisin variant described herein, and one or more perhydrolase, such as, for example, is described in WO2005/056782, WO2007/106293, WO 2008/063400, WO2008/106214, and WO2008/106215.

The term "wash performance" of a protease (e.g., one or more subtilisin variant described herein, or recombinant polypeptide or active fragment thereof) refers to the contribution of one or more subtilisin variant described herein to washing that provides additional cleaning performance to the detergent as compared to the detergent without the addition of the one or more subtilisin variant described herein to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

The phrase "relevant washing conditions" is used herein to indicate the conditions, particularly washing temperature, time, washing mechanics, sud concentration, type of detergent and water hardness, actually used in households in a hand dishwashing, automatic dishwashing, or laundry detergent market segment.

The term "disinfecting" refers to the removal of contaminants from the surfaces, as well as the inhibition or killing of microbes on the surfaces of items.

The term "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, the filler salt is sodium sulfate.

Disclosed herein is one or more subtilisin variant useful for cleaning applications and in methods of cleaning, as well as in a variety of industrial applications. Also disclosed herein is one or more isolated, recombinant, substantially pure, or non-naturally occurring subtilisin variant. In some embodiments, one or more subtilisin variant described herein is useful in cleaning applications and can be incorporated into cleaning compositions that are useful in methods of cleaning an item or a surface in need thereof.

One embodiment is directed to a subtilisin variant comprising an amino acid sequence comprising one or more amino acid substitutions at one or more positions selected from: X003V, X004T, X008V, X009A/C/E/G/H/K/M/N/Q/S/W/Y, X010A/K/M/N/Q/W, X011A/I/S/T, X012A/C/D/E/G/M/N/R/S/T/V/W, X014D, X015D/E/F/H/I/K/M/P/Q/V/W/Y, X016L/M/S, X017C/E/F/G/I/L/N/V/W/Y, X018A/C/D/E/F/G/L/M/Q/T, X019A/C/D/E/F/H/I/K/L/N/Q/S/T/W/Y, X020A/C/D/M/N/T, X024A/E, X025A/C/D/E/M/N, X026A/I, X027K, X033T, X036A/C/E/I/L/M/Q/T/V, X042C/D/E/M/Q, X043L, X044C/E/F/G/H/I/K/L/N/Q/S/T/V/W/Y, X047I/Y, X0SOI, X052A/C/D/H/L/M/N/S/T/Y, X054A/C/G/L/M/N/T/V, X055A/C/D/E/H/M/N/S/Y, X057D/E/H/M/N/Q/T, X059A/C/D/E/M/N/Q/T, X060S, X069S, X076A/D/E/F/H/K/L/M/N/R/T/Y, X082A, X084D/F/H/Y, X085S, X095A/N, X096M/Q, X097E/H/K, X101T, X102L/M, X104A/D/H/M/N/T/V/W/Y, X10SV, X107K/M, X110L, X113T/V, X114V, XIISE/H/Q. X116E/H, X118D/E/N, X120V, X122L, X128G, X129A/H/N/Y, X131A/D/E/I/M/N/P/Q/T/V, X133M, X135A/E/F/H/I/K/L/M/S/T/V/W/Y, X136M, X137L, X139E/S, X141E/H/N, X142A/D/E/H/M/N/Q, X143E/H/M/N/Q/V, X144E/N, X145C, X147C, X148L/V, X150M, X154D, X156A/C/D/N/T, X157A/C/D/E/N/Q, X158A/C/F/L/M/N/Q/T/V/W/Y, X159L, X160A/C/D/M/S/T, X161W, X164A/K/M/Q/Y, X166D/E/I/P/Q/V, X167E, X169L, X170G, X174V, X176A/C/D/E/L/M/N/S, X177A/C/D/E/G/H/K/L/M/Q/S/W/Y, X178D, X179A/C/E/F/G/H/I/K/M/Q/S/V/W/Y, X180K, X182A/C/D/E/G/H/I/K/L/P/Q/S/T/V/W/Y, X186F, X188A/C/D/E/I/L/M/N/Q/S/V/W/Y, X189C/D/E, X190M, X191E, X192C/M, X193A/M, X198D/E, X200H/I/K/M/V/Y, X207K/L/N/Q/T, X209P, X210C/D/E/F/G/L/N/P/Q/Y, X211E/K/L/Q/R, X212A/C/Q/S, X218C/S, X224V, X227M/Q, X228L, X230E, X231C/E/H/I/L/N/Q/S/T, X232F/H/Q/R/W, X234A/D/E/M/T/W/Y, X236D/G/S/T, X238A/D/E/M/V, X239D/E/L/M/N/T, X242A, X245E, X246A/L/S, X247E/Q, X249C/D/E/F/I/L/S/Y, X250D/S/T, X253D/E/P, X254P/Y, X255A/C/D/E/F/I/M/N/V/W, X256C/E/F/H/L/M/W/Y, X257C/M, X259D/E/M/N, X262L, X263D/Q, X264T, X265A/M/N/Q, X266L/M/N/Q/R, X268A/C/D/E, and X269H/P/W; where the amino acid positions of the variant are numbered by correspondence with the amino acid sequence of SEQ ID NO: 1.

In one embodiment, the subtilisin variant provided herein comprises an amino acid sequence having a glutamate residue (E) at a position corresponding to position 39 of SEQ ID NO: 1 and further comprises one or more amino acid substitutions at one or more positions selected from: X003V, X004T, X008V, X009A/C/E/G/H/K/M/N/Q/S/W/Y, X010A/K/M/N/Q/W, X011A/I/S/T, X012A/C/D/E/G/M/N/R/S/T/V/W, X014D. X015D/E/F/H/I/K/M/P/Q/V/W/Y, X016L/M/S, X017C/E/F/G/I/L/N/V/W/Y, X018A/C/D/E/F/G/L/M/Q/T, X019A/C/D/E/F/H/I/K/L/N/Q/S/T/W/Y, X020A/C/D/M/N/T, X024A/E, X025A/C/D/E/M/N, X026A/I, X027K, X033T, X036A/C/E/I/L/M/Q/T/V, X042C/D/E/M/Q, X043L, X044C/E/F/G/H/I/K/L/N/Q/S/T/V/W/Y, X047I/Y, X0501, X052A/C/D/H/L/M/N/S/T/Y, X054A/C/G/L/M/N/T/V, X055A/C/D/E/H/M/N/S/Y, X057D/E/H/M/N/Q/T, X059A/C/D/E/M/N/Q/T, X060S, X069S, X076A/D/E/F/H/K/L/M/N/R/T/Y, X082A, X084D/F/H/Y, X085S, X095A/N, X096M/Q, X097E/H/K, X101T, X102L/M, X104A/D/H/M/N/T/V/W/Y, X105V, X107K/M, X110L, X113T/V, X114V, X115E/H/Q, X116E/H, X118D/E/N, X120V, X122L, X128G, X129A/H/N/Y, X131A/D/E/I/M/N/P/Q/T/V, X133M, X135A/E/F/H/I/K/L/M/S/T/V/W/Y, X136M, X137L, X139E/S, X141E/H/N, X142A/D/E/H/M/N/Q, X143E/H/M/N/Q/V, X144E/N, X145C, X147C, X148L/V, X150M, X154D, X156A/C/D/N/T, X157A/C/D/E/N/Q, X158A/C/F/L/M/N/Q/T/V/W/Y, X159L, X160A/C/D/M/S/T, X161W, X164A/K/M/Q/Y, X166D/E/I/P/Q/V, X167E, X169L, X170G, X174V, X176A/C/D/E/L/M/N/S, X177A/C/D/E/G/H/K/L/M/Q/S/W/Y, X178D, X179A/C/E/F/G/H/I/K/M/Q/S/V/W/Y, X180K, X182A/C/D/E/G/H/I/K/L/P/Q/S/T/V/W/Y, X186F, X188A/C/D/E/I/L/M/N/Q/S/V/W/Y, X189C/D/E, X190M, X191E, X192C/M, X193A/M, X198D/E, X200H/I/K/M/V/Y, X207K/L/N/Q/T, X209P, X210C/D/E/F/G/L/N/P/Q/Y, X211E/K/L/Q/R, X212A/C/Q/S, X218C/S, X224V, X227M/Q. X228L, X230E, X231C/E/H/I/L/N/Q/S/T, X232F/H/Q/R/W, X234A/D/E/M/T/W/Y, X236D/G/S/T, X238A/D/E/M/V, X239D/E/L/M/N/T, X242A, X24SE, X246A/L/S, X247E/Q, X249C/D/E/F/I/L/S/Y, X250D/S/T, X253D/E/P, X254P/Y, X255A/C/D/E/F/I/M/N/V/W, X256C/E/F/H/L/M/W/Y, X257C/M, X259D/E/M/N, X262L, X263D/Q, X264T, X265A/M/N/Q, X266L/M/N/Q/R, X268A/C/D/E, and X269H/P/W; where the amino acid positions of the variant are numbered by correspondence with the amino acid sequence of SEQ ID NO: 1. In some embodiments, the subtilisin variant demonstrates an improved performance (PI (performance index) value of ≥1.1) in an assay on one of the following stains, BMI, PAS-38, crème brûlée (as provided in Example 1), or shows an improved stability (PI value of ≥1.1) in Tris-EDTA buffer compared to a subtilisin having a glutamate at a position corresponding to position 39 in SEQ ID NO: 1.

Another embodiment is directed to a subtilisin variant comprising an amino acid sequence having a glutamate residue (E) at a position corresponding to position 39 of SEQ ID NO: 1 and further comprising one or more amino acid substitutions at one or more positions selected from: X003V, X004T, X008V, X009A/C/E/G/H/K/M/N/Q/S/W/Y, X010A/K/M/N/Q/W, X011A/I/S/T, X012A/C/D/E/G/M/N/R/S/T/V/W, X014D, X015D/E/F/H/I/K/M/P/Q/V/W/Y, X016L/M/S, X017C/E/F/G/I/L/N/V/W/Y, X018A/C/D/E/F/G/L/M/Q/T, X019A/C/D/E/F/H/I/K/L/N/Q/S/T/W/Y, X020A/C/D/M/N/T, X024A/E, X025A/C/D/E/M/N, X026A/I, X027K, X033T, X036A/C/E/I/L/M/Q/T/V, X042C/D/E/M/Q, X043L, X044C/E/F/G/H/I/K/L/N/Q/S/T/V/W/Y, X047I/Y, X050I, X052A/C/D/H/L/M/N/S/T/Y, X054A/C/G/L/M/N/T/V, X055A/C/D/E/H/M/N/S/Y, X057D/E/H/M/N/Q/T, X059A/C/D/E/M/N/Q/T, X060S, X069S, X076A/D/E/F/H/K/L/M/N/R/T/Y, X082A, X084D/F/H/Y, X085S, X095A/N, X096M/Q, X097E/H/K, X101T, X102L/M, X104A/D/H/M/N/T/V/W/Y, X105V, X107K/M, X110L, X113T/V, X114V, X115E/H/Q, X116E/H, X118D/E/N, X120V, X122L, X128G, X129A/H/N/Y, X131A/D/E/I/M/N/P/Q/T/V, X133M, X135A/E/F/H/I/K/L/M/S/T/V/W/Y, X136M, X137L, X139E/S, X141E/H/N, X142A/D/E/H/M/N/Q, X143E/H/M/N/Q/V, X144E/N, X145C, X147C, X148L/V, X150M, X154D, X156A/C/D/N/T, X157A/C/D/E/N/Q, X158A/C/F/L/M/N/Q/T/V/W/Y, X159L, X160A/C/D/M/S/T, X161W, X164A/K/M/Q/Y, X166D/E/I/P/Q/V, X167E, X169L, X170G, X174V, X176A/C/D/E/L/M/N/S, X177A/C/D/E/G/H/K/L/M/Q/S/W/Y, X178D, X179A/C/E/F/G/H/I/K/M/Q/S/V/W/Y, X180K, X182A/C/D/E/G/H/I/K/L/P/Q/S/T/V/W/Y, X186F, X188A/C/D/E/I/L/M/N/Q/S/V/W/Y, X189C/D/E, X190M, X191E, X192C/M, X193A/M, X198D/E, X200H/I/K/M/V/Y, X207K/L/N/Q/T, X209P, X210C/D/E/F/G/L/N/P/Q/Y, X211E/K/L/Q/R, X212A/C/Q/S, X218C/S, X224V, X227M/Q, X228L, X230E, X231C/E/H/I/L/N/Q/S/T, X232F/H/Q/R/W, X234A/D/E/M/T/W/Y, X236D/G/S/T, X238A/D/E/M/V, X239D/E/L/M/N/T, X242A, X245E, X246A/L/S, X247E/Q, X249C/D/E/F/I/L/S/Y, X250D/S/T, X253D/E/P, X254P/Y, X255A/C/D/E/F/I/M/N/V/W, X256C/E/F/H/L/M/W/Y, X257C/M, X259D/E/M/N, X262L, X263D/Q, X264T, X265A/M/N/Q, X266L/M/N/Q/R, X268A/C/D/E, and X269H/P/W; where the amino acid positions of the variant are numbered by correspondence with the amino acid sequence of SEQ ID NO: 1 and where the variant has at least 80%, 85%, 90%, 91%, 92%, 93%, 94%, 95%, 96%, 97%, 98%, or 99% sequence identity to the amino acid sequence of SEQ ID NO: 1. In some embodiments, the subtilisin variant demonstrates an improved performance (PI value of ≥1.1) in an assay on one of the following stains, BMI, PAS-38, crème brûlée (as provided in Example 1), or shows an improved stability (PI value of ≥1.1) in Tris-EDTA buffer compared to a subtilisin having a glutamate at a position corresponding to position 39 in SEQ ID NO: 1.

Another embodiment is directed to a subtilisin variant comprising an amino acid sequence having a glutamate residue (E) at a position corresponding to position 39 of SEQ ID NO: 1 and further comprising one or more amino acid substitutions at one or more positions selected from X008V, X011S, X012A/C/D/E/G/M/N/S/T/V, X014D, X016M, X017C/I/N/W, X018T, X019A/D/F/H/I/L/Q/S/W/Y, X024A/E, X025M/N, X042D/E/M, X044E/G/I/N/T, X052T, X054T/V, X055E, X059D/E, X060S, X069S, X096Q, X115E, X128G, X129H, X131D, X135E/F/H/I/S/T/V, X137L, X139E/S, X141E/H/N, X143E/H/M/N/Q/V, X156C, X157D/E, X158C/T/V, X161W, X164M/Q/Y, X166V, X167E, X176D/E/M/N/S, X177C/E, X179I/S/V/W, X182D/E/P/Q/T, X188D/E/S/V, X190M, X193M, X198D, X207K/N/T, X210D/E, X211E/Q. X231I/S, X234D, X236D, X238D, X246S, X249D, X250D/T, and X269H; where the amino acid positions of the variant are numbered by correspondence with the amino acid sequence of SEQ ID NO: 1. In some embodiments, the B. gibsonii subtilisin variant demonstrates an improved cleaning performance (PI value of ≥1.1) in a BMI HDL assay (as provided in Example 1) compared to a subtilisin having a glutamate at a position corresponding to position 39 in SEQ ID NO: 1.

Another embodiment is directed to a subtilisin variant comprising an amino acid sequence having a glutamate residue (E) at a position corresponding to position 39 of SEQ ID NO: 1 and further comprising one or more amino acid substitutions at one or more positions selected from X003V, X009Q/W, X012R/W, X015M/Q, X016M, X024A, X042M, X054N, X057M/Q, X059N, X076R, X104A, X131A/M/P/Q, X142N/Q, X144E, X145C, X147C, X157A/Q, X158A/N/Q/T, X160A, X166Q, X176A, X177Q, X186F, X190M, X211Q, X212A, X224V, X227Q, X232F/Q/R, X234A, X238A, X255N, X256M, X257M, X259M, X265M/N/Q, and X266Q/R; where the amino acid positions of the variant are numbered by correspondence with the amino acid sequence of SEQ ID NO: 1. In some embodiments, the subtilisin variant demonstrates an improved cleaning performance (PI value of ≥1.1) in a BMI HDD assay (as provided in Example 1) compared to a subtilisin having a glutamate at a position corresponding to position 39 in SEQ ID NO: 1.

Another embodiment is directed to a subtilisin variant comprising an amino acid sequence having a glutamate residue (E) at a position corresponding to position 39 of SEQ ID NO: 1 and further comprising one or more amino acid substitutions at one or more positions selected from X009H/K/N/W, X011A/1, X012A/M/N/R/S/V, X015F/I/K/V, X016L/M, X017F/G/I/L/N/V/W, X018F, X019C/K/L/Q, X020A/D/M/N/T, X024A, X025A/D/N, X036A/L, X052D/H, X054A/G/L/M/V, X0SSA/D/H/S/Y, X059A/M/N, X060S, X069S, X076K/L, X095N, X096Q, X097K, X102L/M, X107K, X110L, X113T, X118D, X120V, X122L, X128G, X129A/H/N/Y, X131M/N/P, X136M, X143N, X144N, X145C, X157A/D, X158Q/T, X159L, X160D/M/S, X166I, X170G, X176L, X177A/D/G/K/L/M/S/Y, X179A/K, X182A/D/S/Y, X188M, X191E, X207L, X210E/G/Q, X211E/Q/R, X218S, X227M, X232F/W, X256L/Y, X263Q, X265A/M/Q, and X268A; where the amino acid positions of the variant are numbered by correspondence with the amino acid sequence of SEQ ID NO: 1. In some embodiments, the subtilisin variant demonstrates an improved cleaning performance (PI value of ≥1.1) in a PAS-38 assay (as provided in Example 1) compared to a subtilisin having a glutamate at a position corresponding to position 39 in SEQ ID NO: 1.

Another embodiment is directed to a subtilisin variant comprising an amino acid sequence having a glutamate residue (E) at a position corresponding to position 39 of SEQ ID NO: 1 and further comprising one or more amino acid substitutions at one or more positions selected from X009A/C/E/M/N/Y, X010A/K/M/N/Q/W, X011A/T, X012A/C/D/E/M, X014D, X015D/E/H/I/M/V/W/Y, X016L/M, X017C/E, X018C/D/E/M, X019A/C/D/E/F/H/I/K/L/N/Q/S/T/W/Y, X020C/D, X024A/E, X025A/C/D/E/M/N, X026A, X027K, X036C/E/Q/V, X042C/D/E, X043L, X044C/E/G/H/I/L/N/ Q/S/T, X052A/C/D/L/M/N, X054A/C/L/M/V, X055A/C/D/ E/M, X057D/E. X059A/C/D/E/M/N/Q/T, X060S, X076D/ E/N, X082A, X084D, X096Q, X097E/H, X104A/D/H/N/V/ Y, X115H, X116E, X128G, X129H, X131D/E, X135A/E/ F/H/I/K/L/M/S/T/V/W/Y, X139E, X141E, X142D/E, X143E, X144E, X147C, X148L, X154D, X156A/C/D/N/T, X157C/D/E, X158C/L/Q/T/Y, X159L, X164A/K/M/Q/Y, X166D/E, X167E, X169L, X174V, X176A/C/D/E/N, X177C/D/E, X178D, X179A/C/E/F/G/H/I/K/M/Q/S/V/W/ Y,X180K, X182C/D/E, X188C/D/E, X189C/D/E, X193A/ M, X198D/E, X207K/L/N/Q/T, X209P, X210C/D/E/L/N/Y, X211E/K/L/Q, X212C/Q, X228L, X230E, X231C/E/L/N/Q, X232F, X234D/E/T/W/Y, X236D/T, X238A/D/E/M/V, X239D/E/M/N, X245E, X246A/L, X247E/Q, X249C/D/E/ L/Y, X250D, X253D/E/P, X254Y, X255A/C/D/E, X256C/ E/Y, X257C, X259D/E/M/N, X262L, X263D, X268C/D/E, and X269H/P/W; where the amino acid positions of the variant are numbered by correspondence with the amino acid sequence of SEQ ID NO: 1. In some embodiments, the subtilisin variant demonstrates an improved cleaning performance (PI value of ≥1.1) in a crème brûlée assay (as provided in Example 1) compared to a subtilisin having a glutamate at a position corresponding to position 39 in SEQ ID NO: 1.

In another embodiment, subtilisin variants are provided that have an improved crème brûlée cleaning performance compared to a parent subtilisin (e.g. SEQ ID NO: 1), where the variant comprises an amino acid substitution at one or more positions selected from 9, 10, 12, 14, 15, 17, 18, 19, 20, 24, 25, 27, 36, 42, 44, 52, 54, 55, 57, 59, 76, 84, 97, 104, 116, 131, 135, 139, 141, 142, 143, 147, 154, 156, 157, 158, 164, 166, 167, 176, 177, 178, 179, 180, 182, 188, 189, 198, 207, 210, 211, 212, 230, 231, 234, 236, 238, 239, 245, 247, 249, 250, 253, 254, 255, 256, 257, 259, 263, 268, and 269, where the positions are numbered corresponding to SEQ ID NO: 1, and where the substitution introduces an overall negative net charge relative to the parent subtilisin in the application. In some embodiments, the variant comprises one or more negatively charged amino acid substitutions at one or more positions or replaces a positively charged amino acid at one or more positions, selected from X009C/E/Y, X010A/K/M/ N/Q/W, X012C/D/E, X014D, X015D/E/Y, X017C/E, X018C/D/E, X019A/C/D/E/F/H/I/K/L/N/Q/S/T/W/Y, X020C/D, X024E, X025C/D/E, X027K, X036C/E, X042C/ D/E, X044C/E/G/H/I/L/N/Q/S/T, X052C/D, X054C, X055C/D/E, X057D/E. X059C/D/E, X076D/E, X084D, X097E, X104D/Y, X116E, X131D/E, X135A/E/F/H/I/K/L/ M/S/T/V/W/Y, X139E, X141E, X142D/E, X143E, X147C, X154D, X156C/D, X157C/D/E, X158C/Y, X164A/K/M/Q/ Y, X166D/E, X167E, X176C/D/E, X177C/D/E, X178D, X179A/C/E/F/G/H/I/K/M/Q/S/V/W/Y, X180K, X182C/D/ E, X188C/D/E, X189C/D/E, X198D/E, X207K/L/N/Q/T, X210C/D/E/Y, X211E, X212C, X230E, X231C/E/L/N/Q, X234D/E/Y, X236D, X238D/E, X239D/E, X245E, X247E, X249C/D/E/Y, X250D, X253D/E, X254Y, X255C/D/E, X256C/E/Y, X257C, X259D/E, X263D, X268C/D/E, and X269H/P/W, where the positions are numbered corresponding to SEQ ID NO: 1.

In another embodiment, subtilisin variants are provided that have an improved BMI HDL cleaning performance compared to a parent subtilisin (e.g. SEQ ID NO: 1), where the variant comprises an amino acid substitution at one or more positions selected from 12, 14, 17, 19, 24, 42, 44, 55, 59, 115, 131, 135, 139, 141, 143, 156, 157, 158, 164, 167, 176, 177, 179, 182, 188, 198, 207, 210, 211, 231, 234, 236, 238, 249, 250, and 269, where the positions are numbered corresponding to SEQ ID NO: 1, and where the substitution introduces an overall negative net charge relative to the parent subtilisin in the application. In some embodiments, the variant comprises one or more negatively charged amino acid substitutions at one or more positions or replaces a positively charged amino acid at one or more positions, selected from X012C/D/E, X014D, X017C/I/N/W, X019A/ D/F/H/I/L/Q/S/W/Y, X024E, X042D/E, X044E/G/I/N/T, X055E, X059D/E, X115E, X131D, X135E/F/H/I/S/T/V, X139E, X141E, X143E/H/M/N/Q/V, X156C, X157D/E, X158C, X164M/Q/Y,X167E, X176D/E, X177C/E, X179I/ S/V/W, X182D/E, X188D/E, X198D, X207K/N/T, X210D/ E, X211E, X231I/S, X234D, X236D, X238D, X249D, X250D, and X269H, where the positions are numbered corresponding to SEQ ID NO: 1.

In another embodiment, subtilisin variants are provided that have an improved BMI HDD cleaning performance compared to a parent subtilisin (e.g. SEQ ID NO: 1), where the variant comprises an amino acid substitution at one or more positions selected from 12, 76, 186, 232, 265, and 266, where the positions are numbered corresponding to SEQ ID NO: 1, and where the substitution introduces an overall positive net charge relative to the parent subtilisin in the application. In some embodiments, the variant comprises one or more positively charged amino acid substitutions at one or more positions or replaces a negatively charged amino acid at one or more positions, selected from X012R, X076R, X186F, X232F/Q/R, X265M/N/Q, and X266R, where the positions are numbered corresponding to SEQ ID NO: 1.

Another embodiment is directed to a subtilisin variant comprising an amino acid sequence having a glutamate residue (E) at a position corresponding to position 39 of SEQ ID NO: 1 and further comprising one or more amino acid substitutions at one or more positions selected from X009N, X011A, X012A/M, X015I/V, X016L/M, X019C/K/L/Q, X020D, X024A, X025A/D/N, X052D, X054A/L/M/V, X055A/D, X059A/M/N, X060S, X096Q, X128G, X129H, X157D, X158Q/T, X159L, X177D, X179A/K, X182D, X207L, X210E, X211E/Q, X232F, and X256Y; where the amino acid positions of the variant are numbered by correspondence with the amino acid sequence of SEQ ID NO: 1. In some embodiments, the subtilisin variant demonstrates an improved cleaning performance (PI value of ≥1.1) in a PAS-38 and a crème brûlée assay (as provided in Example 1) compared to a subtilisin having a glutamate at a position corresponding to position 39 in SEQ ID NO: 1.

Another embodiment is directed to a subtilisin variant comprising an amino acid sequence having a glutamate residue (E) at a position corresponding to position 39 of SEQ ID NO: 1 and further comprising one or more amino acid substitutions at one or more positions selected from X003V, X004T, X008V, X009A/E/G/H/K/N/Q/S/W/Y, X010Q, X011A, X012A/C/G/M/N/T, X015F/H/M/P/Q/W, X016S, X017C/E/F/I/L/N/V/W/Y, X018A/D/E/L/M/Q. X019C/D/Y, X020C/D/M/N, X024A/E, X025C/D/N, X026I, X027K, X033T, X036A/C/I/L/M/Q/V, X042C/D/E/M/Q, X044C/E/ F/G/H/I/K/L/N/Q/S/T/V/W/Y, X047I/Y, X050I, X052A/M/ N/S/T/Y, X054N/V, X055C/D/E/N, X057E/H/M/N/Q/T, X059N, X076A/D/E/F/H/K/L/M/N/R/T/Y, X082A, X084D/ F/H/Y, X085S, X095A/N, X096M, X097K, X101T, X102L/ M, X104M/N/T/V/W, X105V, X107M, X113V, X114V, X115Q, X116E/H, X118D/E/N, X131A/D/E/I/M/N/P/Q/T/ V, X133M, X135A/H/I/K/L/M/S/T/V/W/Y, X136M, X142A/D/E/H/M/N/Q, X143E/H/M/N/Q, X147C, X148V, X150M, X156N/T, X157A/C/N, X158C/F/L/M/N/Q/T/V/ W/Y, X159L, X160A/C/M/S/T, X166D/E/P/Q, X170G, X176C/M, X177A/C/D/H/L/M/Q/W/Y, X179M/Q, X180K, X182A/C/E/G/H/I/K/L/P/Q/S/T/V/W/Y, X188A/C/D/E/I/L/ M/N/Q/V/W/Y, X189D, X192C/M, X193M, X200H/I/K/M/ V/Y, X209P, X210E/F/P, X211K, X212S, X218C/S, X228L, X230E, X231C/E/H/N/T, X232F/H, X234D/M, X236D/G/ S/T, X238A/D/E/M/V, X239E/L/M/T, X242A, X246A/L/S, X249E/F/I/L/S/Y, X250D/S, X253D/E, X254P, X255C/D/ E/F/I/M/V/W, X256C/E/F/H/W/Y, X264T, X266L/M/N, and X268C; where the amino acid positions of the variant are numbered by correspondence with the amino acid sequence of SEQ ID NO: 1. In some embodiments, the subtilisin variant demonstrates an improved stability (PI value of ≥1.1) in Tris-EDTA buffer (as provided in Example 1) compared to a subtilisin having a glutamate at a position corresponding to position 39 in SEQ ID NO: 1.

Another embodiment is directed to a subtilisin variant comprising an amino acid sequence having a glutamate residue (E) at a position corresponding to position 39 of SEQ ID NO: 1 and further comprising one or more amino acid substitutions at one or more positions selected from X009A/ E/H/K/N/W/Y, X010Q, X011A, X012A/C/M/N, X015F/H/ M/W, X017C/E/F/I/L/N/V/W, X018D/E/M, X019C/D/Y, X020C/D/M/N, X024A/E, X025C/D/N, X027K, X036A/C/ L/Q/V, X042C/D/E, X044C/E/G/H/I/L/N/Q/S/T, X052A/M/ N, X054V, X055C/D/E, X057E, X059N, X076D/E/K/L/N, X082A, X084D, X095N, X097K, X102L/M, X104N/V, X116E, X118D, X131D/E/M/N/P, X135A/H/I/K/L/M/S/T/ V/W/Y, X136M, X142D/E, X143E/N, X147C, X156N/T, X157A/C, X158C/L/Q/T/Y, X159L, X160M/S, X166D/E, X170G, X176C, X177A/C/D/L/M/Y, X179M/Q, X180K, X182A/C/E/S/Y, X188C/D/E/M, X189D, X193M, X209P, X210E, X211K, X218S, X228L, X230E, X231C/E/N, X232F, X234D, X236D/T, X238A/D/E/M/V, X239E/M, X246A/L, X249E/L/Y, X250D, X253D/E, X255C/D/E, X256C/E/Y, and X268C; where the amino acid positions of the variant are numbered by correspondence with the amino acid sequence of SEQ ID NO: 1. In some embodiments, the subtilisin variant demonstrates an improved cleaning performance (PI value of ≥1.1) on PAS-38 assays or crème brûlée assays (as provided in Example 1) and an improved stability (PI value of ≥1.1) in Tris-EDTA buffer (as provided in Example 1) compared to a subtilisin having a glutamate at a position corresponding to position 39 in SEQ ID NO: 1.

Another embodiment is directed to a subtilisin variant comprising an amino acid sequence having a glutamate residue (E) at a position corresponding to position 39 of SEQ ID NO: 1 and further comprising one or more amino acid substitutions at one or more positions selected from X003V, X008V, X009Q/W, X012A/C/G/M/N/T, X015M/Q, X017C/ I/N/W, X019D/Y, X024A/E, X025N, X042D/E/M, X044E/ G/I/N/T, X052T, X054N/V, XO55E, X057M/Q, X059N, X076R, X131A/D/M/P/Q, X135H/I/S/T/V, X142N/Q, X143E/H/M/N/Q, X147C, X157A, X158C/N/Q/T/V, X160A, X166Q, X176M, X177C/Q, X182E/P/Q/T, X188D/ E/V, X193M, X210E, X232F, X234D, X236D, X238A/D, X246S, and X250D, where the amino acid positions of the variant are numbered by correspondence with the amino acid sequence of SEQ ID NO: 1. In some embodiments, the subtilisin variant demonstrates an improved cleaning performance (PI value of ≥1.1) in BMI assays (as provided in Example 1) and an improved stability (PI value of ≥1.1) in Tris-EDTA buffer (as provided in Example 1) compared to a subtilisin having a glutamate at a position corresponding to position 39 in SEQ ID NO: 1.

In some embodiments, the subtilisin parent or variant molecule also comprise at least one, two, three, or more additional substitutions selected from X037E, X060D, X097D, X107E, X115D, X167D, X185E, X200E, X205D, X242D, X253D-X256E, X025R-X117I-X118N, X149S, X044P-X175N-X208N-X230H, X041F-X078D-X084A, X101G-X174A, X021V-X177I, X021V-X142G-X188A, X021V-X122L-X222S, X012L-X021V-X122L-X222S, X021V-X122L-X253D, X021V-X177V-X228I. X021V-X039T-X122L-X177E, X021V-X079L-X087E-X209N-X222S. X021V-X122L-X222S-X247N, X021V-X122L, X039E-X074D-X087E, X039E-X074D-X087E-X253D, X021V-X039E-X074D-X087E-X253D, X039E-X074D-X087E-X122L-X253D, X021V-X039E-X074D-X087E-X122L-X253D, X021V, X211S, X212N, X012L, X177V, X222S, X228I, X247N, X099E, X097D-X099E, X043V, X122L-X145S-X156A, X21IN-X212D, X211L-X212D, X127P-X211L-X212D, X212H, X012L-X122L-X222S, X127P, X145S, X21IN, and X212D.

The disclosure includes subtilisin variants having one or more modifications at a surface exposed amino acid. Surface modifications in the enzyme variants can be useful in a detergent composition by having a minimum performance index for wash performance, stability of the enzyme in detergent compositions and thermostability of the enzyme, while having at least one of these characteristics improved from a parent subtilisin enzyme. In some embodiments, the minimum performance index is at least 50%, 60%, 70%, 80%, 90%, or 95% of the parent molecule's performance index. In some embodiments, the surface modification changes the hydrophobicity and/or charge of the amino acid at that position. Hydrophobicity can be determined using techniques known in the art, such as those described in White and Wimley (White, S. H. and Wimley, W. C, (1999) Annu Rev. Biophys. Biomol. Struct. 28:319-65). Net charge of an amino acid at a pH of interest can be calculated using the pKa values of titratable chemical groups in amino acids, such as those described in Hass and Mulder (Hass, M. A. S and Mulder, F. A. A (2015) Annu Rev. Biophys. 44:53-75)

As used herein, "surface property" can be used in reference to electrostatic charge, as well as properties such as the hydrophobicity and hydrophilicity exhibited by the surface of a protein.

The subtilisin variants provided herein that have at least one of the surface modifications as suitable modifications include positions 76, 84, 97, 104, 116, 131, 135, 139, 141, 142, 143, 157, 160, 207, 211 where the amino acid positions of the variant are numbered by correspondence with the amino acid sequence in SEQ ID NO: 1.

Another embodiment is directed to one or more subtilisin variant described herein with the proviso that one or more substitutions is non-naturally occurring. Yet an even still further embodiment is directed to one or more subtilisin variant described herein wherein said variant (i) is from B. gibsonii; (ii) is isolated; (iii) has proteolytic activity; or (iv) comprises a combination of (i) to (iii). Still yet another embodiment is directed to one or more subtilisin variant described herein, wherein said variant is derived from a parent or reference polypeptide with (i) 70%, 75%, 80%, 85%, 86%, 87%, 88%, 89%, 90%, 91%, 92%, 93%, 94%, 95%, 96%, 97%, 98%, 99%, or 100% amino acid sequence identity to the amino acid sequence of SEQ ID NO: 1; or (ii) 100% amino acid sequence identity to the amino acid sequence of SEQ ID NO: 1. In still another embodiment the parent comprises the amino acid sequence of SEQ ID NO: 1. An even further embodiment is directed to one or more subtilisin variant described herein, where said variant comprises an amino acid sequence with (i) at least 70%, 75%, 80%, 85%, 86%, 87%, 88%, 89%, 90%, 91%, 92%, 93%, 94%, 95%, 96%, 97%, 98%, 99% or less than 100% amino acid sequence identity to the amino acid sequence of SEQ ID NO: 1; (ii) at least 80%, 81%, 82%, 83%, 84%, 85%, 86%, 87%, 88%, 89%, 90%, 91%, 92%, 93%, 94%, 95%, 96%, 97%, 98%, 99% or less than 100% amino acid sequence identity to the amino acid sequence of SEQ ID NO: 1; (iii) at least 90%, 91%, 92%, 93%, 94%, 95%, 96%, 97%, 98%, 99%, or less than 100% amino acid sequence identity to the amino acid sequence of SEQ ID NO: 1.

In an even still further embodiment, one or more subtilisin variant described herein has one or more improved property when compared to a reference or parent subtilisin (e.g. a subtilisin having the amino acid sequence of SEQ ID NO: 1); wherein the improved property is selected from improved cleaning performance in detergents, improved stability; and combinations thereof. In another embodiment, parent subtilisin comprises an amino acid sequence of SEQ ID NO: 1. In yet another embodiment, the improved property is (i) improved cleaning performance in detergent, where the variant has a BMI, crème brûlée and/or egg stain cleaning PI≥1.1; and/or (ii) improved stability, where the variant has a stability PI≥1.1. In still yet another embodiment, the cleaning performance in detergent is measured in accordance with the cleaning performance in laundry (HDD and/or HDL) and ADW detergents assay of Example 1; and/or the stability is measured in accordance with the stability assay of Example 1.

The term "enhanced stability" or "improved stability" in the context of an oxidation, chelator, denaturant, surfactant, thermal and/or pH stable protease refers to a higher retained proteolytic activity over time as compared to a reference protease, for example, a wild-type protease or parent protease (e.g. a protease having the amino acid sequence of SEQ ID NO: 1). Autolysis has been identified as one mode of subtilisin activity loss in liquid detergents. (Stoner et al., 2004 Protease autolysis in heavy-duty liquid detergent formulations: effects of thermodynamic stabilizers and protease inhibitors, Enzyme and Microbial Technology 34:114-125.).

The terms "thermally stable" and "thermostable" and "thermostability" with regard to a protease variant refers to a protease that retains a specified amount of enzymatic activity after exposure to altered temperatures over a given period of time under conditions (or "stress conditions") prevailing during proteolytic, hydrolysing, cleaning or other process. "Altered temperatures" encompass increased or decreased temperatures.

In some embodiments, the variant proteases provided herein retain at least about 40%, about 50%, about 60%, about 70%, about 80%, about 85%, about 90%, about 92%, about 95%, about 96%, about 97%, about 98%, or about 99% proteolytic activity after exposure to temperatures of 50° C., 51° C., 52° C., 53° C., 54° C., 55° C., 56° C., 57° C., 58° C., 58° C., 59° C., or 60° C. over a given time period, for example, at least about 5 minutes, at least about 20 minutes, at least about 60 minutes, about 90 minutes, about 120 minutes, about 180 minutes, about 240 minutes, about 300 minutes, about 360 minutes, about 420 minutes, about 480 minutes, about 540 minutes, about 600 minutes, about 660 minutes, about 720 minutes, about 780 minutes, about 840 minutes, about 900 minutes, about 960 minutes, about 1020 minutes, about 1080 minutes, about 1140 minutes, or about 1200 minutes. In one embodiment, the variant subtilisins provided herein have a Performance Index of greater than 1 compared to the parent protease using the method set forth in Example 1.

The subtilisin variants provided herein may be used in the production of various compositions, such as enzyme compositions and cleaning or detergent compositions. An enzyme composition comprises a subtilisin variant a provided herein. The enzyme composition can be in any form, such as granule, liquid formulations, or enzyme slurries.

Enzyme granules may be made by, e.g., rotary atomization, wet granulation, dry granulation, spray drying, disc granulation, extrusion, pan coating, spheronization, drum granulation, fluid-bed agglomeration, high-shear granulation, fluid-bed spray coating, crystallization, precipitation, emulsion gelation, spinning disc atomization and other casting approaches, and prilling processes. The core of the granule may be the granule itself or the inner nucleus of a layered granule.

The core may comprise one or more water soluble or dispersible agent(s), including but not limited to, sodium sulfate, sodium chloride, magnesium sulfate, zinc sulfate, and ammonium sulfate), citric acid, sugars (e.g., sucrose, lactose, glucose, granulated sucrose, maltodextrin and fructose), plasticizers (e.g., polyols, urea, dibutyl phthalate, and dimethyl phthalate), fibrous material (e.g., cellulose and cellulose derivatives such as hydroxyl-propyl-methyl cellulose, carboxy-methyl cellulose, and hydroxyl-ethyl cellulose), phosphate, calcium, a protease inhibitor and combinations thereof. Suitable dispersible agents include, but are not limited to, clays, nonpareils (combinations of sugar and starch; e.g., starch-sucrose non-pareils-ASNP), talc, silicates, carboxymethyl cellulose, starch, and combinations thereof.

In some embodiments, the core comprises mainly sodium sulfate. In some embodiments, the core consists essentially of sodium sulfate. In a particular embodiment, the core consists of only sodium sulfate.

In some embodiments, the core comprises a subtilisin variant as provided herein. In other embodiments, the core comprises one or more enzymes in addition to protease. In other embodiments, the core is inert and does not comprise enzymes.

In some embodiments, the core is an enzyme powder, including UFC containing an enzyme. The enzyme powder may be spray dried and may optionally be admixed with any of the water soluble or dispersible agents listed, herein. The enzyme may be, or may include, the protease to be stabilized, in which case the enzyme power should further include a stabilizer.

In some embodiments, the core is coated with at least one coating layer. In a particular embodiment, the core is coated with at least two coating layers. In another particular embodiment, the core is coated with at least three coating layers. The materials used in the coating layer(s) can be suitable for use in cleaning and/or detergent compositions.

In some embodiments, a coating layer comprises one of more of the following materials: an inorganic salt (e.g., sodium sulfate, sodium chloride, magnesium sulfate, zinc sulfate, and ammonium sulfate), citric acid, a sugar (e.g., sucrose, lactose, glucose, and fructose), a plasticizer (e.g., polyols, urea, dibutyl phthalate, and dimethyl phthalate), fibrous material (e.g., cellulose and cellulose derivatives such as hydroxyl-propyl-methyl cellulose, carboxy-methyl cellulose, and hydroxyl-ethyl cellulose), clay, nonpareil (a combination of sugar and starch), silicate, carboxymethyl cellulose, phosphate, starch (e.g., com starch), fats, oils (e.g., rapeseed oil, and paraffin oil), lipids, vinyl polymers, vinyl copolymers, polyvinyl alcohol (PVA), plasticizers (e.g., polyols, urea, dibutyl phthalate, dimethyl phthalate, and water), anti-agglomeration agents (e.g., talc, clays, amorphous silica, and titanium dioxide), anti-foam agents (such as FOAMBLAST 882® and EROL 6000K®), and talc.

US20100124586, WO9932595, and U.S. Pat. No. 5,324,649 detail suitable components for the coating layers.

In some embodiments, the coating layer comprises sugars (e.g., sucrose, lactose, glucose, granulated sucrose, maltodextrin and fructose). In some embodiments, the coating layer comprises a polymer such as polyvinyl alcohol (PVA). Suitable PVA for incorporation in the coating layer(s) of the multi-layered granule include partially hydrolyzed, fully hydrolyzed and intermediately hydrolyzed having low to high degrees of viscosity. In some embodiments, the coating layer comprises an inorganic salt, such as sodium sulfate.

In some embodiments, at least one coating layer is an enzyme coating layer. In some embodiments, the core is coated with at least two enzyme layers. In another embodiment, the core is coated with at least three or more enzyme layers.

In some embodiments, the enzymes are protease in combination with one or more additional enzymes selected from the group consisting of acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, metalloproteases, nucleases (e.g. DNases and/or RNases), oxidases, oxidoreductases, pectate lyases, pectin acetyl esterases, pectinases, pentosanases, perhydrolases, peroxidases, phenoloxidases, phosphatases, phospholipases, phytases, polygalacturonases, polyesterases, additional proteases, pullulanases, reductases, rhamnogalacturonases, beta-glucanases, tannases, transglutaminases, xylan acetylesterases, xylanases, xyloglucanases, xylosidases, and any combination or mixture thereof. Generally, at least one enzyme coating layer comprises at least one protease.

The above enzyme lists are examples only and are not meant to be exclusive. Any enzyme can be used in the granules described herein, including wild type, recombinant and variant enzymes of bacterial, fungal, yeast, sources, and acid, neutral or alkaline enzymes.

A further embodiment is directed to a method of cleaning a proteinaceous stain or a crème brûlée stain comprising contacting a surface or an item in need of cleaning using an automatic dishwashing (ADW) composition with an effective amount of one or more subtilisin variant or ADW composition containing one or more subtilisin variant, wherein said variant comprises an amino acid sequence having a glutamate at a position corresponding to position 39 of SEQ ID NO: 1 and further comprising one or more substitutions selected from: X009A/C/E/M/N/Y, X010A/K/M/N/Q/W, X011A/T, X012A/C/D/E/M, X014D, X015D/E/H/I/M/V/W/Y, X016L/M, X017C/E, X018C/D/E/M, X019A/C/D/E/F/H/I/K/L/N/Q/S/T/W/Y, X020C/D, X024A/E, X025A/C/D/E/M/N, X026A, X027K, X036C/E/Q/V, X042C/D/E, X043L, X044C/E/G/H/I/L/N/Q/S/T, X052A/C/D/L/M/N, X054A/C/L/M/V, X055A/C/D/E/M, X057D/E, X059A/C/D/E/M/N/Q/T, X060S, X076D/E/N, X082A, X084D, X096Q, X097E/H, X104A/D/H/N/V/Y, X115H, X116E, X128G, X129H, X131D/E, X135A/E/F/H/I/K/L/M/S/T/V/W/Y, X139E, X141E, X142D/E, X143E, X144E, X147C, X148L, X154D, X156A/C/D/N/T, X157C/D/E, X158C/L/Q/T/Y, X159L, X164A/K/M/Q/Y, X166D/E, X167E, X169L, X174V, X176A/C/D/E/N, X177C/D/E, X178D, X179A/C/E/F/G/H/I/K/M/Q/S/V/W/Y, X180K, X182C/D/E, X188C/D/E, X189C/D/E, X193A/M, X198D/E, X207K/L/N/Q/T, X209P, X210C/D/E/L/N/Y, X211E/K/L/Q, X212C/Q, X228L, X230E, X231C/E/L/N/Q, X232F, X234D/E/T/W/Y, X236D/T, X238A/D/E/M/V, X239D/E/M/N, X245E, X246A/L, X247E/Q, X249C/D/E/L/Y, X250D, X253D/E/P, X254Y, X255A/C/D/E, X256C/E/Y, X257C, X259D/E/M/N, X262L, X263D, X268C/D/E, and X269H/P/W and combinations thereof; where the amino acid positions of the variant are numbered by correspondence with the amino acid sequence of SEQ ID NO: 1. A still further embodiment is directed to a method of cleaning a proteinaceous or a crème brûlée stain comprising contacting a surface or an item in need of cleaning using an ADW composition with an effective amount of one or more subtilisin variant or ADW composition containing one or more subtilisin variant, wherein said variant comprises an amino acid sequence having a glutamate at a position corresponding to position 39 of SEQ ID NO: 1 and further comprising one or more substitutions selected from: X009A/C/E/M/N/Y, X010A/K/M/N/Q/W, X011A/T, X012A/C/D/E/M, X014D, X015D/E/H/I/M/V/W/Y, X016L/M, X017C/E, X018C/D/E/M, X019A/C/D/E/F/H/I/K/L/N/Q/S/T/W/Y, X020C/D, X024A/E, X025A/C/D/E/M/N, X026A, X027K, X036C/E/Q/V, X042C/D/E, X043L, X044C/E/G/H/I/L/N/Q/S/T, X052A/C/D/L/M/N, X054A/C/L/M/V, X055A/C/D/E/M, X057D/E, X059A/C/D/E/M/N/Q/T, X060S, X076D/E/N, X082A, X084D, X096Q, X097E/H, X104A/D/H/N/V/Y, X115H, X116E, X128G, X129H, X131D/E, X135A/E/F/H/I/K/L/M/S/T/V/W/Y, X139E, X141E, X142D/E, X143E, X144E, X147C, X148L, X154D, X156A/C/D/N/T, X157C/D/E, X158C/L/Q/T/Y, X159L, X164A/K/M/Q/Y, X166D/E, X167E, X169L, X174V, X176A/C/D/E/N, X177C/D/E, X178D, X179A/C/E/F/G/H/I/K/M/Q/S/V/W/Y, X180K, X182C/D/E, X188C/D/E, X189C/D/E, X193A/M, X198D/E, X207K/L/N/Q/T, X209P, X210C/D/E/L/N/Y, X211E/K/L/Q, X212C/Q, X228L, X230B, X231C/E/L/N/Q, X232F, X234D/E/T/W/Y, X236D/T, X238A/D/E/M/V, X239D/E/M/N, X24SE, X246A/L, X247E/Q, X249C/D/E/L/Y, X250D, X253D/E/P, X254Y, X255A/C/D/E, X256C/E/Y, X257C, X259D/E/M/N, X262L, X263D, X268C/D/E, and X269H/P/W and combinations thereof; where the amino acid positions of the variant are numbered by correspondence with the amino acid sequence of SEQ ID NO: 1 and where the variant has at least 80%, 85%, 90%, 91%, 92%, 93%, 94%, 95%, 96%, 97%, 98%, or 99% sequence identity to the amino acid sequence of SEQ ID NO: 1 . . .

A further embodiment is directed to a method of cleaning an egg yolk stain comprising contacting a surface or an item in need of cleaning using an ADW composition with an effective amount of one or more subtilisin variant or ADW composition containing one or more subtilisin variant, where the variant has one or more substitutions selected from: X009H/K/N/W, X011A/I, X012A/M/N/R/S/V, X015F/I/K/V, X016L/M, X017F/G/I/L/N/V/W, X018F, X019C/K/L/Q, X020A/D/M/N/T, X024A, X025A/D/N, X036A/L, X052D/H, XOS4A/G/L/M/V, XOSSA/D/H/S/Y, X059A/M/N, X060S, X069S, X076K/L, X095N, X096Q, X097K, X102L/M, X107K, X110L, X113T, X118D, X120V, X122L, X128G, X129A/H/N/Y, X131M/N/P, X136M, X143N, X144N, X145C, X157A/D, X158Q/T, X159L, X160D/M/S, X166I, X170G, X176L, X177A/D/G/K/L/M/S/Y, X179A/K, X182A/D/S/Y, X188M, X191E, X207L, X210E/G/Q, X211E/Q/R, X218S, X227M, X232F/W, X256L/Y, X263Q, X265A/M/Q, and X268A and combinations thereof; where the amino acid positions of the variant are numbered by correspondence with the amino acid sequence of SEQ ID NO: 1. A still further embodiment is directed to a method of cleaning an egg yolk stain comprising contacting a surface or an item in need of cleaning using an ADW composition with an effective amount of one or more subtilisin variant or ADW composition containing one or more subtilisin variant, wherein said variant comprises an amino acid sequence having a glutamate at a position corresponding to position 39 of SEQ ID NO: 1 and further comprising one or more substitutions selected from: X009H/K/N/W, X011A/I, X012A/M/N/R/S/V, X015F/I/K/V, X016L/M, X017F/G/I/L/N/V/W, X018F, X019C/K/L/Q, X020A/D/M/N/T, X024A, X025A/D/N, X036A/L, X052D/H, X054A/G/L/M/V, X055A/D/H/S/Y, X059A/M/N, X060S, X069S, X076K/L, X095N, X096Q, X097K, X102L/M, X107K, X110L, X113T, X118D, X120V, X122L, X128G, X129A/H/N/Y, X131M/N/P, X136M, X143N, X144N, X145C, X157A/D, X158Q/T, X159L, X160D/M/S, X166I, X170G, X176L, X177A/D/G/K/L/M/S/Y, X179A/K, X182A/D/S/Y, X188M, X191E, X207L, X210E/G/Q, X211E/Q/R, X218S, X227M, X232F/W, X256L/Y, X263Q, X265A/M/Q, and X268A and combinations thereof; where the amino acid positions of the variant are numbered by correspondence with the amino acid sequence of SEQ ID NO: 1 and where the variant has at least 80%, 85%, 90%, 91%, 92%, 93%, 94%, 95%, 96%, 97%, 98%, or 99% sequence identity to the amino acid sequence of SEQ ID NO: 1 . . .

A further embodiment is directed to a method of cleaning an article of laundry using a powder laundry detergent (HDD) composition, comprising contacting a laundry item in need of cleaning with an effective amount of one or more subtilisin variant or an HDD composition containing one or more subtilisin variant, where the variant has one or more substitutions selected from: X003V, X009Q/W, X012R/W, X015M/Q, X016M, X024A, X042M, X054N, X057M/Q, X059N, X076R, X104A, X131A/M/P/Q, X142N/Q, X144E, X145C, X147C, X157A/Q, X158A/N/Q/T, X160A, X166Q, X176A, X177Q, X186F, X190M, X211Q, X212A, X224V, X227Q, X232F/Q/R, X234A, X238A, X255N, X256M, X257M, X259M, X265M/N/Q, and X266Q/R and combinations thereof; where the amino acid positions of the variant are numbered by correspondence with the amino acid sequence of SEQ ID NO: 1. A still further embodiment is directed to a method of cleaning an article of laundry using a powder laundry detergent (HDD) composition, comprising contacting a laundry item in need of cleaning with an effective amount of one or more subtilisin variant or an HDD composition containing one or more subtilisin variant, wherein said variant comprises an amino acid sequence having a glutamate at a position corresponding to position 39 of SEQ ID NO: 1 and further comprising one or more substitutions selected from: X003V, X009Q/W, X012R/W, X015M/Q, X016M, X024A, X042M, X054N, X057M/Q, X059N, X076R, X104A, X131A/M/P/Q, X142N/Q, X144E, X145C, X147C, X157A/Q, X158A/N/T, X160A, X166Q, X176A, X177Q, X186F, X190M, X211Q, X212A, X224V, X227Q, X232F/Q/R, X234A, X238A, X255N, X256M, X257M, X259M, X265M/N/Q, and X266Q/R and combinations thereof; where the amino acid positions of the variant are numbered by correspondence with the amino acid sequence of SEQ ID NO: 1 and where the variant has at least 80%, 85%, 90%, 91%, 92%, 93%, 94%, 95%, 96%, 97%, 98%, or 99% sequence identity to the amino acid sequence of SEQ ID NO: 1 . . .

A further embodiment is directed to a method of cleaning an article of laundry using a liquid laundry (HDL) composition, comprising contacting a laundry item in need of cleaning with an effective amount of one or more subtilisin variant or an HDL composition containing one or more subtilisin variant, where the variant has one or more substitutions selected from: X008V, X011S, X012A/C/D/E/G/M/N/S/T/V, X014D, X016M, X017C/I/N/W, X018T, X019A/D/F/H/I/L/Q/S/W/Y, X024A/E, X025M/N, X042D/E/M, X044E/G/I/N/T, X052T, XOS4T/V, X055E, X059D/E, X060S, X069S, X096Q, X115E, X128G, X129H, X131D, X135E/F/H/I/S/T/V, X137L, X139E/S, X141E/H/N, X143E/H/M/N/Q/V, X156C, X157D/E, X158C/T/V, X161W, X164M/Q/Y, X166V, X167E, X176D/E/M/N/S, X177C/E, X179I/S/V/W, X182D/E/P/Q/T, X188D/E/S/V, X190M, X193M, X198D, X207K/N/T, X210D/E, X211E/Q, X231I/S, X234D, X236D, X238D, X246S, X249D, X250D/T, and X269H and combinations thereof; where the amino acid positions of the variant are numbered by correspondence with the amino acid sequence of SEQ ID NO: 1. A still further embodiment is directed to a method of cleaning an article of laundry using a liquid laundry (HDL) composition, comprising contacting a laundry item in need of cleaning with an effective amount of one or more subtilisin variant or an HDL composition containing one or more subtilisin variant, wherein said variant comprises an amino acid sequence having a glutamate at a position corresponding to position 39 of SEQ ID NO: 1 and further comprising one or more substitutions selected from: X008V, X011S. X012A/C/D/E/G/M/N/S/T/V, X014D, X016M, X017C/I/N/W, X018T, X019A/D/F/H/I/L/Q/S/W/Y, X024A/E, X025M/N, X042D/E/M, X044E/G/I/N/T, X0S2T, X054T/V, X055E, X059D/E, X060S, X069S, X096Q, X115E, X128G, X129H, X131D, X135E/F/H/I/S/T/V, X137L, X139E/S, X141E/H/N, X143E/H/M/N/Q/V, X156C, X157D/E, X158C/T/V, X161W, X164M/Q/Y, X166V, X167E, X176D/E/M/N/S, X177C/E, X179I/S/V/W, X182D/E/P/Q/T, X188D/E/S/V, X190M, X193M, X198D, X207K/N/T, X210D/E, X211E/Q, X231I/S, X234D, X236D, X238D, X246S, X249D, X250D/T, and X269H and combinations thereof; where the amino acid positions of the variant are numbered by correspondence with the amino acid sequence of SEQ ID NO: 1 and where the variant has at least 80%, 85%, 90%, 91%, 92%, 93%, 94%, 95%, 96%, 97%, 98%, or 99% sequence identity to the amino acid sequence of SEQ ID NO: 1 . . .

In an even further embodiment, the one or more subtilisin variant used in the methods of cleaning described herein comprises an amino acid sequence with 70%, 75%, 80%, 85%, 86%, 87%, 88%, 89%, 90%, 91%, 92%, 93%, 94%, 95%, 96%, 97%, 98%, 99% or less than 100% amino acid sequence identity to the amino acid sequence of SEQ ID NO: 1. In yet another embodiment, the one or more subtilisin variant used in the method of cleaning a crème brûlée stain described herein has a crème brûlée stain cleaning PI≥1.1 when compared to SEQ ID NO: 1. In still yet another embodiment, the one or more subtilisin variant used in the method of cleaning a crème brûlée stain described herein has a crème brûlée stain cleaning PI 21.1 when compared to SEQ ID NO: 1, wherein the crème brûlée stain cleaning performance of said variant is measured in accordance with the crème brûlée assay described in Example 1. Still yet another embodiment is directed to the method of cleaning a crème brûlée stain described herein, with the proviso that the one or more subtilisin used in said method comprises one or more non-naturally occurring substitutions. In yet another embodiment, the one or more subtilisin variant used in the method of cleaning an egg yolk stain described herein has an egg yolk stain cleaning PI 21.1 when compared to SEQ ID NO: 1. In still yet another embodiment, the one or more subtilisin variant used in the method of cleaning an egg yolk stain described herein has an egg yolk stain cleaning PI≥1.1 when compared to SEQ ID NO: 1, where the egg yolk stain cleaning performance of the variant is measured in accordance with the egg yolk assay described in Example 1. Still yet another embodiment is directed to the method of cleaning an egg yolk stain described herein, with the proviso that the one or more subtilisin used in said method comprises one or more non-naturally occurring substitutions. In yet another embodiment, the one or more subtilisin variant used in the method of cleaning blood-milk-ink (BMI) stain described herein has a BMI stain cleaning PI≥1.1 when compared to SEQ ID NO: 1. In still yet another embodiment, the one or more subtilisin variant used in the method of cleaning a BMI stain described herein has a BMI stain cleaning PI≥1.1 when compared to SEQ ID NO: 1, where the BMI stain cleaning performance of the variant is measured in accordance with the BMI assay described in Example 1. Still yet another embodiment is directed to the method of cleaning a BMI stain described herein, with the proviso that the one or more subtilisin used in the method comprises one or more non-naturally occurring substitutions. In a further embodiment, the one or more subtilisin variant used in the methods described herein (i) is isolated; (ii) has proteolytic activity; or (iii) comprises a combination of (i) and (ii).

In another embodiment, variants provided herein comprise one or more variants having amino acids substitutions selected from the group consisting of those listed in Table 4 having a PI≥1.1 in one or more of the cleaning assays or stability assay, including laundry, BMI, egg, crème brûlée assays or EDTA stability assay compared to a parent subtilisin having the amino acid sequence of SEQ ID NO: 1. In some embodiments, subtilisin variants having a PI≥1. 1 in one or more of the cleaning assays or stability assay, including laundry, BMI, egg, crème brûlée assays or EDTA stability assay compared to a parent subtilisin having the amino acid sequence of SEQ ID NO: 1 comprise an amino acid sequence having a glutamate residue (E) at a position corresponding to position 39 of SEQ ID NO: 1 and further comprising one or more amino acid substitutions at one or more positions selected from T003V, V004T, I008V, T009A/C/E/G/H/K/M/N/Q/S/W/Y, R010A/K/M/N/Q/W, V011A/I/S/T, Q012A/C/D/E/G/M/N/R/S/T/V/W, P014D, A015D/E/F/H/I/K/M/P/Q/V/W/Y, V016L/M/S, H017C/E/F/G/I/L/N/V/W/Y, N018A/C/D/E/F/G/L/M/Q/T, R019A/C/D/E/F/H/I/K/L/N/Q/S/T/W/Y, G020A/C/D/M/N/T, S024A/E, G025A/C/D/E/M/N, V026A/I, R027K, S033T, S036A/C/E/I/L/M/Q/T/V, N042C/D/E/M/Q, 1043L, R044C/E/F/G/H/I/K/L/N/Q/S/T/V/W/Y, A047I/Y, V050I, G052A/C/D/H/L/M/N/S/T/Y, P054A/C/G/L/M/N/T/V, T055A/C/D/E/H/M/N/S/Y, A057D/E/H/M/N/Q/T, L059A/C/D/E/M/N/Q/T, N060S, T069S, S076A/D/E/F/H/K/L/M/N/R/T/Y, V082A, P084D/F/H/Y, N085S, G095A/N, A096M/Q, N097E/H/K, S101T, V102L/M, G104A/D/H/M/N/T/V/W/Y, I105V, Q107K/M, E110L, A113T/V, T114V, N115E/H/Q, N116E/H. H118D/E/N, A120V, M122L, F128G, P129A/H/N/Y, S131A/D/E/I/M/N/P/Q/T/V, L133M, R135A/E/F/H/I/K/L/M/S/T/V/W/Y, A136M, V137L, Y139E/S, T141E/H/N, S142A/D/E/H/M/N/Q, R143E/H/M/N/Q/V, D144E/N, V145C, V147C, I148L/V, AISOM, N154D, S156A/C/D/N/T, G157A/C/D/E/N/Q, S158A/C/F/L/M/N/Q/T/V/W/Y, V159L, G160A/C/D/M/S/T, Y161W, R164A/K/M/Q/Y, A166D/E/I/P/Q/V, N167E, M169L, A170G, T174V, Q176A/C/D/E/L/M/N/S, N177A/C/D/E/G/H/K/L/M/Q/S/W/Y, N178D, R179A/C/E/F/G/H/I/K/M/Q/S/V/W/Y, R180K, N182A/C/D/E/G/H/I/K/L/P/Q/S/T/V/W/Y, Y186F, T188A/C/D/E/I/L/M/N/Q/S/V/W/Y, G189C/D/E, 1190M, D191E, 1192C/M, V193A/M, N198D/E, Q200I/H/I/K/M/V/Y, R207K/L/N/Q/T, V209P, S210C/D/E/F/G/L/N/P/Q/Y, M211E/K/L/Q/R, N212A/C/Q/S, T218C/S, A224V, L227M/Q, V228L, Q230E, R231C/E/H/I/L/N/Q/S/T, Y232F/H/Q/R/W, S234A/D/E/M/T/W/Y, N236D/G/S/T, T238A/D/E/M/V, Q239D/E/L/M/N/T, N242A, K245E, N246A/L/S, T247E/Q, T249C/D/E/F/I/L/S/Y, N250D/S/T, N253D/E/P, S254P/Y, S255A/C/D/E/F/I/M/N/V/W, Q256C/E/F/H/L/M/W/Y, F257C/M, S259D/E/M/N, V262L, N263D/Q, A264T, E265A/M/N/Q, A266L/M/N/Q/R, T268A/C/D/E, and R269H/P/W, where the amino acid positions of the variant are numbered by correspondence with the amino acid sequence of SEQ ID NO: 1.

One or more subtilisin variant described herein can be subject to various changes, such as one or more amino acid insertion, deletion, and/or substitution, either conservative or non-conservative, including where such changes do not substantially alter the enzymatic activity of the variant. Similarly, a nucleic acid of the invention can also be subject to various changes, such as one or more substitution of one or more nucleotide in one or more codon such that a particular codon encodes the same or a different amino acid, resulting in either a silent variation (e.g., when the encoded amino acid is not altered by the nucleotide mutation) or non-silent variation; one or more deletion of one or more nucleotides (or codon) in the sequence; one or more addition or insertion of one or more nucleotides (or codon) in the sequence; and/or cleavage of, or one or more truncation, of one or more nucleotides (or codon) in the sequence. Many such changes in the nucleic acid sequence may not substantially alter the enzymatic activity of the resulting encoded polypeptide enzyme compared to the polypeptide enzyme encoded by the original nucleic acid sequence. A nucleic acid sequence described herein can also be modified to include one or more codon that provides for optimum expression in an expression system (e.g., bacterial expression system), while, if desired, said one or more codon still encodes the same amino acid(s).

Described herein is one or more isolated, non-naturally occurring, or recombinant polynucleotide comprising a nucleic acid sequence that encodes one or more subtilisin variant described herein, or recombinant polypeptide or active fragment thereof. One or more nucleic acid sequence described herein is useful in recombinant production (e.g., expression) of one or more subtilisin variant described herein, typically through expression of a plasmid expression vector comprising a sequence encoding the one or more subtilisin variant described herein or fragment thereof. One embodiment provides nucleic acids encoding one or more subtilisin variant described herein, wherein the variant is a mature form having proteolytic activity. In some embodiments, one or more subtilisin variant described herein is expressed recombinantly with a homologous pro-peptide sequence. In other embodiments, one or more subtilisin variant described herein is expressed recombinantly with a heterologous pro-peptide sequence (e.g., pro-peptide sequence from B. lentus (SEQ ID NO: 10).

One or more nucleic acid sequence described herein can be generated by using any suitable synthesis, manipulation, and/or isolation techniques, or combinations thereof. For example, one or more polynucleotide described herein may be produced using standard nucleic acid synthesis techniques, such as solid-phase synthesis techniques that are well-known to those skilled in the art. In such techniques, fragments of up to 50 or more nucleotide bases are typically synthesized, then joined (e.g., by enzymatic or chemical ligation methods) to form essentially any desired continuous nucleic acid sequence. The synthesis of the one or more polynucleotide described herein can be also facilitated by any suitable method known in the art, including but not limited to chemical synthesis using the classical phosphoramidite method (See e.g., Beaucage et al. Tetrahedron Letters 22:1859-69 (1981)), or the method described in Matthes et al., EMBO J. 3:801-805 (1984) as is typically practiced in automated synthetic methods. One or more polynucleotide described herein can also be produced by using an automatic DNA synthesizer. Customized nucleic acids can be ordered from a variety of commercial sources (e.g., ATUM (DNA 2.0), Newark, CA, USA; Life Tech (GeneArt), Carlsbad, CA, USA; GenScript, Ontario, Canada; Base Clear B. V., Leiden, Netherlands; Integrated DNA Technologies, Skokie, IL, USA; Ginkgo Bioworks (Gen9), Boston, MA, USA; and Twist Bioscience, San Francisco, CA, USA). Other techniques for synthesizing nucleic acids and related principles are described by, for example, Itakura et al., Ann. Rev. Biochem. 53:323 (1984) and Itakura et al., Science 198: 1056 (1984).

Recombinant DNA techniques useful in modification of nucleic acids are well known in the art, such as, for example, restriction endonuclease digestion, ligation, reverse transcription and cDNA production, and polymerase chain reaction (e.g., PCR). One or more polynucleotide described herein may also be obtained by screening cDNA libraries using one or more oligonucleotide probes that can hybridize to or PCR-amplify polynucleotides which encode one or more subtilisin variant described herein, or recombinant polypeptide or active fragment thereof. Procedures for screening and isolating cDNA clones and PCR amplification procedures are well known to those of skill in the art and described in standard references known to those skilled in the art. One or more polynucleotide described herein can be obtained by altering a naturally occurring polynucleotide backbone (e.g., that encodes one or more subtilisin variant described herein or reference subtilisin) by, for example, a known mutagenesis procedure (e.g., site-directed mutagenesis, site saturation mutagenesis, and in vitro recombination). A variety of methods are known in the art that are suitable for generating modified polynucleotides described herein that encode one or more subtilisin variant described herein, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches.

A further embodiment is directed to one or more vector comprising one or more subtilisin variant described herein (e.g., a polynucleotide encoding one or more subtilisin variant described herein); expression vectors or expression cassettes comprising one or more nucleic acid or polynucleotide sequence described herein; isolated, substantially pure, or recombinant DNA constructs comprising one or more nucleic acid or polynucleotide sequence described herein; isolated or recombinant cells comprising one or more polynucleotide sequence described herein; and compositions comprising one or more such vector, nucleic acid, expression vector, expression cassette, DNA construct, cell, cell culture, or any combination or mixtures thereof.

Some embodiments are directed to one or more recombinant cell comprising one or more vector (e.g., expression vector or DNA construct) described herein which comprises one or more nucleic acid or polynucleotide sequence described herein. Some such recombinant cells are transformed or transfected with such at least one vector, although other methods are available and known in the art. Such cells are typically referred to as host cells. Some such cells comprise bacterial cells, including, but not limited to *Bacillus* sp. cells, such as *B. subtilis* cells. Other embodiments are directed to recombinant cells (e.g., recombinant host cells) comprising one or more subtilisin described herein.

In some embodiments, one or more vector described herein is an expression vector or expression cassette comprising one or more polynucleotide sequence described herein operably linked to one or more additional nucleic acid segments required for efficient gene expression (e.g., a promoter operably linked to one or more polynucleotide sequence described herein). A vector may include a transcription terminator and/or a selection gene (e.g., an antibiotic resistant gene) that enables continuous cultural maintenance of plasmid-infected host cells by growth in antimicrobial-containing media.

An expression vector may be derived from plasmid or viral DNA, or in alternative embodiments, contains elements of both. Exemplary vectors include, but are not limited to pC194, pJH101, pE194, pHP13 (See, Harwood and Cutting [eds.], Chapter 3, Molecular Biological Methods for *Bacillus*, John Wiley & Sons (1990); suitable replicating plasmids for *B. subtilis* include those listed on p. 92). (See also, Perego, "Integrational Vectors for Genetic Manipulations in *Bacillus subtilis*"; Sonenshein et al., [eds.]; "*Bacillus subtilis* and Other Gram-Positive Bacteria: Biochemistry, Physiology and Molecular Genetics", American Society for Microbiology, Washington, D.C. (1993), pp. 615-624); and p2JM103BBI).

For expression and production of a protein of interest (e.g., one or more subtilisin variant described herein) in a cell, one or more expression vector comprising one or more copy of a polynucleotide encoding one or more subtilisin variant described herein, and in some instances comprising multiple copies, is transformed into the cell under conditions suitable for expression of the variant. In some embodiments, a polynucleotide sequence encoding one or more subtilisin variant described herein (as well as other sequences included in the vector) is integrated into the genome of the host cell, while in other embodiments, a plasmid vector comprising a polynucleotide sequence encoding one or more subtilisin variant described herein remains as autonomous extra-chromosomal element within the cell. Some embodiments provide both extrachromosomal nucleic acid elements as well as incoming nucleotide sequences that are integrated into the host cell genome. The vectors described herein are useful for production of the one or more subtilisin variant described herein. In some embodiments, a polynucleotide construct encoding one or more subtilisin variant described herein is present on an integrating vector that enables the integration and optionally the amplification of the polynucleotide encoding the variant into the host chromosome. Examples of sites for integration are well known to those skilled in the art. In some embodiments, transcription of a polynucleotide encoding one or more subtilisin variant described herein is effectuated by a promoter that is the wild-type promoter for the parent subtilisin. In some other embodiments, the promoter is heterologous to the one or more subtilisin variant described herein, but is functional in the host cell. Exemplary promoters for use in bacterial host cells include, but are not limited to the amyE, amyQ, amyL, pstS, sacB, pSPAC, pAprE, pVeg, pHpaII promoters; the promoter of the *B. stearothermophilus* maltogenic amylase gene; the *B. amyloliquefaciens* (BAN) amylase gene; the *B. subtilis* alkaline protease gene; the *B. clausii* alkaline protease gene; the *B. pumilis* xylosidase gene; the *B. thuringiensis* cryIIIA; and the *B. licheniformis* alpha-amylase gene. Additional promoters include, but are not limited to the A4 promoter, as well as phage Lambda PR or PL promoters and the *E. coli* lac, trp or tac promoters.

One or more subtilisin variant described herein can be produced in host cells of any suitable microorganism, including bacteria and fungi. In some embodiments, one or more subtilisin variant described herein can be produced in Gram-positive bacteria. In some embodiments, the host cells are *Bacillus* spp., *Streptomyces* spp., *Escherichia* spp., *Aspergillus* spp., *Trichoderma* spp., *Pseudomonas* spp., *Corynebacterium* spp., *Saccharomyces* spp., or *Pichia* spp. In some embodiments, one or more subtilisin variant described herein is produced by *Bacillus* sp. host cells. Examples of *Bacillus* sp. host cells that find use in the production of the one or more subtilisin variant described herein include, but are not limited to *B. licheniformis, B. lentus, B. subtilis, B. amyloliquefaciens, B. brevis, B. stearothermophilus, B. alkalophilus, B. coagulans, B. circulans, B. pumilis, B. thuringiensis, B. clausii,* and *B. megaterium,* as well as other organisms within the genus *Bacillus*. In some embodiments, *B. subtilis* host cells are used to produce the variants described herein. USPNs 5,264,366 and 4,760,025 (RE 34,606) describe various *Bacillus* host strains that can be used to produce one or more subtilisin variant described herein, although other suitable strains can be used.

Several bacterial strains that can be used to produce one or more subtilisin variant described herein include non-recombinant (i.e., wild-type) *Bacillus* sp. strains, as well as variants of naturally-occurring strains and/or recombinant strains. In some embodiments, the host strain is a recombinant strain, wherein a polynucleotide encoding one or more subtilisin variant described herein has been introduced into the host. In some embodiments, the host strain is a *B. subtilis* host strain and particularly a recombinant *B. subtilis* host strain. Numerous *B. subtilis* strains are known, including, but not limited to for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211strain (See e.g., Hoch et al., Genetics 73:215-228 (1973); See also, U.S. Pat. Nos. 4,450,235; 4,302,544; and EP 0134048). The use of *B. subtilis* as an expression host cell is well known in the art (See e.g., Palva et al., Gene 19:81-87 (1982); Fahnestock and Fischer, J. Bacteriol., 165:796-804 (1986); and Wang et al., Gene 69:39-47 (1988)).

In some embodiments, the *Bacillus* host cell is a *Bacillus* sp. that includes a mutation or deletion in at least one of the following genes: degU, degS, degR and degQ. In some embodiments, the mutation is in a degU gene, and in some embodiments the mutation is degU (Hy) 32 (See e.g., Msadek et al., J. Bacteriol. 172:824-834 (1990); and Olmos et al., Mol. Gen. Genet. 253:562-567 (1997)). In some embodiments, the *Bacillus* host comprises a mutation or deletion in scoC4 (See e.g., Caldwell et al., J. Bacteriol, 183:7329-7340 (2001)); spoIIE (See e.g., Arigoni et al., Mol. Microbiol. 31:1407-1415 (1999)); and/or oppA or other genes of the opp operon (See e.g., Perego et al., Mol. Microbiol. 5:173-185 (1991)). Indeed, it is contemplated that any mutation in the opp operon that causes the same phenotype as a mutation in the oppA gene will find use in some embodiments of the altered *Bacillus* strain described herein. In some embodiments, these mutations occur alone, while in other embodiments, combinations of mutations are present. In some embodiments, an altered *Bacillus* host cell strain that can be used to produce one or more subtilisin variant described herein is a *Bacillus* host strain that already includes a mutation in one or more of the above-mentioned genes. In addition, *Bacillus* sp. host cells that comprise mutation(s) and/or deletion(s) of endogenous protease genes find use. In some embodiments, the *Bacillus* host cell comprises a deletion of the aprE and the nprE genes. In other embodiments, the *Bacillus* sp. host cell comprises a deletion of 5 protease genes, while in other embodiments the *Bacillus* sp. host cell comprises a deletion of 9 protease genes (See e.g., US 2005/0202535).

Host cells are transformed with one or more nucleic acid sequence encoding one or more subtilisin variant described herein using any suitable method known in the art. Methods for introducing a nucleic acid (e.g., DNA) into *Bacillus* cells or *E. coli* cells utilizing plasmid DNA constructs or vectors and transforming such plasmid DNA constructs or vectors into such cells are well known. In some embodiments, the plasmids are subsequently isolated from *E. coli* cells and transformed into *Bacillus* cells. However, it is not essential to use intervening microorganisms such as *E. coli*, and in some embodiments, a DNA construct or vector is directly introduced into a *Bacillus* host.

Exemplary methods for introducing one or more nucleic acid sequence described herein into *Bacillus* cells are described in, for example, Ferrari et al., "Genetics," in Harwood et al. [eds.], *Bacillus*, Plenum Publishing Corp. (1989), pp. 57-72; Saunders et al., J. Bacteriol. 157:718-726 (1984); Hoch et al., J. Bacteriol. 93:1925-1937 (1967); Mann et al., Current Microbiol. 13:131-135 (1986); Holubova, Folia Microbiol. 30:97 (1985); Chang et al., Mol. Gen. Genet. 168:11-115 (1979); Vorobjeva et al., FEMS Microbiol. Lett. 7:261-263 (1980); Smith et al., Appl. Env. Microbiol. 51:634 (1986); Fisher et al., Arch. Microbiol. 139:213-217 (1981); and McDonald, J. Gen. Microbiol. 130:203 (1984)). Indeed, such methods as transformation, including protoplast transformation and transfection, transduction, and protoplast fusion are well known and suited for use herein. Methods known in the art to transform *Bacillus* cells include such methods as plasmid marker rescue transformation, which involves the uptake of a donor plasmid by competent cells carrying a partially homologous resident plasmid (See, Contente et al., Plasmid 2:555-571 (1979); Haima et al., Mol. Gen. Genet. 223:185-191 (1990); Weinrauch et al., J. Bacteriol. 154:1077-1087 (1983); and Weinrauch et al., J. Bacteriol. 169:1205-1211 (1987)). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising a nucleic acid encoding one or more subtilisin variant described herein (i.e., an intermediate cell is not used to amplify, or otherwise process, the DNA construct or vector prior to introduction into the host cell). Introduction of a DNA construct or vector described herein into the host cell includes those physical and chemical methods known in the art to introduce a nucleic acid sequence (e.g., DNA sequence) into a host cell without insertion into the host genome. Such methods include, but are not limited to calcium chloride precipitation, electroporation, naked DNA, and liposomes. In additional embodiments, DNA constructs or vector are co-transformed with a plasmid, without being inserted into the plasmid. In further embodiments, a selective marker is deleted from the altered *Bacillus* strain by methods known in the art (See, Stahl et al., J. Bacteriol. 158:411-418 (1984); and Palmeros et al., Gene 247:255-264 (2000)).

In some embodiments, the transformed cells are cultured in conventional nutrient media. The suitable specific culture conditions, such as temperature, pH and the like are known to those skilled in the art and are well described in the scientific literature. Some embodiments provide a culture (e.g., cell culture) comprising one or more subtilisin variant or nucleic acid sequence described herein.

In some embodiments, host cells transformed with one or more polynucleotide sequence encoding one or more subtilisin variant described herein are cultured in a suitable nutrient medium under conditions permitting the expression of the variant, after which the resulting variant is recovered from the culture. In some embodiments, the variant produced by the cells is recovered from the culture medium by conventional procedures, including, but not limited to, for example, separating the host cells from the medium by centrifugation or filtration, precipitating the proteinaceous components of the supernatant or filtrate by means of a salt (e.g., ammonium sulfate), and chromatographic purification (e.g., ion exchange, gel filtration, affinity, etc.).

In some embodiments, one or more subtilisin variant produced by a recombinant host cell is secreted into the culture medium. A nucleic acid sequence that encodes a purification facilitating domain may be used to facilitate purification of the variant. A vector or DNA construct comprising a polynucleotide sequence encoding one or more subtilisin variant described herein may further comprise a nucleic acid sequence encoding a purification facilitating domain to facilitate purification of the variant (See e.g., Kroll et al., DNA Cell Biol. 12:441-53 (1993)). Such purification facilitating domains include, but are not limited to, for example, metal chelating peptides such as histidine-tryptophan modules that allow purification on immobilized metals (See, Porath, Protein Expr. Purif. 3:263-281) [1992]), protein A domains that allow purification on immobilized immunoglobulin, and the domain utilized in the FLAGS extension/affinity purification system. The inclusion of a cleavable linker sequence such as Factor XA or enterokinase (e.g., sequences available from Invitrogen, San Diego, CA) between the purification domain and the heterologous protein also find use to facilitate purification.

A variety of methods can be used to determine the level of production of one or more mature subtilisin variant described herein in a host cell. Such methods include, but are not limited to, for example, methods that utilize either polyclonal or monoclonal antibodies specific for the protease. Exemplary methods include, but are not limited to enzyme-linked immunosorbent assays (ELISA), radioimmunoassays (RIA), fluorescent immunoassays (FIA), and fluorescent activated cell sorting (FACS). These and other assays are well known in the art (See e.g., Maddox et al., J. Exp. Med. 158:1211 (1983)).

Some other embodiments provide methods for making or producing one or more mature subtilisin variant described herein. A mature subtilisin variant does not include a signal peptide or a propeptide sequence. Some methods comprise making or producing one or more subtilisin variant described herein in a recombinant bacterial host cell, such as for example, a Bacillus sp. cell (e.g., a B. subtilis cell). Other embodiments provide a method of producing one or more subtilisin variant described herein, wherein the method comprises cultivating a recombinant host cell comprising a recombinant expression vector comprising a nucleic acid sequence encoding one or more subtilisin variant described herein under conditions conducive to the production of the variant. Some such methods further comprise recovering the variant from the culture.

Further embodiments provide methods of producing one or more subtilisin variant described herein, wherein the methods comprise: (a) introducing a recombinant expression vector comprising a nucleic acid encoding the variant into a population of cells (e.g., bacterial cells, such as B. subtilis cells); and (b) culturing the cells in a culture medium under conditions conducive to produce the variant encoded by the expression vector. Some such methods further comprise: (c) isolating the variant from the cells or from the culture medium.

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. Compositions described herein include cleaning compositions, such as detergent compositions. In the exemplified detergent compositions, the enzyme levels are expressed by pure enzyme by weight of the total composition and unless otherwise specified, the detergent ingredients are expressed by weight of the total compositions.

In one embodiment, one or more subtilisin variant described herein is useful in cleaning applications, such as, for example, but not limited to, cleaning dishware or tableware items, fabrics, medical instruments and items having hard surfaces (e.g., the hard surface of a table, table top, wall, furniture item, floor, and ceiling). In other embodiments, one or more subtilisin variant described herein is useful in disinfecting applications, such as, for example, but not limited to, disinfecting an automatic dishwashing or laundry machine.

Another embodiment is directed to a composition comprising one or more subtilisin variant described herein. In some embodiments, the composition is a cleaning composition. In other embodiments, the composition is a detergent composition. In yet other embodiments, the composition is selected from a laundry detergent composition, an automatic dishwashing (ADW) composition, a hand (manual) dishwashing detergent composition, a hard surface cleaning composition, an eyeglass cleaning composition, a medical instrument cleaning composition, a disinfectant (e.g., malodor or microbial) composition, and a personal care cleaning composition. In still other embodiments, the composition is a laundry detergent composition, an ADW composition, or a hand (manual) dishwashing detergent composition. Even still further embodiments are directed to fabric cleaning compositions, while other embodiments are directed to non-fabric cleaning compositions. In some embodiments, the cleaning composition is boron-free. In other embodiments, the cleaning composition is phosphate-free. In still other embodiments, the composition comprises one or more subtilisin variant described herein and one or more of an excipient, adjunct material, and/or additional enzyme.

In yet still a further embodiment, the composition described herein contains phosphate, is phosphate-free, contains boron, is boron-free, or combinations thereof. In other embodiments, the composition is a boron-free composition. In some embodiments, a boron-free composition is a composition to which a borate stabilizer has not been added. In another embodiment, a boron-free composition is a composition that contains less than 5.5% boron. In a still further embodiment, a boron-free composition is a composition that contains less than 4.5% boron. In yet still another embodiment, a boron-free composition is a composition that contains less than 3.5% boron. In yet still a further embodiment, a boron-free composition is a composition that contains less than 2.5% boron. In even further embodiments, a boron-free composition is a composition that contains less than 1.5% boron. In another embodiment, a boron-free composition is a composition that contains less than 1.0% boron. In still further embodiments, a boron-free composition is a composition that contains less than 0.5% boron. In other embodiments, the composition is a composition free or substantially-free of enzyme stabilizers or peptide inhibitors.

In another embodiment, one or more composition described herein is in a form selected from gel, tablet, powder, granular, solid, liquid, unit dose, and combinations thereof. In yet another embodiment, one or more composition described herein is in a form selected from a low water compact formula, low water HDL or Unit Dose (UD), or high water formula or HDL. In some embodiments, the cleaning composition described herein is in a unit dose form. In other embodiments, the unit does form is selected from pills, tablets, capsules, gelcaps, sachets, pouches, multi-compartment pouches, and pre-measured powders or liquids. In some embodiments, the unit dose format is designed to provide controlled release of the ingredients within a multi-compartment pouch (or other unit dose format). Suitable unit dose and controlled release formats are described, for example, in EP 2100949; WO 02/102955; U.S. Pat. Nos. 4,765,916; 4,972,017; and WO 04/111178. In some embodiments, the unit dose form is a tablet or powder contained in a water-soluble film or pouch.

Exemplary laundry detergent compositions include, but are not limited to, for example, liquid and powder laundry detergent compositions. Exemplary hard surface cleaning compositions include, but not limited to, for example, compositions used to clean the hard surface of a non-dishware item, non-tableware item, table, table top, furniture item, wall, floor, and ceiling. Exemplary hard surface cleaning compositions are described, for example, in USPNs 6,610,642, 6,376,450, and 6,376,450. Exemplary personal care compositions include, but are not limited to, compositions used to clean dentures, teeth, hair, contact lenses, and skin. Exemplary components of such oral care composition include those described in, for example, U.S. Pat. No. 6,376,450.

In some embodiments, one or more subtilisin variant described herein cleans at low temperatures. In other embodiments, one or more composition described herein cleans at low temperatures. In other embodiments, one or more composition described herein comprises an effective amount of one or more subtilisin variant described herein as useful or effective for cleaning a surface in need of proteinaceous stain removal In some embodiments, adjunct materials are incorporated, for example, to assist or enhance cleaning performance; for treatment of the substrate to be cleaned; or to modify the aesthetics of the cleaning composition as is the case with perfumes, colorants, dyes or the like. One embodiment is directed to a composition comprising one or more adjunct material and one or more subtilisin variant described herein. Another embodiment is directed to a composition comprising one or more adjunct material and one or more subtilisin variant described herein, wherein the adjunct material is selected from a bleach catalyst, an additional enzyme, an enzyme stabilizer (including, for example, an enzyme stabilizing system), a chelant, an optical brightener, a soil release polymer, a dye transfer agent, a dispersants, a suds suppressor, a dye, a perfume, a colorant, a filler, a photoactivator, a fluorescer, a fabric conditioner, a hydrolyzable surfactant, a preservative, an anti-oxidant, an anti-shrinkage agent, an anti-wrinkle agent, a germicide, a fungicide, a color speckle, a silvercare agent, an anti-tarnish agent, an anti-corrosion agent, an alkalinity source, a solubilizing agent, a carrier, a processing aid, a pigment, a pH control agent, a surfactant, a builder, a chelating agent, a dye transfer inhibiting agent, a deposition aid, a catalytic material, a bleach activator, a bleach booster, a hydrogen peroxide, a source of hydrogen peroxide, a preformed peracid, a polymeric dispersing agent, a clay soil removal/anti-redeposition agent, a structure elasticizing agent, a fabric softener, a carrier, a hydrotrope, a processing aid, a pigment, and combinations thereof. Exemplary adjunct materials and levels of use are found in USPNs 5,576,282; 6,306,812; 6,326,348; 6,610,642; 6,605,458; 5,705,464; 5,710,115; 5,698,504; 5,695,679; 5,686,014 and 5,646,101. In embodiments in which one or more cleaning adjunct material is not compatible with one or more subtilisin variant described herein, methods are employed to keep the adjunct material and variant(s) separated (i.e., not in contact with each other) until combination of the two components is appropriate. Such separation methods include any suitable method known in the art (e.g., gelcaps, encapsulation, tablets, physical separation, etc.).

Some embodiments are directed to cleaning additive products comprising one or more subtilisin variant described herein. In some embodiments, the additive is packaged in a dosage form for addition to a cleaning process. In some embodiments, the additive is packaged in a dosage form for addition to a cleaning process where a source of peroxide is employed and increased bleaching effectiveness is desired.

Exemplary fillers or carriers for granular compositions include, but are not limited to, for example, various salts of sulfate, carbonate and silicate; talc; and clay. Exemplary fillers or carriers for liquid compositions include, but are not limited to, for example, water or low molecular weight primary and secondary alcohols including polyols and diols (e.g., methanol, ethanol, propanol and isopropanol). In some embodiments, the compositions contain from about 5% to about 90% of such filler or carrier. Acidic fillers may be included in such compositions to reduce the pH of the resulting solution in the cleaning method or application.

In one embodiment, one or more cleaning composition described herein comprises an effective amount of one or more subtilisin variant described herein, alone or in combination with one or more additional enzyme. Typically, a cleaning composition comprises at least about 0.0001 to about 20 wt %, from about 0.0001 to about 10 wt %, from about 0.0001 to about 1 wt %, from about 0.001 to about 1 wt %, or from about 0.01 to about 0.1 wt % of one or more protease. In another embodiment, one or more cleaning composition described herein comprises from about 0.01 to about 10 mg, about 0.01 to about 5 mg, about 0.01 to about 2 mg, about 0.01 to about 1 mg, about 0.05 to about 1 mg, about 0.5 to about 10 mg, about 0.5 to about 5 mg, about 0.5 to about 4 mg, about 0.5 to about 3 mg, about 0.5 to about 2 mg, about 0.5 to about 1 mg, about 0.1 to about 10 mg, about 0.1 to about 5 mg, about 0.1 to about 4 mg, about 0.1 to about 3 mg, about 0.1 to about 2 mg, about 0.1 to about 2 mg, about 0.1 to about 1 mg, or about 0.1 to about 0.5 mg of one or more protease per gram of composition.

The cleaning compositions described herein are typically formulated such that during use in aqueous cleaning operations, the wash water will have a pH of from about 4.0 to about 11.5, or even from about 5.0 to about 11.5, or even from about 5.0 to about 8.0, or even from about 7.5 to about 10.5. Liquid product formulations are typically formulated to have a pH from about 3.0 to about 9.0 or even from about 3 to about 5. Granular laundry products are typically formulated to have a pH from about 8 to about 11. In some embodiments, the cleaning compositions of the present invention can be formulated to have an alkaline pH under wash conditions, such as a pH of from about 8.0 to about 12.0, or from about 8.5 to about 11.0, or from about 9.0 to about 11.0. In some embodiments, the cleaning compositions of the present invention can be formulated to have a neutral pH under wash conditions, such as a pH of from about 5.0 to about 8.0, or from about 5.5 to about 8.0, or from about 6.0 to about 8.0, or from about 6.0 to about 7.5. In some embodiments, the neutral pH conditions can be measured when the cleaning composition is dissolved 1:100 (wt:wt) in de-ionised water at 20° C., measured using a conventional pH meter. Techniques for controlling pH at recommended usage levels include the use of buffers, alkalis, acids, etc., and are well known to those skilled in the art.

In some embodiments, one or more subtilisin variant described herein is encapsulated to protect it during storage from the other components in the composition and/or control the availability of the variant during cleaning. In some embodiments, encapsulation enhances the performance of the variant and/or additional enzyme. In some embodiments, the encapsulating material typically encapsulates at least part of the subtilisin variant described herein. Typically, the encapsulating material is water-soluble and/or water-dispersible. In some embodiments, the encapsulating material has a glass transition temperature (Tg) of 0° C. or higher. Exemplary encapsulating materials include, but are not limited to, carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some embodiments, the encapsulating material is a starch (See e.g., EP0922499, U.S. Pat. Nos. 4,977,252, 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof. Exemplary commercial microspheres include, but are not limited to EXPANCEL® (Stockviksverken, Sweden); and PM 6545, PM 6550, PM 7220, PM 7228, EXTENDOSPHERES®, LUXSIL®, Q-CEL®, and SPHERICEL® (PQ Corp., Valley Forge, PA).

There are a variety of wash conditions including varying detergent formulations, wash water volumes, wash water temperatures, and lengths of wash time to which one or more subtilisin variant described herein may be exposed. A low detergent concentration system is directed to wash water containing less than about 800 ppm detergent components. A medium detergent concentration system is directed to wash containing between about 800 ppm and about 2000 ppm detergent components. A high detergent concentration system is directed to wash water containing greater than about 2000 ppm detergent components. In some embodiments, the "cold water washing" of the present invention utilizes "cold water detergent" suitable for washing at temperatures from about 10° C. to about 40° C., from about 20° C. to about 30° C., or from about 15° C. to about 25° C., as well as all other combinations within the range of about 15° C. to about 35° C. or 10° C. to 40° C.

Different geographies have different water hardness. Hardness is a measure of the amount of calcium ($Ca^{2+}$) and magnesium ($Mg^{2+}$) in the water. Water hardness is usually described in terms of the grains per gallon (gpg) mixed $Ca^{2+}/Mg^{2+}$. Most water in the United States is hard, but the degree of hardness varies. Moderately hard (60-120 ppm) to hard (121-181 ppm) water has 60 to 181 ppm (ppm can be converted to grains per U.S. gallon by dividing ppm by 17.1) of hardness minerals.

| Water | Grains per gallon | Parts per million |
| --- | --- | --- |
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

Other embodiments are directed to one or more cleaning composition comprising from about 0.00001% to about 10% by weight composition of one or more subtilisin variant described herein and from about 99.999% to about 90.0% by weight composition of one or more adjunct material. In another embodiment, the cleaning composition comprises from about 0.0001% to about 10%, about 0.001% to about 5%, about 0.001% to about 2%, or about 0.005% to about 0.5% by weight composition of one or more subtilisin variant and from about 99.9999% to about 90.0%, about 99.999% to about 98%, about 99.995% to about 99.5% by weight composition of one or more adjunct material.

In other embodiments, the composition described herein comprises one or more subtilisin variant described herein and one or more additional enzyme. The one or more additional enzyme is selected from acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, metalloproteases, nucleases (e.g. DNases and/or RNases), oxidases, oxidoreductases, pectate lyases, pectin acetyl esterases, pectinases, pentosanases, perhydrolases, peroxidases, phenoloxidases, phosphatases, phospholipases, phytases, polygalacturonases, polyesterases, additional proteases, pullulanases, reductases, rhamnogalacturonases, beta-glucanases, tannases, transglutaminases, xylan acetylesterases, xylanases, xyloglucanases, xylosidases, and any combination or mixture thereof. Some embodiments are directed to a combination of enzymes (i.e., a "cocktail") comprising conventional enzymes like amylase, lipase, cutinase, mannanase and/or cellulase in conjunction with one or more subtilisin variant described herein and/or one or more additional protease.

In another embodiment, one or more composition described herein comprises one or more subtilisin variant described herein and one or more additional protease. In one embodiment, the additional protease is a serine protease. In another embodiment, the additional protease is a metalloprotease, a fungal subtilisin, or an alkaline microbial protease or a trypsin-like protease. Suitable additional proteases include those of animal, vegetable or microbial origin. In some embodiments, the additional protease is a microbial protease. In other embodiments, the additional protease is a chemically or genetically modified mutant. In another embodiment, the additional protease is subtilisin like protease or a trypsin-like protease. In other embodiments, the additional protease does not contain cross-reactive epitopes with the variant as measured by antibody binding or other assays available in the art. Exemplary subtilisin proteases include those derived from for example, *Bacillus* (e.g., e.g., BPN', Carlsberg, subtilisin 309, subtilisin 147, and subtilisin 168), or fungal origin, such as, for example, those described in U.S. Pat. No. 8,362,222. Exemplary additional proteases include but are not limited to those described in WO92/21760, WO95/23221, WO2008/010925, WO09/149200, WO09/149144, WO09/149145, WO 10/056640, WO10/056653, WO2010/0566356, WO11/072099, WO2011/13022, WO11/140364, WO 12/151534, WO2015/038792, WO2015/089447, WO2015/089441, WO 2017/215925, US Publ. No. 2008/0090747, U.S. Pat. Nos. 5,801,039, 5,340,735, 5,500,364, 5,855,625, RE 34,606, U.S. Pat. Nos. 5,955,340, 5,700,676 6,312,936, 6,482,628, 8,530,219, U.S. Provisional Appl Nos. 62/180,673 and 62/161,077, and PCT Appl Nos. PCT/US2015/021813, PCT/US2015/055900, PCT/US2015/057497, PCT/US2015/057492, PCT/US2015/057512, PCT/US2015/057526, PCT/US2015/057520, PCT/US2015/057502, PCT/US2016/022282, and PCT/US16/32514, as well as metalloproteases described in WO1999014341, WO1999033960, WO1999014342, WO1999034003, WO2007044993, WO2009058303, WO 2009058661, WO2014071410, WO2014194032, WO2014194034, WO 2014194054, and WO 2014/194117. Exemplary additional proteases include, but are not limited to trypsin (e.g., of porcine or bovine origin) and the *Fusarium* protease described in WO89/06270. Exemplary commercial proteases include, but are not limited to MAX-ATASE®. MAXACAL™, MAXAPEM™, OPTICLEAN®, OPTIMASE®, PROPERASE®, PURAFECT®, PURAFECT® OXP, PURAMAX™, EXCELLASE™, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (DuPont); ALCALASE®, BLAZE®, BLAZE® variants, BLAZE® EVITY®, BLAZE® EVITY® 16L, CORONASE® SAVINASE®, SAVINASE® ULTRA, SAVINASE® EVITY®, SAVINASE® EVERIS® PRIMASE®, DURAZYM™, POLARZYME®, OVOZYME®, KANNASE®, LIQUANASE®, LIQUANASE EVERIS®, NEUTRASE®, PROGRESS UNO®, RELASE®, and ESPERASE® (Novozymes); BLAP™ and BLAP™ variants (Henkel); LAVERGY™ PRO 104 L (BASF), KAP (*B. alkalophilus* subtilisin (Kao)) and BIOTOUCH® (AB Enzymes).

Another embodiment is directed to a composition comprising one or more subtilisin variant described herein and one or more lipase. In some embodiments, the composition comprises from about 0.00001% to about 10%, about 0.0001% to about 10%, about 0.001% to about 5%, about 0.001% to about 2%, or about 0.005% to about 0.5% lipase by weight composition. An exemplary lipase can be a chemically or genetically modified mutant. Exemplary lipases include, but are not limited to, e.g., those of bacterial or fungal origin, such as, e.g., *H. lanuginosa* lipase (see, e.g., EP 258068 and EP 305216), *T. lanuginosa* lipase (see, e.g., WO 2014/059360 and WO2015/010009), *Rhizomucor miehei* lipase (see, e.g., EP 238023), *Candida* lipase, such as *C. antarctica* lipase (e.g., *C. antarctica* lipase A or B) (see, e.g., EP 214761), *Pseudomonas* lipases such as *P. alcaligenes* and *P. pseudoalcaligenes* lipase (see, e.g., EP 218272), *P. cepacia* lipase (see, e.g., EP 331376), *P. stutzeri* lipase (see, e.g., GB 1,372,034), *P. fluorescens* lipase, *Bacillus* lipase (e.g., *B. subtilis* lipase (Dartois et al., Biochem. Biophys. Acta 1131: 253-260 (1993)), *B. stearothermophilus* lipase (see, e.g., JP 64/744992), and *B. pumilus* lipase (see, e.g., WO 91/16422)). Exemplary cloned lipases include, but are not limited to *Penicillium camembertii* lipase (See, Yamaguchi et al., Gene 103:61-67 (1991)), *Geotrichum candidum* lipase (See, Schimada et al., J. Biochem., 106:383-388 (1989)), and various *Rhizopus* lipases, such as, *R. delemar* lipase (See, Hass et al., Gene 109:117-113 (1991)), *R. niveus* lipase (Kugimiya et al., Biosci. Biotech. Biochem. 56:716-719 (1992)) and *R. oryzae* lipase. Other lipolytic enzymes, such as cutinases, may also find use in one or more composition described herein, including, but not limited to, e.g., cutinase derived from *Pseudomonas mendocina* (see, WO 88/09367) and/or *Fusarium solani pisi* (see, WO90/09446). Exemplary commercial lipases include, but are not limited to MI LIPASE™, LUMA FAST™, and LIPOMAX™ (DuPont); LIPEX®, LIPOCLEAN®, LIPOLASE® and LIPOLASE® ULTRA (Novozymes); and LIPASE P™ (Amano Pharmaceutical Co. Ltd).

A still further embodiment is directed to a composition comprising one or more subtilisin variant described herein and one or more amylase. In one embodiment, the composition comprises from about 0.00001% to about 10%, about 0.0001% to about 10%, about 0.001% to about 5%, about 0.001% to about 2%, or about 0.005% to about 0.5% amylase by weight composition. Any amylase (e.g., alpha and/or beta) suitable for use in alkaline solutions may be useful to include in such composition. An exemplary amylase can be a chemically or genetically modified mutant. Exemplary amylases include, but are not limited to those of bacterial or fungal origin, such as, for example, amylases described in GB 1,296,839, WO9100353, WO9402597, WO94183314, WO9510603, WO9526397, WO9535382, WO9605295, WO9623873, WO9623874, WO 9630481, WO9710342, WO9741213, WO9743424, WO9813481, WO 9826078, WO9902702, WO 9909183, WO9919467, WO9923211, WO9929876, WO9942567, WO 9943793, WO9943794, WO 9946399, WO0029560, WO0060058, WO0060059, WO0060060, WO 0114532, WO0134784, WO 0164852, WO0166712, WO0188107, WO0196537, WO02092797, WO 0210355, WO0231124, WO 2004055178, WO2004113551, WO2005001064, WO2005003311, WO 2005018336, WO2005019443, WO2005066338, WO2006002643, WO2006012899, WO2006012902, WO2006031554, WO 2006063594, WO2006066594, WO2006066596, WO2006136161, WO 2008000825, WO2008088493, WO2008092919, WO2008101894, WO2008/112459, WO2009061380, WO2009061381, WO 2009100102, WO2009140504, WO2009149419, WO 2010/059413, WO 2010088447, WO2010091221, WO2010104675, WO2010115021, WO10115028, WO2010117511, WO 2011076123, WO2011076897, WO2011080352, WO2011080353, WO 2011080354, WO2011082425, WO2011082429, WO 2011087836, WO2011098531, WO2013063460, WO2013184577, WO 2014099523, WO2014164777, and WO2015077126. Exemplary commercial amylases include, but are not limited to AMPLIFY®, DURAMYL®, TERMAMYL®, FUNGAMYL®, STAINZYME®, STAINZYME PLUS®, STAINZYME PLUS®, STAINZYME ULTRA® EVITY®, and BAN™ (Novozymes); EFFECTENZ™ S 1000, POWERASE™, PREFERENZ™ S 100, PREFERENZ™ S 110, EXCELLENZ™ S 2000, RAPIDASER and MAXAMYL® P (DuPont).

Yet a still further embodiment is directed to a composition comprising one or more subtilisin variant described herein and one or more cellulase. In one embodiment, the composition comprises from about 0.00001% to about 10%, 0.0001% to about 10%, about 0.001% to about 5%, about 0.001% to about 2%, or about 0.005% to about 0.5% cellulase by weight of composition. Any suitable cellulase may find use in a composition described herein. An exemplary cellulase can be a chemically or genetically modified mutant. Exemplary cellulases include but are not limited, to those of bacterial or fungal origin, such as, for example, those described in WO2005054475, WO2005056787, U.S. Pat. Nos. 7,449,318, 7,833,773, 4,435,307; EP 0495257; and U.S. Provisional Appl. No. 62/296,678. Exemplary commercial cellulases include, but are not limited to, CELLUCLEAN®, CELLUZYME®, CAREZYME®, ENDOLASE®, RENOZYME®, and CAREZYME® PREMIUM (Novozymes); REVITALENZ™ 100, REVITALENZ™ 200/220, and REVITALENZ® 2000 (DuPont); and KAC-500 (B)™ (Kao Corporation). In some embodiments, cellulases are incorporated as portions or fragments of mature wild-type or variant cellulases, wherein a portion of the N-terminus is deleted (see, e.g., U.S. Pat. No. 5,874,276).

An even still further embodiment is directed to a composition comprising one or more subtilisin variant described herein and one or more mannanase. In one embodiment, the composition comprises from about 0.00001% to about 10%, about 0.0001% to about 10%, about 0.001% to about 5%, about 0.001% to about 2%, or about 0.005% to about 0.5% mannanase by weight composition. An exemplary mannanase can be a chemically or genetically modified mutant. Exemplary mannanases include, but are not limited to, those of bacterial or fungal origin, such as, for example, those described in WO 2016/007929; USPNs 6,566,114; 6,602,842; and 6,440,991; and U.S. Provisional Appl. Nos. 62/251,516, 62/278,383, and 62/278387. Exemplary commercial mannanases include, but are not limited to MANNAWAY® (Novozymes) and EFFECTENZ™ M 1000, EFFECTENZ™ M 2000, PREFERENZ® M 100, MANNASTAR®, and PURABRITE™ (DuPont).

A yet even still further embodiment is directed to a composition comprising one or more subtilisin variant described herein and one or more peroxidase and/or oxidase enzyme. In one embodiment, the composition comprises from about 0.00001% to about 10%, about 0.0001% to about 10%, about 0.001% to about 5%, about 0.001% to about 2%, or about 0.005% to about 0.5% peroxidase or oxidase by weight composition. A peroxidase may be used in combination with hydrogen peroxide or a source thereof (e.g., a percarbonate, perborate or persulfate) and an oxidase may be used in combination with oxygen. Peroxidases and oxidases are used for "solution bleaching" (i.e., to prevent transfer of a textile dye from a dyed fabric to another fabric when the fabrics are washed together in a wash liquor), alone or in combination with an enhancing agent (see, e.g., WO94/12621 and WO95/01426). An exemplary peroxidase and/or oxidase can be a chemically or genetically modified mutant. Exemplary peroxidases/oxidases include, but are not limited to those of plant, bacterial, or fungal origin.

Another embodiment is directed to a composition comprising one or more subtilisin variant described herein, and one or more perhydrolase, such as, for example, is described in WO2005/056782, WO2007/106293, WO 2008/063400, WO2008/106214, and WO2008/106215.

In yet another embodiment, the one or more subtilisin variant described herein and one or more additional enzyme contained in one or more composition described herein may each independently range to about 10% by weight composition, wherein the balance of the cleaning composition is one or more adjunct material.

In some embodiments, one or more composition described herein finds use as a detergent additive, wherein said additive is in a solid or liquid form. Such additive products are intended to supplement and/or boost the performance of conventional detergent compositions and can be added at any stage of the cleaning process. In some embodiments, the density of the laundry detergent composition ranges from about 400 to about 1200 g/liter, while in other embodiments it ranges from about 500 to about 950 g/liter of composition measured at 20° C.

Some embodiments are directed to a laundry detergent composition comprising one or more subtilisin variant described herein and one or more adjunct material selected from surfactants, enzyme stabilizers, builder compounds, polymeric compounds, bleaching agents, additional enzymes, suds suppressors, dispersants, lime-soap dispersants, soil suspension agents, anti-redeposition agents, corrosion inhibitors, and combinations thereof. In some embodiments, the laundry compositions also contain softening agents.

Further embodiments are directed to manual dishwashing composition comprising one or more subtilisin variant described herein and one or more adjunct material selected from surfactants, organic polymeric compounds, suds enhancing agents, group II metal ions, solvents, hydrotropes, and additional enzymes.

Other embodiments are directed to one or more composition described herein, wherein said composition is a compact granular fabric cleaning composition that finds use in laundering colored fabrics or provides softening through the wash capacity, or is a heavy duty liquid (HDL) fabric cleaning composition. Exemplary fabric cleaning compositions and/or processes for making are described in USPNs 6,610,642 and 6,376,450. Other exemplary cleaning compositions are described, for example, in USPNs 6,605,458; 6,294,514; 5,929,022; 5,879,584; 5,691,297; 5,565,145; 5,574,005; 5,569,645; 5,565,422; 5,516,448; 5,489,392; and U.S. Pat. Nos. 5,486,303; 4,968,451; 4,597,898; 4,561,998; 4,550,862; 4,537,706; 4,515,707; and 4,515,705.

In some embodiments, the cleaning compositions comprise an acidifying particle or an amino carboxylic builder. Examples of an amino carboxylic builder include aminocarboxylic acids, salts and derivatives thereof. In some embodiment, the amino carboxylic builder is an aminopolycarboxylic builder, such as glycine-N,N-diacetic acid or derivative of general formula $MOOC-CHR-N(CH_2COOM)_2$ where R is $C_{1-12}$alkyl and M is alkali metal. In some embodiments, the amino carboxylic builder can be methylglycine diacetic acid (MGDA), GLDA (glutamic-N,N-diacetic acid), iminodisuccinic acid (IDS), carboxymethyl inulin and salts and derivatives thereof, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), IDS (iminodiacetic acid) and salts and derivatives thereof such as N-methyliminodiacetic acid (MIDA), alpha-alanine-N,N-diacetic acid (alpha-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts and derivative thereof. In some embodiments, the acidifying particle has a weight geometric mean particle size of from about 400p to about 1200u and a bulk density of at least 550 g/L. In some embodiments, the acidifying particle comprises at least about 5% of the builder.

In some embodiments, the acidifying particle can comprise any acid, including organic acids and mineral acids. Organic acids can have one or two carboxyls and in some instances up to 15 carbons, especially up to 10 carbons, such as formic, acetic, propionic, capric, oxalic, succinic, adipic, maleic, fumaric, sebacic, malic, lactic, glycolic, tartaric and glyoxylic acids. In some embodiments, the acid is citric acid. Mineral acids include hydrochloric and sulphuric acid. In some instances, the acidifying particle is a highly active particle comprising a high level of amino carboxylic builder. Sulphuric acid has also been found to further contribute to the stability of the final particle.

Additional embodiments are directed to a cleaning composition comprising one or more subtilisin variant and one or more surfactant and/or surfactant system, wherein the surfactant is selected from nonionic surfactants, anionic surfactants, cationic surfactants, ampholytic surfactants, zwitterionic surfactants, semi-polar nonionic surfactants, and mixtures thereof. In some embodiments, the surfactant is present at a level of from about 0.1 to about 60%, while in alternative embodiments the level is from about 1 to about 50%, while in still further embodiments the level is from about 5 to about 40%, by weight of the cleaning composition.

In some embodiments, one or more composition described herein comprises one or more detergent builders or builder systems. In one embodiment, the composition comprises from at least about 0.1% or greater, or from about 0.1% to about 90%, from about 0.1% to about 80%, from about 3% to about 60%, from about 5% to about 40%, or from about 10% to about 50% builder by weight composition. Exemplary builders include, but are not limited to alkali metal; ammonium and alkanolammonium salts of polyphosphates; alkali metal silicates; alkaline earth and alkali metal carbonates; aluminosilicates; polycarboxylate compounds; ether hydroxypolycarboxylates; copolymers of maleic anhydride with ethylene or vinyl methyl ether, 1, 3, 5-trihydroxy benzene-2, 4, 6-trisulphonic acid, and carboxymethyloxysuccinic acid; ammonium and substituted ammonium salts of polyacetic acids such as ethylenediamine tetraacetic acid and nitrilotriacetic acid; polycarboxylates such as mellitic acid, succinic acid, citric acid, oxydisuccinic acid, polymaleic acid, benzene 1,3,5-tricarboxylic acid, carboxymethyloxysuccinic acid; and soluble salts thereof. In some such compositions, the builders form water-soluble hardness ion complexes (e.g., sequestering builders), such as citrates and polyphosphates, e.g., sodium tripolyphosphate, sodium tripolyphospate hexahydrate, potassium tripolyphosphate, and mixed sodium and potassium tripolyphosphate. Exemplary builders are described in, o.g., EP 2100949. In some embodiments, the builders include phosphate builders and non-phosphate builders. In some embodiments, the builder is a phosphate builder. In some embodiments, the builder is a non-phosphate builder. In some embodiments, the builder comprises a mixture of phosphate and non-phosphate builders. Exemplary phosphate builders include, but are not limited to mono-phosphates, di-phosphates, tri-polyphosphates or oligomeric-polyphosphates, including the alkali metal salts of these compounds, including the sodium salts. In some embodiments, a builder can be sodium tripolyphosphate (STPP). Additionally, the composition can comprise carbonate and/or citrate. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above-mentioned compounds include the ammonium and/or alkali metal salts, i.e. the lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

In some embodiments, one or more composition described herein comprises one or more chelating agent. In one embodiment, the composition comprises from about 0.1% to about 15% or about 3% to about 10% chelating agent by weight composition. Exemplary chelating agents include, but are not limited to, e.g., copper, iron, manganese, and mixtures thereof.

In some embodiments, one or more composition described herein comprises one or more deposition aid. Exemplary deposition aids include, but are not limited to, e.g., polyethylene glycol; polypropylene glycol; polycarboxylate; soil release polymers, such as, e.g., polyterephthalic acid; clays such as, e.g., kaolinite, montmorillonite, attapulgite, illite, bentonite, and halloysite; and mixtures thereof.

In other embodiments, one or more composition described herein comprises one or more anti-redeposition agent or non-ionic surfactant (which can prevent the redeposition of soils) (see, e.g., EP 2100949). For example, in ADW compositions, non-ionic surfactants find use for surface modification purposes, in particular for sheeting, to avoid filming and spotting and to improve shine. These non-ionic surfactants also find use in preventing the re-deposition of soils. In some embodiments, the non-ionic surfactant can be ethoxylated nonionic surfactants, epoxy-capped poly (oxyalkylated) alcohols and amine oxides surfactants.

In some embodiments, one or more composition described herein comprises one or more dye transfer inhibiting agent. Exemplary polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones, polyvinylimidazoles, and mixtures thereof. In one embodiment, the composition comprises from about 0.0001% to about 10%, about 0.01% to about 5%, or about 0.1% to about 3% dye transfer inhibiting agent by weight composition.

In some embodiments, one or more composition described herein comprises one or more silicate. Exemplary silicates include, but are not limited to, sodium silicates, e.g., sodium disilicate, sodium metasilicate, and crystalline phyllosilicates. In some embodiments, silicates are present at a level of from about 1% to about 20% or about 5% to about 15% by weight of the composition.

In some still additional embodiments, one or more composition described herein comprises one or more dispersant. Exemplary water-soluble organic materials include, but are not limited to, e.g., homo- or co-polymeric acids or their salts, in which the polycarboxylic acid comprises at least two carboxyl radicals separated from each other by not more than two carbon atoms.

In some further embodiments, one or more composition described herein comprises one or more enzyme stabilizer. In some embodiments, the enzyme stabilizer is water-soluble sources of calcium and/or magnesium ions. In some embodiments, the enzyme stabilizers include oligosaccharides, polysaccharides, and inorganic divalent metal salts, including alkaline earth metals, such as calcium salts. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), tin (II), cobalt (II), copper (II), nickel (II), and oxovanadium (IV)). Chlorides and sulfates also find use in some embodiments. Exemplary oligosaccharides and polysaccharides (e.g., dextrins) are described, for example, in WO 07/145964. In some embodiments, reversible protease inhibitors also find use, such as boron-containing compounds (e.g., borate, 4-formyl phenyl boronic acid, and phenyl-boronic acid derivatives (such as for example, those described in WO96/41859)) and/or a peptide aldehyde, such as, for example, is further described in WO2009/118375 and WO2013004636.

Peptide aldehydes may be used as protease stabilizers in detergent formulations as previously described (WO199813458, WO2011036153, US20140228274). Examples of peptide aldehyde stabilizers are peptide aldehydes, ketones, or halomethyl ketones and might be 'N-capped' with for instance a ureido, a carbamate, or a urea moiety, or 'doubly N-capped' with for instance a carbonyl, a ureido, an oxiamide, a thioureido, a dithiooxamide, or a thiooxamide moiety (EP2358857B1). The molar ratio of these inhibitors to the protease may be 0.1:1 to 100:1, e.g. 0.5:1-50:1, 1:1-25:1 or 2:1-10:1. Other examples of protease stabilizers are benzophenone or benzoic acid anilide derivatives, which might contain carboxyl groups (U.S. Pat. No. 7,968,508 B2). The molar ratio of these stabilizers to protease is preferably in the range of 1:1 to 1000:1 in particular 1:1 to 500:1 especially preferably from 1:1 to 100:1, most especially preferably from 1:1 to 20:1.

In some embodiments, one or more composition described herein comprises one or more bleach, bleach activator, and/or bleach catalyst. In some embodiments, one or more composition described herein comprises one or more inorganic and/or organic bleaching compound. Exemplary inorganic bleaches include, but are not limited to perhydrate salts, e.g., perborate, percarbonate, perphosphate, persulfate, and persilicate salts. In some embodiments, inorganic perhydrate salts are alkali metal salts. In some embodiments, inorganic perhydrate salts are included as the crystalline solid, without additional protection, although in some other embodiments, the salt is coated. Bleach activators are typically organic peracid precursors that enhance the bleaching action in the course of cleaning at temperatures of 60° C. and below. Exemplary bleach activators include compounds which, under perhydrolysis conditions, give aliphatic peroxycarboxylic acids having from about 1 to about 10 carbon atoms or about 2 to about 4 carbon atoms, and/or optionally substituted perbenzoic acid. Exemplary bleach activators are described, for example, in EP 2100949. Exemplary bleach catalysts include, but are not limited to, manganese triazacyclononane and related complexes, as well as cobalt, copper, manganese, and iron complexes. Additional exemplary bleach catalysts are described, for example, in U.S. Pat. Nos. 4,246,612; 5,227,084; 4,810,410; WO 99/06521; and EP 2100949.

In some embodiments, one or more composition described herein comprises one or more catalytic metal complexes. In some embodiments, a metal-containing bleach catalyst finds use. In some embodiments, the metal bleach catalyst comprises a catalyst system comprising a transition metal cation of defined bleach catalytic activity (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof (see, e.g., U.S. Pat. No. 4,430,243). In some embodiments, one or more composition described herein is catalyzed by means of a manganese compound. Such compounds and levels of use are described, for example, in U.S. Pat. No. 5,576,282. In additional embodiments, cobalt bleach catalysts find use and are included in one or more composition described herein. Various cobalt bleach catalysts are described, for example, in USPNs 5,597,936 and 5,595,967.

In some additional embodiments, one or more composition described herein includes a transition metal complex of a macropolycyclic rigid ligand (MRL). As a practical matter, and not by way of limitation, in some embodiments, the compositions and cleaning processes described herein are adjusted to provide on the order of at least one part per hundred million, from about 0.005 ppm to about 25 ppm, about 0.05 ppm to about 10 ppm, or about 0.1 ppm to about 5 ppm of active MRL in the wash liquor. Exemplary MRLs include, but are not limited to special ultra-rigid ligands that are cross-bridged, such as, e.g., 5,12-diethyl-1,5,8,12-tetraazabicyclo (6.6.2) hexadecane. Exemplary metal MRLs are described, for example, in WO 2000/32601 and U.S. Pat. No. 6,225,464.

In another embodiment, one or more composition described herein comprises one or more metal care agent. In some embodiments, the composition comprises from about 0.1% to about 5% metal care agent by weight composition. Exemplary metal care agents include, for example, aluminum, stainless steel, and non-ferrous metals (e.g., silver and copper). Additional exemplary metal care agents are described, for example, in EP 2100949, WO 94/26860, and WO 94/26859. In some compositions, the metal care agent is a zinc salt.

In some embodiments, the cleaning composition is a heavy duty liquid (HDL) composition comprising one or more subtilisin variant described herein. The HDL liquid laundry detergent can comprise a detersive surfactant (10-40%) comprising anionic detersive surfactant selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof; and optionally non-ionic surfactant selected from a group of linear or branched or random chain, substituted or unsubstituted alkyl alkoxylated alcohol, for example, a $C_8$-$C_{18}$alkyl ethoxylated alcohol and/or $C_6$-$C_{12}$alkyl phenol alkoxylates, optionally wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from alkyl pyridinium compounds, alkyl quaternary ammonium compounds, alkyl quaternary phosphonium compounds, alkyl ternary sulphonium compounds, and/or mixtures thereof); zwitterionic and/or amphoteric detersive surfactants (selected from alkanolamine sulpho-betaines); ampholytic surfactants; semi-polar non-ionic surfactants; and mixtures thereof.

In another embodiment, the cleaning composition is a liquid or gel detergent, which is not unit dosed, that may be aqueous, typically containing at least 20% and up to 95% water by weight, such as up to about 70% water by weight, up to about 65% water by weight, up to about 55% water by weight, up to about 45% water by weight, or up to about 35% water by weight. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous, The composition can comprise optionally, a surfactancy boosting polymer consisting of amphiphilic alkoxylated grease cleaning polymers selected from a group of alkoxylated polymers having branched hydrophilic and hydrophobic properties, such as alkoxylated polyalkylenimines in the range of 0.05 wt %-10 wt % and/or random graft polymers typically comprising a hydrophilic backbone comprising monomers selected from the group consisting of: unsaturated $C_1$-$C_6$ carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$ alkyl group, polypropylene, polybutylene, vinyl ester of a saturated $C_2$-$C_6$ mono-carboxylic acid, $C_1$-$C_6$ alkyl ester of acrylic or methacrylic acid, and mixtures thereof.

The composition can comprise additional polymers such as soil release polymers including, for example, anionically end-capped polyesters, for example SRP1; polymers comprising at least one monomer unit selected from saccharide, dicarboxylic acid, polyol and combinations thereof, in random or block configuration; ethylene terephthalate-based polymers and co-polymers thereof in random or block configuration, for example, Repel-o-tex SF, SF-2 and SRP6, Texcare SRA100, SRA300, SRN100, SRN170, SRN240, SRN300 and SRN325, Marloquest SL; anti-redeposition polymers (0.1 wt % to 10 wt %, including, for example, carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof; vinylpyrrolidone homopolymer; and/or polyethylene glycol with a molecular weight in the range of from 500 to 100,000 Da); cellulosic polymer (including, for example, alkyl cellulose; alkyl alkoxyalkyl cellulose; carboxyalkyl cellulose; alkyl carboxyalkyl cellulose, examples of which include carboxymethyl cellulose, methyl cellulose, methyl hydroxyethyl cellulose, methyl carboxymethyl cellulose; and mixtures thereof); and polymeric carboxylate (such as, for example, maleate/acrylate random copolymer or polyacrylate homopolymer).

The composition can further comprise saturated or unsaturated fatty acid, preferably saturated or unsaturated C12-Czafatty acid (0-10 wt %); deposition aids (including, for example, polysaccharides, cellulosic polymers, polydiallyl dimethyl ammonium halides (DADMAC), and co-polymers of DADMAC with vinyl pyrrolidone, acrylamides, imidazoles, imidazolinium halides, and mixtures thereof, in random or block configuration; cationic guar gum; cationic cellulose such as cationic hydroxyethyl cellulose; cationic starch; cationic polyacylamides; and mixtures thereof.

The composition can further comprise dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof, chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethyletbylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

The composition can further comprise silicone or fatty-acid based suds suppressors; an enzyme stabilizer; hueing dyes, calcium and magnesium cations, visual signaling ingredients, anti-foam (0.001 to about 4.0 wt %), and/or structurant/thickener (0.01-5 wt %) selected from the group consisting of diglycerides, triglycerides, ethylene glycol distearate, microcrystalline cellulose, cellulose based materials, microfiber cellulose, biopolymers, xanthan gum, gellan gum, and mixtures thereof.

In some embodiments, the cleaning composition is a heavy-duty powder (HDD) composition comprising one or more subtilisin variant described herein. The HDD powder laundry detergent can comprise a detersive surfactant including anionic detersive surfactants (selected from linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (selected from linear or branched or random chain, substituted or unsubstituted $C_8$-$C_{18}$ alkyl ethoxylates, and/or $C_6$-$C_{12}$ alkyl phenol alkoxylates), cationic detersive surfactants (selected from alkyl pyridinium compounds, alkyl quaternary ammonium compounds, alkyl quaternary phosphonium compounds, alkyl ternary sulphonium compounds, and mixtures thereof); zwitterionic and/or amphoteric detersive surfactants (selected from alkanolamine sulpho-betaines); ampholytic surfactants; semi-polar non-ionic surfactants and mixtures thereof; builders (phosphate free builders, e,g., zeolite builders examples of which include zeolite A, zeolite X, zeolite P and zeolite MAP in the range of 0 to less than 10 wt %); phosphate builders, e.g., sodium tri-polyphosphate in the range of 0 to less than 10 wt %; citric acid, citrate salts and nitrilotriacetic acid or salt thereof in the range of less than 15 wt %; silicate salt (sodium or potassium silicate or sodium meta-silicate in the range of 0 to less than 10 wt % or layered silicate (SKS-6)); carbonate salt (sodium carbonate and/or sodium bicarbonate in the range of 0 to less than 10 wt %); and bleaching agents (photobleaches, e.g., sulfonated zinc phthalocyanines, sulfonated aluminum phthalocyanines, xanthenes dyes, and mixtures thereof); hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, and nonanoyloxybenzene sulfonate-NOBS, nitrile quats, and mixtures thereof); hydrogen peroxide; sources of hydrogen peroxide (inorganic perhydrate salts, e.g., mono or tetra hydrate sodium salt of perborate, percarbonate, persulfate, perphosphate, or persilicate); preformed hydrophilic and/or hydrophobic peracids (selected from percarboxylic acids and salts, percarbonic acids and salts, perimidic acids and salts, peroxymonosulfuric acids and salts, and mixtures thereof); and/or bleach catalyst (e.g., imine bleach boosters, such as iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof), metal-containing bleach catalyst (e.g., copper, iron, titanium, ruthenium, tungsten, molybdenum, or manganese cations along with an auxiliary metal cations such as zine or aluminum and a sequestrate such as ethylenediaminetetraacetic acid, ethylenediaminetetra (methylenephosphonic acid) and water-soluble salts thereof).

The composition can further comprise additional detergent ingredients including perfume microcapsules, starch encapsulated perfume accord, an enzyme stabilizer, hueing agents, additional polymers including fabric integrity and cationic polymers, dye lock ingredients, fabric-softening agents, brighteners (for example C.I. Fluorescent brighteners), flocculating agents, chelating agents, alkoxylated polyamines, fabric deposition aids, and/or cyclodextrin.

In some embodiments, the cleaning composition is an ADW detergent composition comprising one or more subtilisin variant described herein. The ADW detergent composition can comprise two or more non-ionic surfactants selected from ethoxylated non-ionic surfactants, alcohol alkoxylated surfactants, epoxy-capped poly (oxyalkylated) alcohols, and amine oxide surfactants present in amounts from 0-10% by wt; builders in the range of 5-60% by wt. comprising either phosphate (mono-phosphates, di-phosphates, tri-polyphosphates or oligomeric-poylphosphates), sodium tripolyphosphate-STPP or phosphate-free builders (amino acid based compounds, e.g., MGDA (methyl-glycine-diacetic acid) and salts and derivatives thereof, GLDA (glutamic-N,N-diacetic acid) and salts and derivatives thereof, IDS (iminodisuccinic acid) and salts and derivatives thereof, carboxy methyl inulin and salts and derivatives thereof and mixtures thereof, nitrilotriacetic acid (NTA), diethylene triamine penta acetic acid (DTPA), and B-alaninediacetic acid (B-ADA) and their salts), homopolymers and copolymers of poly-carboxylic acids and their partially or completely neutralized salts, monomeric polycarboxylic acids and hydroxycarboxylic acids and their salts in the range of 0.5-50% by wt; sulfonated/carboxylated polymers (provide dimensional stability to the product) in the range of about 0.1 to about 50% by wt; drying aids in the range of about 0.1 to about 10% by wt (selected from polyesters, especially anionic polyesters optionally together with further monomers with 3-6 functionalities which are conducive to polycondensation, specifically acid, alcohol or ester functionalities, polycarbonate-, polyurethane- and/or polyurea-polyorganosiloxane compounds or precursor compounds thereof of the reactive cyclic carbonate and urea type); silicates in the range from about 1 to about 20% by wt (sodium or potassium silicates, e.g., sodium disilicate, sodium meta-silicate and crystalline phyllosilicates); bleach-inorganic (e.g., perhydrate salts such as perborate, percarbonate, perphosphate, persulfate and persilicate salts) and organic (e.g., organic peroxyacids including diacyl and tetraacylperoxides, especially diperoxy dodecanedioic acid, diperoxytetradecanedioic acid, and diperoxyhexadecanedioic acid); bleach activator-organic peracid precursors in the range from about 0.1 to about 10% by wt; bleach catalysts (selected from manganese triazacyclononane and related complexes, Co, Cu, Mn and Fe bispyridylamine and related complexes, and pentamine acetate cobalt (III) and related complexes); metal care agents in the range from about 0.1-5% by wt (selected from benzatriazoles, metal salts and complexes, and silicates); enzymes in the range from about 0.01-5.0 mg of active enzyme per gram of ADW detergent composition (acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, nucleases, oxidases, oxidoreductases, pectate lyases, pectin acetyl esterases, pectinases, pentosanases, peroxidases, phenoloxidases, phosphatases, phospholipases, phytases, polyesterases, polygalacturonases, proteases, pullulanases, reductases, rhamnogalacturonases, beta-glucanases, tannases, transglutaminases, xylan acetyl-esterases, xylanases, xyloglucanases, xylosidases, and mixtures thereof); and enzyme stabilizer components (selected from oligosaccharides, polysaccharides and inorganic divalent metal salts).

More embodiments are directed to compositions and methods of treating fabrics (e.g., to desize a textile) using one or more subtilisin variant described herein. Fabric-treating methods are well known in the art (see, e.g., U.S. Pat. No. 6,077,316). For example, the feel and appearance of a fabric can be improved by a method comprising contacting the fabric with a variant described herein in a solution. The fabric can be treated with the solution under pressure.

One or more subtilisin variant described herein can be applied during or after weaving a textile, during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. One or more subtilisin variant described herein can be applied during or after weaving to remove the sizing starch or starch derivatives. After weaving, the variant can be used to remove the size coating before further processing the fabric to ensure a homogeneous and wash-proof result. One or more subtilisin variant described herein can be used alone or with other desizing chemical reagents and/or desizing enzymes to desize fabrics, including cotton-containing fabrics, as detergent additives, e.g., in aqueous compositions. An amylase also can be used in combination with the subtilisin variant in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of proteolytic enzymes to provide softness to the fabric and make the cotton more accessible to the subsequent enzymatic finishing steps. One or more subtilisin variant described herein can be used in methods of finishing denim garments (e.g., a "bio-stoning process"), enzymatic desizing and providing softness to fabrics, and/or finishing process.

The following examples are provided to demonstrate and illustrate certain preferred embodiments and aspects of the present disclosure and should not be construed as limiting.

EXAMPLE 1

Assays
HPLC Assay for Protein Determination

The concentration of the sample proteases in culture supernatant was determined by UHPLC using a Zorbax 300 SB-C3 column and linear gradient of 0.1% Trifluoroacetic acid (Buffer A) and 0.07% Trifluoroacetic acid in Acetonitrile (Buffer B) and detection at 220 nm. Culture supernatants were diluted in 10 mM NaCl, 0.1 mM CaCl, 0.005%

Tween-80 for loading onto column. The protein concentration of the samples was calculated using a standard curve of the purified parent enzyme Bgi02446-S039E.

Cleaning Performance in Detergent

Egg Yolk Stain

The automatic dishwashing (ADW) cleaning performance of the subtilisin Bgi02446-S039E variants described herein was tested relative to parent using egg yolk (PAS-38, Center for Testmaterials BV, Vlaardingen, Netherlands) microswatches and the GSM-B detergent (see Table 1), pH 10.5 and in microtiter plates (MTPs). Pre-punched PAS-38 (to fit on MTP) rinsed and unrinsed swatches were used in this assay. Rinsed swatches were prepared by adding 180 uL 10 mM CAPS buffer pH 11 to MTPs containing the PAS-38 microswatches and shaking for 30 min at 60° C. and 1100 rpm. After incubation, the buffer was removed, the swatches rinsed with deionized water to remove any residual buffer, and the MTPs air dried prior to use in the assay. All microswatch plates were filled prior to enzyme addition with 3 g/l GSM-B detergent adjusted to 374 ppm water hardness. After incubating the PAS-38 swatches with detergent and enzymes for 30 min at 40° C., absorbance was read at 405 nm with a SpectraMax plate reader. Absorbance results were obtained by subtracting the value for a blank control (no enzyme) from each sample value (hereinafter "blank subtracted absorbance"). For each condition and subtilisin variant, a performance index (PI) was calculated by dividing the blank subtracted absorbance by that of the parent protease Bgi02446-S039E at the same concentration. The value for the parent protease was determined from a standard curve of the parent protease which was included in the test and which was fitted to a Langmuir fit or Hill Sigmoidal fit, as appropriate.

BMI Stain

The heavy duty liquid laundry (HDL) and heavy duty powder laundry (HDD) detergent cleaning performance of the subtilisin Bgi02446-S039E variants described herein relative to parent was tested using BMI microswatches (blood/milk/ink on cotton) (EMPA-116, Center for Testmaterials BV, Vlaardingen, Netherlands). Pre-punched BMI (to fit on MTP) were used. The MTP plates were filled prior to enzyme addition with 2.7 g/l Persil Non-Bio (Unilever) HDL detergent adjusted to 250 ppm water hardness, or 6.5 g/l ECE-2 HDD adjusted to 250 ppm water hardness. Persil Non-Bio, which was purchased for use in this test in the United Kingdom in 2014, does not contain boron or enzymes. ECE-2 detergent from wfk Testgewebe is more fully described in Table 3 set forth hereinbelow. After incubating the EMPA-116 swatches with detergent and enzymes for 15 min at 25° C., absorbance was read at 600 nm with a SpectraMax plate reader. Absorbance results were obtained by subtracting the value for a blank control (no enzyme) from each sample value (hereinafter "blank subtracted absorbance"). For each condition and subtilisin variant, a performance index (PI) was calculated by dividing the blank subtracted absorbance by that of the parent protease Bgi02446-S039E at the same concentration. The value for the parent protease was determined from a standard curve of the parent protease which was included in the test and which was fitted to a Langmuir fit or Hill Sigmoidal fit, as appropriate.

Crème Brûlée Stain

Crème Brûlée stain: The cleaning performance of $B.$ $gibsonii$ subtilisin variants on crème brûlée stain was tested by using custom ordered melamine dishwasher monitors (tiles) prepared by CFT in Vlaardingen, the Netherlands as set forth herein, and labeled DM10c. The DM10c tiles used in this study are prepared using 2.7 g of the same material used to prepare the commercially available DM10 monitors (crème brûlée Debic.com product) but baked at 140° C. for 2 hours, instead of 150° C. The melamine tiles were used as a lid and tightly pressed onto a microtiter plate (MTP). 3 g/L of GSMB or MGDA detergent (Tables 1 and 2, respectively) adjusted to 374 ppm water hardness and each enzyme sample were added to the MTP prior to attaching the melamine tile lid to the MTP. The volume capacity of the MTP, and therefore the volume of solution added thereto, may vary, wherein a minimal volume of solution should be added to the MTP that enables contact between solution and stain surface under the incubation conditions. In this example, a volume of 300 pL of detergent containing enzyme was added to each well of an aluminum 96-well MTP. The MTPs were incubated in an Infors thermal shaker for 45 min at 40° C. at 250 rpm. After incubation, the tiles were removed from the MTP and air-dried.

Stain removal was quantified by photographing the plates and measuring the RGB values from each stain area using custom software. Percent Soil removal (% SRI) values of the washed tiles were calculated by using the RGB values in the following formula:

$$\% \text{ SRI} = (\Delta E/\Delta E \text{ initial}) * 100$$

$$\text{Where } \Delta B = SQR\ ((R_{after} - R_{before})^2 + (G_{after} - G_{before})^2 + (B_{after} - B_{before})^2)$$

$$\text{Where } \Delta E_{initial} = SQR((R_{white} - R_{before})^2 + (G_{white} - G_{before})^2 + (B_{white} - B_{before})^2)$$

Cleaning performance was obtained by subtracting the value of a blank control (no enzyme) from each sample value (hereinafter "blank subtracted cleaning"). For each condition and subtilisin variant, a performance index (PI) was calculated by dividing the blank subtracted cleaning by that of the parent protease at the same concentration. The value for the parent protease PI was determined from a standard curve of the parent protease Bgi02446-S039E which was included in the test and which was fitted to a Langmuir fit or Hill Sigmoidal fit, as appropriate.

TABLE 1

GSM-B pH 10.5 Phosphate-Free ADW Detergent Ingredients

| Component | Weight % |
|---|---|
| Sodium citrate dehydrate | 30.0 |
| Maleic acid/acrylic acid copolymer sodium salt (SOKALAN ® CP5; BASF) | 12.0 |
| Sodium perborate monohydrate | 5.0 |
| TAED | 2.0 |
| Sodium disilicate: Protil A (Cognis) | 25.0 |
| Linear fatty alcohol ethoxylate | 2.0 |
| Sodium carbonate anhydrous | add to 100 |

TABLE 2

MGDA pH 10.5 ADW Detergent Ingredients

| Component | Weight % |
|---|---|
| MGDA | 64.6 |
| Plurafac SLF 18-45D | 4.4 |
| Bismuthcitrate | 0.4 |
| Phosphonates (Bayhibit S) | 0.4 |
| Acusol 420/Acosul 587 | 1.6 |
| PEG6000 | 2.4 |
| PEG1500 | 5.9 |

TABLE 2-continued

MGDA pH 10.5 ADW Detergent Ingredients

| Component | Weight % |
| --- | --- |
| Sodium percarbonate | 16.1 |
| TAED | 4.1 |

TABLE 3

ECE-2 HDD Detergent Ingredients

| Component | Weight % |
| --- | --- |
| Linear sodium alkyl benzene sulfonate | 9.7 |
| Ethoxylated fatty alcohol C12-18 (7 EO) | 5.2 |
| Sodium soap | 3.6 |
| Antifoam DC2-4248S | 4.5 |
| Sodium aluminium silicate zeolite 4A | 32.5 |
| Sodium carbonate | 11.8 |
| Sodium salt of a copolymer from acrylic and maleic acid (Sokalan CP5) | 5.2 |
| Sodium silicate (SiO2:Na2O = 3.3:1) | 3.4 |
| Carboxymethylcellulose | 1.3 |
| Diethylene triamine penta (methylene phosphonic acid) | 0.8 |
| Sodium sulfate | 9.8 |
| Water | 12.2 |

AAPF Activity Assay

The protease activity of parent and subtilisin Bgi02446-S039E variants thereof was tested by measuring hydrolysis of N-suc-AAPF-pNA. The reagent solutions used for the AAPF hydrolysis assay were: 100 mM Tris/HCl pH 8.6, containing 0.005% TWEEN®-80 (Tris dilution buffer); 100 mM Tris buffer pH 8.6, containing 10 mM $CaCl_2$) and 0.005% TWEEN®-80 (Tris/Ca buffer); and 160 mM suc-AAPF-pNA in DMSO (suc-AAPF-pNA stock solution) (Sigma: S-7388). A substrate working solution was prepared by adding 1 mL suc-AAPF-pNA stock solution to 100 mL Tris/Ca buffer and mixed well. An enzyme sample was added to a MTP (Greiner 781101) containing 1 mg/suc-AAPF-pNA working solution and assayed for activity at 405 nm over 3 min with a SpectraMax plate reader in kinetic mode at room temperature (RT). The absorbance of a blank containing no protease was subtracted from each sample reading. The protease activity was expressed as mOD min-1.

Stability Assay

The stability of the subtilisin Bgi02446-S039E variants described herein was measured by diluting the variants in stress buffer and measuring the proteolytic activity of the variants before and after a heat incubation step using the AAPF assay described above. The temperature and duration of the heat incubation step were chosen such that the reference protease showed approximately 30-45% residual activity. Samples were incubated at 56° C. for 5 min in a 384-well thermocycler. Stability was measured in Tris-EDTA (50 mM Tris pH 9; 5 mM EDTA; 0.005% Tween 80) buffered condition. Stability PIs were obtained by dividing the residual activity of subtilisin variant by that of the Bgi02446-S039E parent protease.

EXAMPLE 2

Expression of Bgi02446-S039E Parent Subtilisin and Variants Thereof

DNA manipulations to Bgi02446-S039E parent subtilisin and variants thereof were carried out using conventional molecular biology techniques (see, e.g., Sambrook et al, Molecular Cloning: Cold Spring Harbor Laboratory Press). Artificial DNA sequences were generated that code for mature Bgi02446-S039E subtilisin parent and variant sequences with amino acid modifications introduced into the sequence of the parent subtilisin at the positions described below. All subtilisins were expressed and recovered as described hereinbelow. Protease samples for the studies described herein were generated by culturing cells in selective growth medium in a 96-well MTP at 31° C. for 68 hours. Clarified culture supernatants were prepared by centrifugation and filtration.

B. gibsonii-Bgi02446-S039E parent subtilisin (mature protein, SEQ ID NO: 1) and variants thereof were expressed by using a DNA fragment comprising: a 5'AprE flanking region that contains the B. subtilis P1 rml promoter sequence (SEQ ID NO: 2) (the B. subtilis P1 rml promoter is more fully described in US-2014-0329309), the aprE signal peptide sequence (SEQ ID NO: 3), the pro sequence from B. lentus (SEQ ID NO: 4), the sequence corresponding to the gene for the Bgi02446-S039E parent subtilisin (SEQ ID NO: 5), the BPN' terminator (SEQ ID NO: 6), the chloramphenicol acetyl transferase (CAT) gene expression cassette from S. aureus (SEQ ID NO: 7), and the 3'AprE flanking sequence (SEQ ID NO: 8), in consecutive order was assembled using standard molecular techniques. The amino acid sequence of the B. subtilis aprE signal peptide encoded by SEQ ID NO: 3 is set forth as SEQ ID NO: 9. The amino acid sequence of the pro sequence encoded by SEQ ID NO: 4 is set forth as SEQ ID NO: 10. This linear B. gibsonii Bgi02446-S039E expression cassette was used to transform 200 μL of competent B. subtilis cells of a suitable strain. The transformed cells were incubated at 37° C. for 1 hour while shaking at 250 rpm. The transformation mixture was plated onto LA plates containing 1.6% skim milk and 5 ppm chloramphenicol (CMP) and incubated overnight at 37° C. Single colonies were picked and grown in Luria broth+5 ppm CMP at 37° C. Strain samples were frozen at −80° C. with 20% glycerol for storage.

Genomic DNA of the B. subtilis strain expressing the B. gibsonii Bgi02446-S039E subtilisin was isolated and used as a template to generate variants of the B. gibsonii Bgi02446 mature protease region. Variants containing single site amino acid substitutions were created using a polymerase chain reaction with appropriate primer pairs, DNA template, and Q5 polymerase (New England Biolabs). These assembled fragments were used to transform competent B. subtilis cells and the transformants were handled as described above.

The B. gibsonii Bgi02446-S039E subtilisin variants that were generated are listed below in Table 4, with the positions of the amino acid substitutions described relative to-the B. gibsonii Bgi02446 subtilisin parent.

EXAMPLE 3

Performance of Bgi02446-S039E Variants in Laundry and Dish Applications

The cleaning performance of the Bgi02446-S039E subtilisin and variants thereof made in accordance with Example 2 were evaluated in the following cleaning assays: the PAS-38 technical stain using the GSM-B detergent, the BMI stain using either Persil non-Bio HDL or ECE-2 HDD detergents, and the Crème Brûlée stain using either GSM-B or MGDA detergents, and in the stability assay described in Example 1. The results for these evaluations of Bgi02446-S039E subtilisin and variants thereof are reported as Performance Index (PI) values calculated versus the parent subtilisin Bgi02446-S039E as described in Example 1 and are shown on Table 4.

TABLE 4

Stability, and Cleaning Performance in Laundry HDL and HDD BMI, ADW EGG and Crème Brûlée of Bgi02446-S039E Variants.

| Amino acid substitutions relative to Bgi02446-S039E | Stability in EDTA with respect to Bgi02446-S039E | Laundry BMI Performance with respect to Bgi02446-S039E | | ADW EGG performance with respect to Bgi02446-S039E | | Crème Brûlée performance with respect to Bgi02446-S039E | |
|---|---|---|---|---|---|---|---|
| | | HDL Persil Non Bio Detergent | HDD Laundry Detergent | ADW Rinsed EGG Stain | ADW Unrinsed EGG Stain | GSM-B Detergent | MGDA Detergent |
| T003V | 1.4 | 1.0 | 1.2 | 0.9 | 1.0 | 1.0 | 1.0 |
| V004T | 1.2 | 0.9 | 0.9 | 1.0 | 1.0 | 0.9 | 0.9 |
| I008V | 1.2 | 1.1 | 0.9 | 1.0 | 1.0 | 1.0 | 1.1 |
| T009A | 1.3 | 0.9 | 1.0 | 1.0 | 1.0 | 1.2 | 1.1 |
| T009C | 1.0 | 1.1 | <0.9 | 1.0 | 0.9 | 1.5 | 1.7 |
| T009E | 1.2 | 1.0 | <0.9 | <0.9 | 0.9 | 1.3 | 1.5 |
| T009G | 1.1 | 1.0 | 1.0 | <0.9 | 0.9 | 0.9 | 1.0 |
| T009H | 1.2 | 1.0 | 1.1 | 1.1 | 1.1 | 1.0 | 1.1 |
| T009K | 1.1 | <0.9 | <0.9 | 1.1 | 1.2 | <0.9 | <0.9 |
| T009M | 1.0 | 1.0 | 1.0 | 1.0 | 1.0 | 1.3 | 1.2 |
| T009N | 1.1 | 1.0 | 0.9 | 0.9 | 1.1 | 1.2 | 1.3 |
| T009Q | 1.2 | 1.0 | 1.3 | 0.9 | 1.0 | 1.1 | 1.1 |
| T009S | 1.2 | 1.1 | 1.0 | 1.0 | 1.0 | 1.0 | 1.1 |
| T009W | 1.2 | 1.0 | 1.3 | 1.1 | 1.1 | 1.0 | 1.1 |
| T009Y | 1.2 | 0.9 | <0.9 | 1.0 | 1.0 | 1.2 | 1.1 |
| R010A | 1.0 | 1.0 | <0.9 | 1.0 | 0.9 | 1.8 | 1.7 |
| R010K | 0.9 | 0.9 | <0.9 | 0.9 | 1.0 | 1.2 | 1.0 |
| R010M | 1.0 | 1.0 | <0.9 | 0.9 | 1.0 | 2.1 | 1.8 |
| R010N | 1.0 | 1.1 | <0.9 | 0.9 | <0.9 | 1.7 | 1.8 |
| R010Q | 1.1 | 1.1 | <0.9 | <0.9 | <0.9 | 1.5 | 1.6 |
| R010W | 1.0 | 1.1 | <0.9 | <0.9 | <0.9 | 1.1 | 1.2 |
| V011A | 1.1 | 1.0 | 0.9 | 1.0 | 1.1 | 1.3 | 1.4 |
| V011I | 1.0 | 1.0 | 0.9 | 1.0 | 1.2 | 1.1 | 1.1 |
| V011S | 1.0 | 1.1 | 0.9 | 1.0 | 1.0 | 1.0 | 1.0 |
| V011T | 1.0 | 1.1 | 0.9 | 1.0 | 1.0 | 1.1 | 1.0 |
| Q012A | 1.1 | 1.2 | 0.9 | 1.0 | 1.1 | 1.1 | 1.2 |
| Q012C | 1.1 | 1.3 | <0.9 | 0.9 | 0.9 | 1.4 | 1.6 |
| Q012D | 1.0 | 1.2 | <0.9 | 0.9 | 0.9 | 1.5 | 1.6 |
| Q012B | 1.0 | 1.3 | <0.9 | 0.9 | 0.9 | 1.3 | 1.4 |
| Q012G | 1.1 | 1.1 | 0.9 | 1.0 | 1.1 | 0.9 | 1.0 |
| Q012M | 1.1 | 1.2 | 1.1 | 0.9 | 1.1 | 1.1 | 1.1 |
| Q012N | 1.2 | 1.3 | 1.0 | 0.9 | 1.1 | 1.1 | 1.1 |
| Q012R | 1.0 | 1.1 | 1.2 | 0.9 | 1.1 | <0.9 | <0.9 |
| Q012S | 1.0 | 1.1 | 1.0 | 0.9 | 1.1 | 0.9 | <0.9 |
| Q012T | 1.1 | 1.2 | 1.0 | 1.0 | 0.9 | <0.9 | 0.9 |
| Q012V | 1.0 | 1.1 | 0.9 | 0.9 | 1.1 | <0.9 | <0.9 |
| Q012W | 0.9 | 1.1 | 1.1 | 1.0 | 1.1 | <0.9 | <0.9 |
| P014D | 1.0 | 1.1 | <0.9 | 1.0 | 0.9 | 1.2 | 1.4 |
| A015D | 1.0 | 1.1 | 0.9 | 1.0 | 1.0 | 1.2 | 1.4 |
| A015E | 1.0 | 1.0 | <0.9 | 1.0 | 0.9 | 0.9 | 1.4 |
| A015F | 1.1 | 0.9 | <0.9 | 1.1 | 1.1 | <0.9 | 1.0 |
| A015H | 1.1 | 1.1 | <0.9 | 1.0 | 1.0 | 1.4 | 1.0 |
| A015I | 1.0 | 1.0 | 0.9 | 1.1 | 1.1 | 1.4 | 1.0 |
| A015K | 1.0 | ND | 1.1 | 1.0 | 1.1 | 1.0 | <0.9 |
| A015M | 1.1 | 1.0 | 1.2 | 0.9 | 1.1 | 1.8 | 1.2 |
| A015P | 1.1 | 1.0 | 1.0 | 1.0 | 1.0 | <0.9 | 1.0 |
| A015Q | 1.1 | 1.0 | 1.2 | 1.0 | 1.0 | 0.9 | 1.0 |
| A015V | 1.0 | 1.1 | 0.9 | 1.1 | 1.0 | 1.6 | 1.1 |
| A015W | 1.1 | 0.9 | 0.9 | 1.0 | 0.9 | 1.3 | 1.0 |
| A015Y | 1.0 | 1.0 | <0.9 | 1.0 | 0.9 | 1.7 | 1.1 |
| V016L | 1.0 | 1.0 | 1.0 | 1.0 | 1.1 | 1.1 | 0.9 |
| V016M | 1.0 | 1.2 | 1.2 | 1.0 | 1.1 | 1.6 | 1.0 |
| V016S | 1.1 | 1.1 | 0.9 | 0.9 | 0.9 | 0.9 | 0.9 |
| H017C | 1.3 | 1.1 | <0.9 | 1.0 | 0.9 | 1.2 | 1.3 |
| H017E | 1.2 | 1.0 | 1.0 | <0.9 | 0.9 | 1.2 | 1.0 |
| H017F | 1.3 | 1.1 | 1.1 | 1.1 | 1.1 | 0.9 | <0.9 |
| H017G | 1.0 | 1.0 | 1.0 | 1.1 | 1.0 | <0.9 | 0.9 |
| H017I | 1.4 | 1.2 | 1.0 | 1.1 | 1.1 | <0.9 | <0.9 |
| H017L | 1.4 | 0.9 | 1.1 | 1.1 | 1.1 | <0.9 | <0.9 |
| H017N | 1.1 | 1.1 | ND | 0.9 | 1.1 | 1.0 | 0.9 |
| H017V | 1.2 | 1.0 | 1.0 | 1.1 | 1.0 | <0.9 | <0.9 |
| H017W | 1.3 | 1.3 | 1.0 | 1.1 | 1.0 | <0.9 | <0.9 |
| H017Y | 1.1 | 1.1 | 0.9 | 0.9 | 1.1 | <0.9 | <0.9 |
| N018A | 1.1 | 1.0 | ND | 1.0 | 1.0 | 1.0 | 1.2 |
| N018C | 1.0 | 0.9 | <0.9 | 0.9 | 0.9 | 1.3 | 1.2 |
| N018D | 1.1 | 1.1 | <0.9 | 1.0 | 0.9 | 1.3 | 1.5 |

TABLE 4-continued

Stability, and Cleaning Performance in Laundry HDL and HDD BMI, ADW EGG and Crème Brûlée of Bgi02446-S039E Variants.

| Amino acid substitutions relative to Bgi02446-S039E | Stability in EDTA with respect to Bgi02446-S039E | Laundry BMI Performance with respect to Bgi02446-S039E | | ADW EGG performance with respect to Bgi02446-S039E | | Crème Brûlée performance with respect to Bgi02446-S039E | |
|---|---|---|---|---|---|---|---|
| | | HDL Persil Non Bio Detergent | HDD Laundry Detergent | ADW Rinsed EGG Stain | ADW Unrinsed EGG Stain | GSM-B Detergent | MGDA Detergent |
| N018E | 1.1 | 1.1 | <0.9 | ND | <0.9 | 1.2 | 1.4 |
| N018F | 1.0 | 1.1 | 1.0 | 1.1 | 1.0 | 1.0 | 1.1 |
| N018G | 1.0 | 1.1 | 0.9 | 1.0 | 1.0 | 1.0 | 1.2 |
| N018L | 1.1 | 1.0 | 1.0 | 0.9 | 1.1 | 1.0 | 1.1 |
| N018M | 1.1 | 1.0 | ND | 1.0 | 1.1 | 1.0 | 1.3 |
| N018Q | 1.1 | 1.1 | 1.0 | 1.0 | 1.0 | 1.0 | 1.2 |
| N018T | 1.0 | 1.1 | 1.0 | 1.0 | 1.0 | 1.0 | 1.1 |
| R019A | 1.0 | 1.2 | 0.9 | 1.0 | 0.9 | 1.3 | 1.5 |
| R019C | 1.1 | 1.0 | <0.9 | 1.1 | <0.9 | 1.3 | 1.4 |
| R019D | 1.1 | 1.1 | <0.9 | ND | 0.9 | 1.6 | 1.7 |
| R019E | 1.0 | 1.0 | <0.9 | 0.9 | <0.9 | 1.6 | 1.7 |
| R019F | 1.0 | 1.1 | <0.9 | 0.9 | 0.9 | 1.5 | 1.6 |
| R019H | 1.0 | 1.1 | 0.9 | 0.9 | 0.9 | 1.2 | 1.4 |
| R019I | 1.0 | 1.2 | <0.9 | 1.0 | 0.9 | 1.3 | 1.3 |
| R019K | 1.0 | 1.0 | 1.0 | 1.1 | 1.0 | 1.1 | 1.0 |
| R019L | 1.0 | 1.3 | <0.9 | 1.0 | 1.1 | 1.4 | 1.3 |
| R019N | 1.0 | 1.0 | 1.0 | ND | 1.0 | 1.3 | 1.3 |
| R019Q | 1.0 | 1.1 | ND | 1.1 | 0.9 | 1.2 | 1.4 |
| R019S | 1.0 | 1.2 | <0.9 | 1.0 | 0.9 | 1.3 | 1.5 |
| R019T | 1.0 | 1.0 | <0.9 | ND | 1.0 | 1.3 | 1.4 |
| R019W | 1.0 | 1.1 | <0.9 | 1.0 | 1.0 | 1.2 | 1.4 |
| R019Y | 1.1 | 1.2 | <0.9 | 0.9 | 1.0 | 1.2 | 1.3 |
| G020A | 1.0 | 0.9 | 1.1 | 1.1 | 1.1 | 1.0 | 1.0 |
| G020C | 1.1 | 1.0 | <0.9 | 1.0 | 1.0 | 1.2 | 1.1 |
| G020D | 1.1 | 1.0 | <0.9 | 1.1 | 1.0 | 1.1 | 1.0 |
| G020M | 1.1 | 0.9 | 1.1 | 1.0 | 1.1 | 0.9 | <0.9 |
| G020N | 1.1 | 0.9 | 1.1 | 1.0 | 1.1 | 0.9 | 0.9 |
| G020T | 1.0 | 1.0 | 0.9 | 1.1 | 1.0 | <0.9 | <0.9 |
| S024A | 1.1 | 1.2 | 1.1 | 0.9 | 1.2 | 1.3 | 1.0 |
| S024E | 1.3 | 1.2 | 1.0 | 1.0 | 1.0 | 1.2 | 1.2 |
| G025A | 1.0 | 1.0 | 1.1 | 1.1 | 1.1 | 1.3 | 1.0 |
| G025C | 1.1 | 1.0 | 0.9 | 0.9 | 0.9 | 1.2 | 1.1 |
| G025D | 1.1 | 1.0 | <0.9 | 1.1 | 0.9 | 1.3 | 1.1 |
| G025E | 1.0 | 1.1 | <0.9 | 1.0 | 0.9 | 1.2 | 1.1 |
| G025M | 1.0 | 1.2 | 1.0 | 1.0 | 1.0 | 1.2 | 0.9 |
| G025N | 1.1 | 1.1 | 1.1 | 1.0 | 1.1 | 1.2 | 1.0 |
| V026A | 1.0 | 0.9 | 1.0 | 0.9 | <0.9 | 1.1 | 1.0 |
| V026I | 1.1 | <0.9 | <0.9 | 1.0 | 1.1 | 1.0 | 1.1 |
| R027K | 1.1 | 1.0 | <0.9 | 1.0 | 1.0 | 1.1 | 1.3 |
| S033T | 1.1 | 0.9 | 1.0 | 0.9 | <0.9 | <0.9 | <0.9 |
| S036A | 1.1 | 0.9 | 1.0 | 1.1 | 1.1 | 0.9 | 0.9 |
| S036C | 1.1 | 1.0 | <0.9 | 1.0 | 1.0 | 1.4 | 1.4 |
| S036E | 1.0 | 1.0 | <0.9 | 1.0 | 0.9 | 1.5 | 1.7 |
| S036I | 1.1 | 1.0 | <0.9 | 1.0 | 0.9 | <0.9 | 1.1 |
| S036L | 1.1 | 1.0 | ND | 1.1 | 0.9 | 0.9 | 1.0 |
| S036M | 1.2 | 1.0 | 1.0 | 1.0 | 0.9 | 1.0 | 1.1 |
| S036Q | 1.1 | 1.0 | 1.0 | 1.0 | 1.0 | 1.1 | 1.1 |
| S036T | 1.0 | 1.0 | 1.0 | 1.0 | 1.1 | 1.1 | 1.1 |
| S036V | 1.1 | 1.1 | <0.9 | 0.9 | <0.9 | 1.0 | 1.2 |
| N042C | 1.4 | 1.0 | <0.9 | 1.0 | 0.9 | 1.2 | 1.4 |
| N042D | 1.2 | 1.1 | 1.1 | 1.0 | 1.0 | 1.1 | 1.5 |
| N042E | 1.5 | 1.2 | <0.9 | 1.0 | 1.0 | 1.0 | 1.4 |
| N042M | 1.2 | 1.1 | 1.2 | 1.0 | 0.9 | 1.0 | 1.0 |
| N042Q | 1.1 | 1.0 | 1.1 | 1.0 | 0.9 | 0.9 | 1.1 |
| I043L | 1.0 | 0.9 | 1.0 | 1.0 | 1.0 | 1.2 | 1.3 |
| R044C | 1.3 | 1.0 | 0.9 | 1.0 | 1.1 | 1.6 | 1.7 |
| R044E | 1.3 | 1.1 | <0.9 | 1.0 | <0.9 | 1.3 | 1.5 |
| R044F | 1.2 | 1.0 | <0.9 | 0.9 | <0.9 | <0.9 | 1.0 |
| R044G | 1.1 | 1.0 | 0.9 | 1.0 | 0.9 | 1.1 | 1.3 |
| R044H | 1.2 | 1.0 | <0.9 | 1.0 | 1.1 | 1.1 | 1.3 |
| R044I | 1.2 | 1.1 | <0.9 | 0.9 | <0.9 | 0.9 | 1.2 |
| R044K | 1.1 | 1.0 | 1.0 | 1.0 | 1.1 | 1.0 | 1.1 |
| R044L | 1.2 | 1.0 | <0.9 | 0.9 | <0.9 | 1.0 | 1.2 |
| R044N | 1.2 | 1.1 | <0.9 | 1.0 | ND | 1.3 | 1.3 |
| R044Q | 1.2 | 1.0 | <0.9 | 0.9 | 1.0 | 1.2 | 1.3 |
| R044S | 1.2 | 1.1 | <0.9 | 0.9 | 0.9 | 1.0 | 1.3 |

TABLE 4-continued

Stability, and Cleaning Performance in Laundry HDL and HDD BMI,
ADW EGG and Crème Brûlée of Bgi02446-S039E Variants.

| Amino acid substitutions relative to Bgi02446-S039E | Stability in EDTA with respect to Bgi02446-S039E | Laundry BMI Performance with respect to Bgi02446-S039E | | ADW EGG performance with respect to Bgi02446-S039E | | Crème Brûlée performance with respect to Bgi02446-S039E | |
|---|---|---|---|---|---|---|---|
| | | HDL Persil Non Bio Detergent | HDD Laundry Detergent | ADW Rinsed EGG Stain | ADW Unrinsed EGG Stain | GSM-B Detergent | MGDA Detergent |
| R044T | 1.2 | 1.2 | <0.9 | 0.9 | <0.9 | 1.1 | 1.2 |
| R044V | 1.2 | 1.0 | <0.9 | 0.9 | 0.9 | 0.9 | 1.2 |
| R044W | 1.3 | 1.0 | <0.9 | 0.9 | <0.9 | 0.9 | 0.9 |
| R044Y | 1.3 | 0.9 | <0.9 | 0.9 | <0.9 | 0.9 | 0.9 |
| A047I | 1.1 | 1.0 | 0.9 | 1.0 | 1.0 | 0.9 | 1.0 |
| A047Y | 1.1 | 1.0 | <0.9 | 0.9 | 1.0 | <0.9 | 1.0 |
| V050I | 1.1 | 1.0 | 0.9 | 1.0 | 1.0 | <0.9 | 1.0 |
| G052A | 1.1 | 1.0 | <0.9 | 0.9 | 1.1 | 1.3 | 1.5 |
| G052C | 1.0 | 1.1 | <0.9 | <0.9 | <0.9 | 1.2 | 1.5 |
| G052D | 1.0 | 1.1 | <0.9 | 1.1 | 1.0 | 1.5 | 1.7 |
| G052H | 1.0 | 1.0 | 0.9 | 1.0 | 1.2 | <0.9 | 1.2 |
| G052L | 1.0 | 1.0 | <0.9 | <0.9 | <0.9 | 0.9 | 1.3 |
| G052M | 1.1 | 1.0 | <0.9 | 0.9 | 1.1 | 1.2 | 1.6 |
| G052N | 1.2 | 1.0 | 0.9 | 0.9 | 1.0 | 1.1 | 1.2 |
| G052S | 1.1 | 1.1 | <0.9 | 0.9 | 1.0 | 0.9 | 1.0 |
| G052T | 1.1 | 1.1 | <0.9 | 0.9 | 1.0 | <0.9 | 1.1 |
| G052Y | 1.1 | 0.9 | <0.9 | <0.9 | 0.9 | <0.9 | 1.0 |
| P054A | 1.0 | 1.0 | <0.9 | 1.0 | 1.1 | 1.5 | 1.4 |
| P054C | 1.0 | 1.0 | <0.9 | 1.0 | 0.9 | 1.3 | 1.4 |
| P054G | 1.0 | 1.0 | 0.9 | 1.1 | <0.9 | 0.9 | <0.9 |
| P054L | 1.0 | 1.0 | <0.9 | 1.0 | 1.2 | 0.9 | 1.5 |
| P054M | 1.0 | 1.1 | 0.9 | 0.9 | 1.3 | 1.8 | 2.1 |
| P054N | 1.1 | 1.0 | 1.1 | 0.9 | 1.1 | 1.0 | 1.0 |
| P054T | 1.0 | 1.1 | 1.0 | 1.0 | 1.0 | <0.9 | <0.9 |
| P054V | 1.1 | 1.1 | <0.9 | 1.0 | 1.1 | 1.1 | 1.6 |
| T055A | 1.0 | 1.0 | 1.0 | 0.9 | 1.2 | 1.3 | 1.2 |
| T055C | 1.1 | 1.0 | <0.9 | 0.9 | 0.9 | 1.1 | 1.1 |
| T055D | 1.1 | 1.1 | <0.9 | 1.0 | 1.2 | 1.5 | 1.4 |
| T055E | 1.1 | 1.1 | <0.9 | 0.9 | 1.0 | 1.3 | 1.4 |
| T055H | 1.0 | 1.0 | 1.0 | 0.9 | 1.2 | <0.9 | 0.9 |
| T055M | 1.0 | 1.0 | 1.1 | 0.9 | 1.1 | 1.2 | 0.9 |
| T055N | 1.1 | 1.0 | 0.9 | 0.9 | 1.1 | 0.9 | 0.9 |
| T055S | 1.0 | 0.9 | 0.9 | 0.9 | 1.2 | <0.9 | 0.9 |
| T055Y | 1.0 | 0.9 | 0.9 | <0.9 | 1.1 | <0.9 | <0.9 |
| A057D | 1.0 | 0.9 | 0.9 | 1.0 | 1.0 | 1.4 | 1.6 |
| A057E | 1.1 | 1.0 | 1.0 | 1.0 | 1.0 | 1.3 | 1.4 |
| A057H | 1.2 | 0.9 | 1.0 | 1.0 | 1.0 | 0.9 | 1.0 |
| A057M | 1.2 | 0.9 | 1.1 | 1.0 | 1.1 | 1.1 | 1.1 |
| A057N | 1.1 | 0.9 | 1.0 | 0.9 | 0.9 | 1.0 | 0.9 |
| A057Q | 1.1 | 1.0 | 1.1 | 0.9 | 1.0 | 0.9 | 1.0 |
| A057T | 1.1 | 0.9 | 1.0 | 1.0 | 1.0 | <0.9 | <0.9 |
| L059A | 1.0 | 1.1 | 1.0 | 1.1 | 0.9 | 1.5 | 1.2 |
| L059C | 1.0 | 1.0 | <0.9 | 0.9 | <0.9 | 1.7 | 1.3 |
| L059D | 0.9 | 1.2 | <0.9 | 1.0 | 1.0 | 1.9 | 1.6 |
| L059E | 1.0 | 1.3 | <0.9 | 1.0 | 1.0 | 1.6 | 1.4 |
| L059M | 1.0 | 1.0 | 1.1 | 1.1 | ND | 1.3 | 1.1 |
| L059N | 1.1 | 1.1 | 1.2 | 1.1 | 1.0 | 1.4 | 1.1 |
| L059Q | 1.0 | 1.0 | 0.9 | ND | 1.0 | 1.2 | 1.0 |
| L059T | 1.0 | 0.9 | <0.9 | 1.0 | 0.9 | 1.2 | 1.2 |
| N060S | 1.0 | 1.2 | <0.9 | 1.0 | 1.2 | 1.4 | 1.4 |
| T069S | 1.0 | 1.2 | 1.0 | 1.1 | 1.1 | <0.9 | 0.9 |
| S076A | 1.2 | 0.9 | <0.9 | 0.9 | 1.0 | 0.9 | 1.0 |
| S076D | 1.2 | 1.0 | <0.9 | 1.0 | 1.0 | 1.2 | 1.3 |
| S076E | 1.4 | 1.0 | <0.9 | 1.0 | 1.0 | 1.2 | 1.2 |
| S076F | 1.2 | 1.0 | 0.9 | 0.9 | 1.0 | 1.0 | 1.1 |
| S076H | 1.5 | 1.1 | ND | 1.0 | 1.0 | 0.9 | 0.9 |
| S076K | 1.3 | 0.9 | 1.0 | 1.0 | 1.1 | <0.9 | <0.9 |
| S076L | 1.3 | 0.9 | 1.1 | <0.9 | 1.1 | 1.0 | 1.0 |
| S076M | 1.5 | 1.0 | 0.9 | 1.0 | 1.0 | 1.0 | 1.1 |
| S076N | 1.4 | 1.0 | 1.0 | 1.0 | 1.1 | 1.1 | 1.0 |
| S076R | 1.2 | 1.0 | 1.2 | 1.0 | 1.0 | <0.9 | <0.9 |
| S076T | 1.4 | 1.1 | 1.0 | 0.9 | 1.0 | 1.0 | 1.0 |
| S076Y | 1.2 | 0.9 | <0.9 | 0.9 | 0.9 | 0.9 | <0.9 |
| V082A | 1.1 | 1.0 | 1.0 | 1.0 | 1.1 | 1.2 | 1.0 |
| P084D | 1.2 | 1.1 | 1.1 | 1.0 | <0.9 | 1.2 | 1.2 |
| P084F | 1.1 | 1.0 | 1.0 | 1.0 | 1.0 | 1.0 | 1,0 |

TABLE 4-continued

Stability, and Cleaning Performance in Laundry HDL and HDD BMI,
ADW EGG and Crème Brûlée of Bgi02446-S039E Variants.

| Amino acid substitutions relative to Bgi02446-S039E | Stability in EDTA with respect to Bgi02446-S039E | Laundry BMI Performance with respect to Bgi02446-S039E | | ADW EGG performance with respect to Bgi02446-S039E | | Crème Brûlée performance with respect to Bgi02446-S039E | |
|---|---|---|---|---|---|---|---|
| | | HDL Persil Non Bio Detergent | HDD Laundry Detergent | ADW Rinsed EGG Stain | ADW Unrinsed EGG Stain | GSM-B Detergent | MGDA Detergent |
| P084H | 1.4 | 1.0 | <0.9 | 1.0 | 0.9 | <0.9 | <0.9 |
| P084Y | 1.3 | 1.0 | 0.9 | 0.9 | 1.0 | <0.9 | <0.9 |
| N085S | 1.1 | 1.0 | 1.0 | 0.9 | 1.0 | 0.9 | 1.0 |
| G095A | 1.1 | 1.0 | 1.0 | 1.0 | 1.0 | <0.9 | 1.1 |
| G095N | 1.1 | 1.0 | 0.9 | 1.0 | 1.2 | <0.9 | <0.9 |
| A096M | 1.1 | 1.0 | 1.0 | ND | <0.9 | 1.1 | 1.1 |
| A096Q | 1.0 | 1.3 | 1.0 | 0.9 | 1.2 | 1.1 | 1.0 |
| N097E | 0.9 | 1.1 | <0.9 | 1.0 | 1.1 | 1.4 | 1.6 |
| N097H | 1.0 | 0.9 | 1.1 | 0.9 | <0.9 | 1.0 | 1.3 |
| N097K | 1.1 | 0.9 | <0.9 | 1.0 | 1.1 | <0.9 | 0.9 |
| S101T | 1.1 | 1.0 | <0.9 | 1.0 | 0.9 | <0.9 | <0.9 |
| V102L | 1.1 | 1.0 | <0.9 | 1.1 | 1.0 | <0.9 | 0.9 |
| V102M | 1.2 | 1.0 | 0.9 | 1.1 | 0.9 | <0.9 | 1.1 |
| G104A | 1.0 | 1.0 | 1.2 | 0.9 | <0.9 | 1.0 | 1.7 |
| G104D | 1.0 | 1.0 | <0.9 | <0.9 | <0.9 | 1.4 | 2.4 |
| G104H | 1.0 | 1.0 | <0.9 | 1.0 | <0.9 | 1.2 | 1.2 |
| G104M | 1.1 | 0.9 | 1.1 | 1.0 | 1.0 | <0.9 | 1.0 |
| G104N | 1.1 | 0.9 | 0.9 | 1.0 | 1.0 | 1.2 | 1.4 |
| G104T | 1.1 | 0.9 | <0.9 | 0.9 | 0.9 | 0.9 | 0.9 |
| G104V | 1.1 | 0.9 | <0.9 | 1.0 | <0.9 | 1.1 | 1.5 |
| G104W | 1.1 | <0.9 | 0.9 | 1.0 | <0.9 | <0.9 | 0.9 |
| G104Y | 1.0 | 0.9 | <0.9 | <0.9 | <0.9 | 1.0 | 1.2 |
| I105V | 1.1 | <0.9 | <0.9 | 0.9 | <0.9 | 0.9 | ND |
| Q107K | 1.0 | <0.9 | 0.9 | 1.0 | 1.2 | <0.9 | 0.9 |
| Q107M | 1.1 | 1.0 | 0.9 | 1.0 | 1.0 | 1.0 | 1.1 |
| E110L | 1.0 | <0.9 | <0.9 | <0.9 | 1.4 | <0.9 | <0.9 |
| A113T | 1.0 | 1.0 | <0.9 | 1.1 | 0.9 | 1.0 | ND |
| A113V | 1.1 | 1.0 | 0.9 | 1.0 | 0.9 | 1.0 | ND |
| T114V | 1.1 | <0.9 | 0.9 | 1.0 | 1.0 | <0.9 | 1.0 |
| N115E | 1.0 | 1.1 | <0.9 | ND | <0.9 | 1.0 | ND |
| N115H | 1.0 | 0.9 | 0.9 | 0.9 | 1.0 | 1.2 | ND |
| N115Q | 1.1 | 1.1 | 1.0 | 1.0 | <0.9 | 0.9 | ND |
| N116E | 1.1 | 1.1 | <0.9 | 1.0 | <0.9 | 1.1 | 1.4 |
| N116H | 1.1 | 0.9 | 0.9 | 0.9 | 0.9 | 1.0 | 1.1 |
| H118D | 1.1 | 1.0 | 1.0 | 1.1 | 1.0 | 1.0 | 1.1 |
| H118E | 1.2 | 0.9 | 0.9 | ND | <0.9 | 0.9 | 1.0 |
| H118N | 1.1 | 1.0 | 1.1 | 1.0 | 1.0 | 0.9 | 0.9 |
| A120V | 1.0 | 0.9 | <0.9 | 1.1 | 1.1 | <0.9 | 1.1 |
| M122L | 1.0 | 1.0 | 1.0 | 1.0 | 1.3 | <0.9 | 1.0 |
| F128G | 0.8 | 1.2 | <0.9 | 1.1 | 1.1 | 2.0 | 1.9 |
| P129A | 1.0 | 1.0 | <0.9 | 1.1 | 1.1 | 0.9 | ND |
| P129H | 1.0 | 1.1 | 0.9 | 1.1 | 1.3 | 1.1 | ND |
| P129N | 1.0 | 1.0 | 0.9 | 0.9 | 1.2 | <0.9 | ND |
| P129Y | 1.0 | 0.9 | <0.9 | <0.9 | 1.2 | <0.9 | ND |
| S131A | 1.2 | 0.9 | 1.3 | 0.9 | 1.1 | 0.9 | 0.9 |
| S131D | 1.1 | 1.2 | <0.9 | 0.9 | 0.9 | 1.6 | 1.7 |
| S131E | 1.1 | 1.1 | <0.9 | <0.9 | 1.0 | 1.6 | 1.7 |
| S131I | 1.1 | 0.9 | <0.9 | 1.0 | 1.0 | <0.9 | <0.9 |
| S131M | 1.1 | 0.9 | 1.3 | 0.9 | 1.2 | <0.9 | 1.0 |
| S131N | 1.1 | 1.0 | 1.1 | 0.9 | 1.1 | 0.9 | 0.9 |
| S131P | 1.1 | 0.9 | 1.1 | <0.9 | 1.1 | 0.9 | <0.9 |
| S131Q | 1.1 | 1.0 | 1.1 | 0.9 | 1.1 | 0.9 | <0.9 |
| S131T | 1.1 | 1.0 | 1.1 | 0.9 | 1.1 | 0.9 | 0.9 |
| S131V | 1.1 | 0.9 | 1.0 | 0.9 | 1.0 | <0.9 | <0.9 |
| L133M | 1.1 | <0.9 | 1.0 | 1.0 | 0.9 | 1.0 | <0.9 |
| R135A | 1.2 | 0.9 | <0.9 | 0.9 | <0.9 | 1.6 | 1.3 |
| R135E | 1.0 | 1.2 | ND | <0.9 | <0.9 | 1.3 | 1.3 |
| R135F | 1.0 | 1.2 | <0.9 | <0.9 | <0.9 | 1.3 | 1.0 |
| R135H | 1.1 | 1.2 | <0.9 | 1.0 | <0.9 | 1.6 | 1.4 |
| R135I | 1.1 | 1.2 | <0.9 | 0.9 | <0.9 | 1.6 | 1.2 |
| R135K | 1.1 | 1.1 | <0.9 | 1.0 | 0.9 | 1.3 | 0.9 |
| R135L | 1.1 | 1.0 | <0.9 | 0.9 | 1.0 | 2.2 | 1.2 |
| R135M | 1.2 | 1.1 | <0.9 | 0.9 | 1.0 | 1.6 | 1.2 |
| R135S | 1.1 | 1.2 | <0.9 | 0.9 | 0.9 | 1.7 | 1.4 |
| R135T | 1.1 | 1.2 | <0.9 | 1.0 | <0.9 | 1.5 | 1.3 |
| R135V | 1.1 | 1.2 | <0.9 | <0.9 | <0.9 | 1.6 | 1.0 |

TABLE 4-continued

Stability, and Cleaning Performance in Laundry HDL and HDD BMI, ADW EGG and Crème Brûlée of Bgi02446-S039E Variants.

| Amino acid substitutions relative to Bgi02446-S039E | Stability in EDTA with respect to Bgi02446-S039E | Laundry BMI Performance with respect to Bgi02446-S039E | | ADW EGG performance with respect to Bgi02446-S039E | | Crème Brûlée performance with respect to Bgi02446-S039E | |
|---|---|---|---|---|---|---|---|
| | | HDL Persil Non Bio Detergent | HDD Laundry Detergent | ADW Rinsed EGG Stain | ADW Unrinsed EGG Stain | GSM-B Detergent | MGDA Detergent |
| R135W | 1.1 | 1.0 | <0.9 | 0.9 | 0.9 | 1.7 | 1.0 |
| R135Y | 1.1 | 1.1 | <0.9 | <0.9 | <0.9 | 1.7 | 0.9 |
| A136M | 1.1 | 1.0 | 1.0 | 1.0 | 1.2 | <0.9 | <0.9 |
| V137L | 1.0 | 1.1 | <0.9 | 0.9 | 1.0 | <0.9 | ND |
| Y139E | 1.0 | 1.2 | 0.9 | 0.9 | 1.0 | 1.3 | ND |
| Y139S | 1.0 | 1.2 | 1.1 | 1.0 | 0.9 | 1.0 | ND |
| T141E | 1.0 | 1.3 | <0.9 | <0.9 | 0.9 | 1.3 | 1.6 |
| T141H | 1.0 | 1.2 | 0.9 | 0.9 | 0.9 | 0.9 | 1.0 |
| T141N | 1.0 | 1.1 | 1.1 | <0.9 | 1.0 | 0.9 | 1.1 |
| S142A | 1.1 | 0.9 | 1.0 | 0.9 | 1.0 | 1.0 | 1.0 |
| S142D | 1.1 | 1.1 | <0.9 | 0.9 | <0.9 | 1.2 | 1.3 |
| S142E | 1.1 | 1.0 | 0.9 | 1.0 | 0.9 | 1.3 | 1.3 |
| S142H | 1.2 | 1.0 | 0.9 | 1.0 | <0.9 | <0.9 | <0.9 |
| S142M | 1.2 | <0.9 | 1.0 | 0.9 | 1.0 | 1.0 | <0.9 |
| S142N | 1.1 | 1.0 | 1.3 | 1.0 | 1.1 | 1.1 | 0.9 |
| S142Q | 1.1 | 1.0 | 1.2 | 1.0 | 1.1 | 0.9 | 0.9 |
| R143E | 1.1 | 1.3 | <0.9 | 0.9 | <0.9 | 0.9 | 1.2 |
| R143H | 1.1 | 1.2 | <0.9 | 1.0 | 0.9 | 1.1 | 0.9 |
| R143M | 1.1 | 1.2 | 1.0 | 1.0 | 1.1 | <0.9 | <0.9 |
| R143N | 1.1 | 1.3 | 1.0 | 0.9 | 1.1 | <0.9 | <0.9 |
| R143Q | 1.1 | 1.2 | 0.9 | 1.0 | 0.9 | 1.0 | 1.1 |
| R143V | 1.0 | 1.2 | 0.9 | 1.0 | <0.9 | 0.9 | 0.9 |
| D144E | 1.0 | 1.0 | 1.2 | ND | 0.9 | 0.9 | 1.4 |
| D144N | 1.0 | 1.0 | 1.1 | 1.1 | 1.1 | <0.9 | 0.9 |
| V145C | 1.0 | 1.1 | 1.2 | 1.1 | 1.0 | 1.0 | 1.1 |
| V147C | 1.1 | <0.9 | 1.2 | <0.9 | <0.9 | 1.0 | 1.2 |
| I148L | 1.0 | 1.0 | <0.9 | 1.0 | 0.9 | 1.0 | 1.2 |
| I148V | 1.1 | 1.0 | <0.9 | 1.0 | <0.9 | 1.0 | 1.1 |
| A150M | 1.2 | ND | <0.9 | <0.9 | <0.9 | <0.9 | <0.9 |
| N154D | 1.0 | 1.0 | <0.9 | 1.0 | 0.9 | 1.4 | 2.1 |
| S156A | 1.0 | 1.1 | 1.0 | 0.9 | 1.0 | 1.1 | 1.3 |
| S156C | 1.0 | 1.1 | <0.9 | <0.9 | 0.9 | 1.3 | 1.8 |
| S156D | 0.9 | 1.1 | <0.9 | 0.9 | <0.9 | 1.5 | 2.1 |
| S156N | 1.1 | 0.9 | 1.1 | 0.9 | 0.9 | 1.1 | 1.1 |
| S156T | 1.1 | 1.0 | 1.0 | 1.0 | 0.9 | 1.1 | 1.0 |
| G157A | 1.1 | 0.9 | 1.1 | 1.0 | 1.2 | 0.9 | 0.9 |
| G157C | 1.1 | 1.0 | <0.9 | ND | 1.0 | 1.2 | 2.0 |
| G157D | 1.0 | 1.1 | <0.9 | 0.9 | 1.1 | 1.4 | 1.9 |
| G157E | 1.0 | 1.1 | <0.9 | ND | 0.9 | 1.6 | 2.1 |
| G157N | 1.1 | 1.0 | 0.9 | 1.0 | 1.0 | 1.0 | 1.1 |
| G157Q | 1.0 | 1.0 | 1.2 | 0.9 | 0.9 | 1.1 | 1.1 |
| S158A | 1.0 | 1.0 | 1.2 | 1.0 | 1.0 | 1.0 | 1.0 |
| S158C | 1.1 | 1.1 | <0.9 | 0.9 | 0.9 | 1.4 | 1.8 |
| S158F | 1.1 | ND | 0.9 | 0.9 | 0.9 | <0.9 | <0.9 |
| S158L | 1.1 | <0.9 | 1.0 | 1.0 | 0.9 | <0.9 | 1.3 |
| S158M | 1.1 | 0.9 | 1.1 | 1.0 | 1.0 | 1.0 | 0.9 |
| S158N | 1.1 | 0.9 | 1.2 | 1.0 | <0.9 | 1.0 | 1.0 |
| S158Q | 1.1 | 1.1 | 1.2 | 1.0 | 1.1 | 1.2 | 1.2 |
| S158T | 1.1 | 1.1 | 1.2 | 1.1 | 1.3 | 1.3 | 1.2 |
| S158V | 1.1 | 1.2 | 0.9 | 0.9 | 0.9 | 0.9 | 1.1 |
| S158W | 1.1 | <0.9 | <0.9 | 0.9 | <0.9 | <0.9 | <0.9 |
| S158Y | 1.2 | 1.0 | <0.9 | 1.0 | 1.0 | <0.9 | 1.4 |
| V159L | 1.1 | 1.0 | 1.0 | 1.1 | 0.9 | 1.2 | 1.4 |
| G160A | 1.3 | 0.9 | 1.2 | 1.0 | 1.0 | <0.9 | 1.0 |
| G160C | 1.1 | <0.9 | <0.9 | ND | 1.0 | <0.9 | 1.1 |
| G160D | 0.7 | 0.9 | <0.9 | 1.2 | 1.5 | <0.9 | <0.9 |
| G160M | 1.1 | 0.9 | 0.9 | 0.9 | 1.2 | <0.9 | <0.9 |
| G160S | 1.2 | 1.0 | 1.1 | ND | 1.2 | 0.9 | <0.9 |
| G160T | 1.1 | 0.9 | 0.9 | ND | <0.9 | 0.9 | 0.9 |
| Y161W | 1.0 | 1.1 | 1.0 | 1.0 | 1.0 | <0.9 | 1.1 |
| R164A | 1.0 | 1.0 | <0.9 | <0.9 | 0.9 | 1.6 | 2.6 |
| R164K | 1.0 | 1.0 | <0.9 | 1.0 | 0.9 | 1.2 | 1.3 |
| R164M | 1.0 | 1.1 | <0.9 | <0.9 | <0.9 | 1.4 | 2.3 |
| R164Q | 1.0 | 1.3 | < 0,9 | 0.9 | <0.9 | 1.4 | 2.0 |
| R164Y | 1.0 | 1.2 | <0.9 | 0.9 | <0.9 | 1.7 | 2.2 |
| A166D | 1.2 | 1.1 | ND | 0.9 | 1.1 | 1.4 | ND |

TABLE 4-continued

Stability, and Cleaning Performance in Laundry HDL and HDD BMI, ADW EGG and Crème Brûlée of Bgi02446-S039E Variants.

| Amino acid substitutions relative to Bgi02446-S039E | Stability in EDTA with respect to Bgi02446-S039E | Laundry BMI Performance with respect to Bgi02446-S039E | | ADW EGG performance with respect to Bgi02446-S039E | | Crème Brûlée performance with respect to Bgi02446-S039E | |
|---|---|---|---|---|---|---|---|
| | | HDL Persil Non Bio Detergent | HDD Laundry Detergent | ADW Rinsed EGG Stain | ADW Unrinsed EGG Stain | GSM-B Detergent | MGDA Detergent |
| A166E | 1.1 | 1.1 | <0.9 | 1.0 | 1.0 | 1.3 | ND |
| A166I | 1.0 | 1.0 | 1.0 | 1.0 | 1.1 | 0.9 | ND |
| A166P | 1.1 | 1.0 | 1.0 | 1.0 | 1.1 | <0.9 | ND |
| A166Q | 1.1 | 1.1 | 1.2 | 0.9 | 1.0 | 1.0 | ND |
| A166V | 1.0 | 1.1 | 1.1 | 0.9 | 0.9 | 1.0 | ND |
| N167E | 1.0 | 1.1 | <0.9 | 0.9 | <0.9 | 1.1 | ND |
| M169L | 1.0 | 1.0 | ND | 1.0 | 1.1 | 1.2 | 0.9 |
| A170G | 1.1 | 1.0 | 1.0 | 1.1 | 1.0 | 1.1 | 0.9 |
| T174V | 1.0 | 1.0 | 0.9 | 1.0 | 1.1 | 1.1 | <0.9 |
| Q176A | 1.0 | 1.0 | 1.2 | 1.0 | 1.0 | 1.1 | 1.1 |
| Q176C | 1.1 | 1.1 | <0.9 | 0.9 | <0.9 | 1.2 | 1.6 |
| Q176D | 1.0 | 1.2 | <0.9 | 0.9 | 1.0 | 2.1 | 1.4 |
| Q176E | 1.0 | 1.1 | <0.9 | 0.9 | 1.0 | 2.0 | 1.8 |
| Q176L | 1.0 | 1.0 | 1.0 | 1.1 | 1.0 | 0.9 | 1.1 |
| Q176M | 1.1 | 1.1 | 1.1 | 1.0 | 1.0 | 1.0 | 1.1 |
| Q176N | 1.0 | 1.1 | 1.0 | 0.9 | 1.0 | 1.3 | 1.1 |
| Q176S | 1.0 | 1.1 | 1.0 | 0.9 | 1.0 | 1.0 | 1.0 |
| N177A | 1.1 | 1.0 | 1.1 | 0.9 | 1.1 | 0.9 | 1.0 |
| N177C | 1.1 | 1.1 | <0.9 | <0.9 | 1.0 | 1.1 | 1.5 |
| N177D | 1.1 | 1.1 | <0.9 | 1.1 | 0.9 | 1.4 | 1.6 |
| N177E | 1.0 | 1.2 | <0.9 | <0.9 | 1.0 | 1.5 | 1.7 |
| N177G | 1.0 | 1.0 | 1.0 | 1.1 | 1.0 | 0.9 | 0.9 |
| N177H | 1.1 | 0.9 | 0.9 | 1.0 | 1.0 | 0.9 | <0.9 |
| N177K | 1.0 | <0.9 | <0.9 | 1.0 | 1.1 | <0.9 | <0.9 |
| N177L | 1.1 | 0.9 | 1.0 | 1.0 | 1.1 | 0.9 | <0.9 |
| N177M | 1.2 | <0.9 | 1.1 | <0.9 | 1.2 | 0.9 | 0.9 |
| N177Q | 1.1 | 1.0 | 1.2 | 0.9 | 1.1 | 1.0 | 0.9 |
| N177S | 1.0 | 1.0 | 1.0 | 1.1 | 1.2 | 0.9 | <0.9 |
| N177W | 1.1 | <0.9 | <0.9 | 0.9 | 1.0 | <0.9 | <0.9 |
| N177Y | 1.1 | 0.9 | <0.9 | <0.9 | 1.2 | 1.0 | <0.9 |
| N178D | 1.0 | 1.0 | <0.9 | 1.0 | 0.9 | 1.5 | 1.8 |
| R179A | 1.0 | 1.1 | <0.9 | <0.9 | 1.1 | 1.9 | 1.5 |
| R179C | 1.0 | 1.0 | <0.9 | <0.9 | 0.9 | 1.9 | 1.6 |
| R179E | 1.0 | 1.1 | <0.9 | <0.9 | 1.0 | 2.0 | 2.0 |
| R179F | 1.0 | 1.0 | <0.9 | ND | 0.9 | 1.5 | 1.7 |
| R179G | 1.0 | 1.0 | <0.9 | 0.9 | 1.1 | 1.7 | 1.7 |
| R179H | 1.0 | 1.1 | <0.9 | <0.9 | 1.0 | 1.6 | 1.6 |
| R179I | 1.0 | 1.1 | <0.9 | <0.9 | 1.1 | 1.9 | 1.8 |
| R179K | 1.0 | 1.0 | <0.9 | <0.9 | 1.2 | 1.4 | 1.3 |
| R179M | 1.1 | 1.0 | <0.9 | <0.9 | 0.9 | 1.5 | 1.4 |
| R179Q | 1.1 | 1.1 | <0.9 | 1.0 | 1.0 | 1.8 | 1.7 |
| R179S | 1.0 | 1.1 | <0.9 | ND | 1.0 | 1.8 | 1.6 |
| R179V | 1.0 | 1.2 | <0.9 | 1.0 | 1.0 | 1.9 | 1.9 |
| R179W | 1.0 | 1.2 | <0.9 | 0.9 | ND | 1.5 | 1.5 |
| R179Y | 1.0 | ND | <0.9 | <0.9 | 1.0 | 1.9 | 1.8 |
| R180K | 1.1 | 1.1 | 1.0 | 0.9 | 1.0 | 1.2 | 0.9 |
| N182A | 1.1 | 1.0 | 1.0 | 0.9 | 1.1 | 0.9 | <0.9 |
| N182C | 1.1 | 1.0 | <0.9 | <0.9 | 1.0 | <0.9 | 1.3 |
| N182D | 1.0 | 1.1 | <0.9 | 1.0 | 1.2 | 1.7 | 1.5 |
| N182E | 1.1 | 1.1 | <0.9 | 1.0 | 1.0 | 1.5 | 1.6 |
| N182G | 1.1 | 0.9 | 0.9 | 1.0 | 1.0 | 1.0 | 1.1 |
| N182H | 1.1 | 0.9 | 1.0 | 0.9 | <0.9 | <0.9 | 0.9 |
| N182I | 1.1 | 0.9 | <0.9 | 1.0 | 1.0 | <0.9 | 0.9 |
| N182K | 1.1 | <0.9 | <0.9 | 1.0 | 1.0 | <0.9 | <0.9 |
| N182L | 1.1 | 0.9 | <0.9 | <0.9 | 1.1 | <0.9 | 1.0 |
| N182P | 1.2 | 1.1 | 1.1 | 1.0 | 0.9 | <0.9 | 1.0 |
| N182Q | 1.1 | 1.1 | 1.1 | 1.0 | 0.9 | 1.0 | 1.1 |
| N182S | 1.2 | 1.1 | 1.0 | 1.1 | 0.9 | 1.0 | 1.1 |
| N182T | 1.1 | 1.1 | 1.0 | 0.9 | <0.9 | 1.0 | 1.1 |
| N182V | 1.1 | 1.0 | 0.9 | 1.0 | 0.9 | <0.9 | 1.0 |
| N182W | 1.2 | <0.9 | <0.9 | 0.9 | <0.9 | <0.9 | <0.9 |
| N182Y | 1.2 | <0.9 | <0.9 | 1.1 | 1.0 | <0.9 | 1.1 |
| Y186F | 1.0 | 1.0 | 1.2 | 1.0 | 0.9 | 1.0 | 1.1 |
| T188A | 1.1 | 1.0 | 0.9 | 0.9 | 1.0 | <0.9 | 0.9 |
| T188C | 1.1 | 1.1 | <0.9 | 0.9 | 0.9 | 1.2 | 1.5 |
| T188D | 1.1 | 1.2 | 0.9 | 1.0 | 0.9 | 1.4 | 1.3 |

TABLE 4-continued

Stability, and Cleaning Performance in Laundry HDL and HDD BMI,
ADW EGG and Crème Brûlée of Bgi02446-S039E Variants.

| Amino acid substitutions relative to Bgi02446-S039E | Stability in EDTA with respect to Bgi02446-S039E | Laundry BMI Performance with respect to Bgi02446-S039E | | ADW EGG performance with respect to Bgi02446-S039E | | Crème Brûlée performance with respect to Bgi02446-S039E | |
|---|---|---|---|---|---|---|---|
| | | HDL Persil Non Bio Detergent | HDD Laundry Detergent | ADW Rinsed EGG Stain | ADW Unrinsed EGG Stain | GSM-B Detergent | MGDA Detergent |
| T188E | 1.2 | 1.2 | <0.9 | 1.0 | 0.9 | 1.4 | 1.4 |
| T188I | 1.1 | 1.1 | 0.9 | 0.9 | 1.0 | 0.9 | <0.9 |
| T188L | 1.1 | 1.0 | 1.0 | 0.9 | 1.0 | 0.9 | <0.9 |
| T188M | 1.1 | 0.9 | 1.1 | 0.9 | 1.2 | 0.9 | 0.9 |
| T188N | 1.1 | 1.1 | 1.0 | 1.0 | 1.1 | 0.9 | 0.9 |
| T188Q | 1.1 | 1.1 | 1.0 | 1.0 | 1.0 | 0.9 | 0.9 |
| T188S | 1.0 | 1.1 | ND | 0.9 | 1.1 | 0.9 | <0.9 |
| T188V | 1.1 | 1.1 | 1.0 | 1.0 | 1.0 | 0.9 | <0.9 |
| T188W | 1.1 | <0.9 | <0.9 | 0.9 | 1.0 | <0.9 | <0.9 |
| T188Y | 1.1 | 1.0 | <0.9 | <0.9 | ND | 0.9 | <0.9 |
| G189C | 1.0 | 1.0 | <0.9 | <0.9 | <0.9 | 1.4 | 1.4 |
| G189D | 1.1 | 1.0 | <0.9 | 0.9 | <0.9 | 1.3 | 1.5 |
| G189E | 1.0 | 1.0 | <0.9 | 0.9 | 0.9 | 1.3 | 1.8 |
| I190M | 1.0 | 1.4 | 1.2 | 0.9 | 1.0 | 0.9 | 0.9 |
| D191E | 1.0 | 1.0 | 1.0 | 1.0 | 0.9 | 0.9 | 1.1 |
| I192C | 1.1 | 0.9 | 1.0 | 1.0 | 1.0 | 0.9 | 1.1 |
| I192M | 1.1 | 1.0 | 1.0 | 1.0 | 1.0 | 0.9 | 1.1 |
| V193A | 1.0 | 1.0 | 1.0 | 1.0 | 1.0 | 1.5 | 1.3 |
| V193M | 1.1 | 1.1 | 1.0 | 0.9 | 1.1 | 1.2 | 1.4 |
| N198D | 1.0 | 1.2 | <0.9 | 1.0 | 1.1 | 1.9 | 1.7 |
| N198E | 1.0 | 1.0 | <0.9 | 0.9 | <0.9 | 1.8 | 1.6 |
| Q200H | 1.1 | 0.9 | 1.0 | 0.9 | 0.9 | 0.9 | 1.0 |
| Q200I | 1.3 | <0.9 | <0.9 | 0.9 | <0.9 | 0.9 | 0.9 |
| Q200K | 1.2 | <0.9 | <0.9 | 0.9 | 1.0 | <0.9 | <0.9 |
| Q200M | 1.2 | 0.9 | 1.0 | 0.9 | 1.0 | 1.0 | 1.1 |
| Q200V | 1.1 | 0.9 | 0.9 | 1.0 | 0.9 | 0.9 | 0.9 |
| Q200Y | 1.3 | 0.9 | <0.9 | 1.0 | 0.9 | 1.0 | 1.1 |
| R207K | 1.0 | 1.2 | <0.9 | ND | 0.9 | 1.1 | 1.3 |
| R207L | 1.0 | 1.1 | <0.9 | 1.1 | 1.0 | 1.5 | 1.9 |
| R207N | 0.9 | 1.3 | <0.6 | 1.0 | 0.9 | 1.8 | 1.6 |
| R207Q | 0.9 | 1.3 | <0.9 | 1.0 | 0.9 | 1.7 | 1.6 |
| R207T | 0.6 | 1.2 | <0.9 | 1.0 | 0.9 | 1.6 | 1.7 |
| V209P | 1.1 | 1.1 | 1.1 | 1.0 | 0.9 | 1.4 | 1.2 |
| S210C | 1.0 | 1.0 | <0.9 | 0.9 | <0.9 | 1.0 | 1.3 |
| S210D | 0.9 | 1.1 | <0.9 | ND | 0.9 | 1.8 | 1.6 |
| S210E | 1.1 | 1.2 | <0.9 | 1.2 | 0.9 | 1.7 | 1.7 |
| S210F | 1.2 | <0.9 | <0.9 | 1.0 | 0.9 | <0.9 | 0.9 |
| S210G | 1.0 | 1.0 | 1.0 | 1.1 | 1.0 | <0.9 | 1.0 |
| S210L | 1.0 | <0.9 | <0.9 | 1.0 | 1.0 | 0.9 | 1.2 |
| S210N | 0.9 | 1.0 | <0.9 | 1.0 | 1.0 | 1.2 | 1.4 |
| S210P | 1.2 | 1.0 | 0.9 | 1.0 | 1.0 | 0.9 | 0.9 |
| S210Q | 1.0 | 0.9 | 0.9 | 1.1 | 0.9 | 0.9 | 1.1 |
| S210Y | 1.0 | <0.9 | <0.9 | 0.9 | 1.0 | 0.9 | 1.2 |
| M211E | 0.6 | 1.2 | 0.9 | 1.1 | 1.4 | 1.7 | 1.6 |
| M211K | 1.1 | <0.9 | <0.9 | 1.0 | <0.9 | 0.9 | 1.3 |
| M211L | 1.0 | 1.0 | 1.0 | 1.0 | 0.9 | 1.1 | 1.9 |
| M211Q | 0.9 | 1.1 | 1.4 | 1.2 | 1.1 | 1.3 | 1.3 |
| M211R | 1.0 | 0.9 | <0.9 | 1.1 | 1.1 | <0.9 | <0.9 |
| N212A | 1.0 | 1.0 | 1.3 | <0.9 | 0.9 | <0.9 | 1.0 |
| N212C | 1.0 | 0.9 | <0.9 | <0.9 | <0.9 | <0.9 | 1.3 |
| N212Q | 0.9 | 0.9 | 0.9 | 1.0 | <0.8 | 1.2 | 1.2 |
| N212S | 1.2 | 1.1 | 0.9 | 0.9 | 0.9 | <0.9 | 1.0 |
| T218C | 1.1 | 1.0 | 0.9 | 1.0 | 1.0 | 0.9 | 0.9 |
| T218S | 1.2 | 1.0 | <0.9 | 1.0 | 1.1 | <0.9 | <0.9 |
| A224V | 1.0 | 0.9 | 1.1 | 1.0 | 1.0 | 0.9 | 0.9 |
| L227M | 1.0 | 1.0 | 0.9 | 1.0 | 1.1 | 1.0 | 0.9 |
| L227Q | 1.0 | 1.0 | 1.1 | 0.9 | 1.0 | 0.9 | 0.9 |
| V228L | 1.1 | ND | 0.9 | 0.9 | ND | 1.0 | 1.2 |
| Q230E | 1.2 | 1.1 | <0.9 | 0.9 | 1.1 | 1.2 | 1.2 |
| R231C | 1.1 | 1.0 | <0.9 | 0.9 | <0.9 | 1.2 | 1.2 |
| R231E | 1.1 | 1.1 | <0.9 | 0.9 | <0.9 | 1.1 | 1.3 |
| R231H | 1.1 | 1.1 | <0.9 | 0.9 | <0.9 | 1.1 | 1.1 |
| R231I | 1.0 | 1.2 | <0.9 | 1.0 | <0.9 | 1.0 | 1.0 |
| R231L | 1.0 | 0.9 | <0.9 | 0.9 | 1.0 | 1.1 | 1.2 |
| R231N | 1.1 | 1.1 | <0.9 | <0.9 | 1.0 | 1.1 | 1.2 |
| R231Q | 1.0 | 1.0 | 1.0 | 0.9 | 1.0 | 1.0 | 1.2 |

TABLE 4-continued

Stability, and Cleaning Performance in Laundry HDL and HDD BMI, ADW EGG and Crème Brûlée of Bgi02446-S039E Variants.

| Amino acid substitutions relative to Bgi02446-S039E | Stability in EDTA with respect to Bgi02446-S039E | Laundry BMI Performance with respect to Bgi02446-S039E | | ADW EGG performance with respect to Bgi02446-S039E | | Crème Brûlée performance with respect to Bgi02446-S039E | |
|---|---|---|---|---|---|---|---|
| | | HDL Persil Non Bio Detergent | HDD Laundry Detergent | ADW Rinsed EGG Stain | ADW Unrinsed EGG Stain | GSM-B Detergent | MGDA Detergent |
| R231S | 1.0 | 1.2 | <0.9 | <0.9 | 1.0 | 1.0 | 1.1 |
| R231T | 1.1 | 1.0 | <0.9 | 0.9 | 0.9 | 0.9 | 1.0 |
| Y232F | 1.1 | 1.0 | 1.2 | 1.1 | 0.9 | 1.0 | 1.2 |
| Y232H | 1.1 | 0.9 | 1.0 | 1.0 | 1.0 | 0.9 | 1.0 |
| Y232Q | 1.0 | 1.0 | 1.3 | 1.0 | <0.9 | 0.9 | 1.0 |
| Y232R | 1.0 | <0.9 | 1.4 | 1.0 | <0.9 | <0.9 | <0.9 |
| Y232W | 1.0 | ND | 0.9 | 1.1 | <0.9 | 0.9 | 1.0 |
| S234A | 1.0 | 1.0 | 1.2 | 1.0 | 0.9 | <0.9 | 1.1 |
| S234D | 1.1 | 1.1 | <0.9 | 0.9 | 0.9 | 0.9 | 1.2 |
| S234E | 1.0 | 1.0 | <0.9 | 0.9 | 1.0 | 1.0 | 1.2 |
| S234M | 1.1 | 1.0 | 1.0 | 1.0 | 1.0 | <0.9 | 1.1 |
| S234T | 1.0 | 1.0 | 0.9 | 1.0 | 0.9 | <0.9 | 1.2 |
| S234W | 1.0 | <0.9 | <0.9 | 1.0 | 0.9 | <0.9 | 1.2 |
| S234Y | 1.0 | 0.9 | <0.9 | 0.9 | 0.9 | <0.9 | 1.3 |
| N236D | 1.1 | 1.2 | 1.0 | 0.9 | ND | 1.2 | 1.2 |
| N236G | 1.0 | 1.0 | 0.9 | 0.9 | ND | 1.0 | 1.1 |
| N236S | 1.0 | 1.1 | 1.0 | 1.0 | ND | 1.0 | 1.1 |
| N236T | 1.0 | 1.0 | 1.0 | 0.9 | ND | 1.1 | 1.1 |
| T238A | 1.1 | 1.0 | 1.1 | 1.0 | 0.9 | 0.9 | 1.5 |
| T238D | 1.1 | 1.1 | <0.9 | 1.0 | 0.9 | 1.2 | 1.7 |
| T238E | 1.1 | 1.1 | <0.9 | 0.9 | 0.9 | 1.4 | 1.4 |
| T238M | 1.1 | 0.9 | 1.1 | 1.0 | 1.0 | 1.0 | 1.4 |
| T238V | 1.1 | 1.0 | 1.0 | 1.0 | 1.0 | 1.1 | 1.2 |
| Q239D | 1.0 | 1.1 | <0.9 | <0.9 | <0.9 | 1.2 | 1.6 |
| Q239E | 1.1 | 0.9 | <0.9 | <0.9 | <0.9 | 1.1 | 1.5 |
| Q239L | 1.1 | <0.9 | <0.9 | 1.0 | <0.9 | 0.9 | 1.1 |
| Q239M | 1.1 | 1.0 | 1.0 | 0.9 | 1.0 | 1.2 | 1.3 |
| Q239N | 1.0 | 0.9 | 1.0 | 1.0 | <0.9 | 1.0 | 1.2 |
| Q239T | 1.1 | 1.0 | <0.9 | 0.9 | <0.9 | 1.0 | 1.0 |
| N242A | 1.1 | 1.0 | 0.9 | 1.0 | 1.0 | <0.9 | 1.0 |
| K245E | 1.0 | 0.9 | <0.9 | 0.9 | <0.9 | 1.4 | 1.7 |
| N246A | 1.1 | 1.0 | 1.0 | 1.0 | 0.9 | 1.0 | 1.3 |
| N246L | 1.1 | 1.0 | 1.0 | ND | 0.9 | 1.3 | 1.1 |
| N246S | 1.1 | 1.1 | 0.9 | 0.9 | 0.9 | 0.9 | 1.0 |
| T247E | 1.0 | 1.0 | <0.9 | <0.9 | ND | 1.1 | 1.4 |
| T247Q | 1.0 | 0.9 | <0.9 | 1.0 | <0.9 | 0.9 | 1.2 |
| T249C | 1.0 | 1.0 | <0.9 | 1.0 | <0.9 | 1.0 | 1.6 |
| T249D | 1.0 | 1.1 | <0.9 | 0.9 | <0.9 | 1.2 | 1.5 |
| T249E | 1.1 | 1.1 | <0.9 | 0.9 | <0.9 | 1.3 | 1.4 |
| T249F | 1.1 | 1.0 | 1.0 | 1.0 | 0.9 | 1.0 | <0.9 |
| T249I | 1.1 | 1.0 | 1.0 | 1.0 | 1.0 | <0.9 | 1.0 |
| T249L | 1.1 | 0.9 | 0.9 | 1.0 | 0.9 | 1.0 | 1.2 |
| T249S | 1.1 | 1.0 | 1.0 | 1.0 | 1.0 | 0.9 | 0.9 |
| T249Y | 1.1 | 1.0 | <0.9 | ND | 0.9 | 1.0 | 1.4 |
| N250D | 1.1 | 1.1 | <0.9 | 0.9 | 0.9 | 1.3 | 1.6 |
| N250S | 1.1 | 1.0 | 0.9 | 1.0 | 0.9 | 1.1 | 1.2 |
| N250T | 1.0 | 1.1 | 1.1 | 1.0 | 0.9 | 0.9 | 1.1 |
| N253D | 1.2 | 1.0 | <0.9 | 0.9 | 1.1 | 1.5 | 1.7 |
| N253E | 1.1 | 1.1 | <0.9 | 1.0 | 0.9 | 1.5 | 1.7 |
| N253P | 1.0 | 1.0 | 0.9 | 1.0 | 1.0 | 1.1 | 1.1 |
| S254P | 1.1 | 1.0 | 1.1 | 1.0 | 1.1 | 1.0 | 0.9 |
| S254Y | 1.0 | 1.0 | <0.9 | ND | 0.9 | 1.2 | <0.9 |
| S255A | 1.0 | 0.9 | 1.0 | 0.9 | 1.0 | 1.1 | 1.2 |
| S255C | 1.2 | 0.9 | <0.9 | 1.0 | 1.0 | 1.2 | 2.0 |
| S255D | 1.1 | 1.0 | <0.9 | 0.9 | 0.9 | 1.3 | 1.9 |
| S255E | 1.2 | 1.1 | <0.9 | 0.9 | 1.0 | 1.3 | 1.8 |
| S255F | 1.1 | 0.9 | 1.0 | 0.9 | 0.9 | <0.9 | 0.9 |
| S255I | 1.1 | 1.0 | 0.9 | 0.9 | 0.9 | 0.9 | 1.0 |
| S255M | 1.1 | 0.9 | 1.0 | 0.9 | 1.1 | 1.0 | 1.1 |
| S255N | 1.0 | 0.9 | 1.2 | 1.0 | 0.9 | 0.9 | 1.0 |
| S255V | 1.1 | 1.0 | 0.9 | 1.0 | 0.9 | 1.1 | 1.0 |
| S255W | 1.1 | <0.9 | <0.9 | <0.9 | 0.9 | <0.9 | <0.9 |
| Q256C | 1.1 | 1.0 | <0.9 | ND | 0.9 | 1.4 | 1.8 |
| Q256E | 1.1 | 1.1 | <0.9 | 1.0 | 0.9 | 1.4 | 1.8 |
| Q256F | 1.1 | 1.0 | <0.9 | 0.9 | 1.0 | <0.9 | 1.0 |
| Q256H | 1.1 | 1.0 | 1.0 | 1.0 | 1.0 | 1.0 | 1.1 |

TABLE 4-continued

Stability, and Cleaning Performance in Laundry HDL and HDD BMI, ADW EGG and Crème Brûlée of Bgi02446-S039E Variants.

| Amino acid substitutions relative to Bgi02446-S039E | Stability in EDTA with respect to Bgi02446-S039E | Laundry BMI Performance with respect to Bgi02446-S039E | | ADW EGG performance with respect to Bgi02446-S039E | | Crème Brûlée performance with respect to Bgi02446-S039E | |
|---|---|---|---|---|---|---|---|
| | | HDL Persil Non Bio Detergent | HDD Laundry Detergent | ADW Rinsed EGG Stain | ADW Unrinsed EGG Stain | GSM-B Detergent | MGDA Detergent |
| Q256L | 1.0 | 1.1 | 0.9 | 0.9 | 1.2 | 1.1 | 0.9 |
| Q256M | 1.0 | 0.9 | 1.2 | 1.0 | 1.1 | <0.9 | 1.0 |
| Q256W | 1.1 | 1.0 | <0.9 | 0.9 | 1.0 | 1.0 | 0.9 |
| Q256Y | 1.1 | 0.9 | <0.9 | 0.9 | 1.2 | 1.4 | <0.9 |
| F257C | 1.0 | 1.0 | <0.9 | <0.9 | <0.9 | 1.2 | 1.5 |
| F257M | 1.0 | 1.0 | 1.1 | 1.0 | 1.0 | 1.0 | 1.0 |
| S259D | 1.0 | 1.0 | <0.9 | 1.0 | <0.9 | 1.3 | 1.5 |
| S259E | 0.9 | 1.0 | <0.9 | 0.9 | <0.9 | 1.3 | 1.4 |
| S259M | 1.0 | 0.9 | 1.2 | 1.0 | 1.0 | 1.1 | 1.1 |
| S259N | 1.0 | 1.0 | 0.9 | 1.0 | 1.0 | 1.1 | 1.1 |
| V262L | 1.0 | 0.9 | <0.9 | 1.0 | 1.0 | 1.4 | 1.1 |
| N263D | 1.0 | 1.1 | <0.9 | 1.0 | 0.9 | 1.2 | 1.1 |
| N263Q | 1.0 | 0.9 | 1.0 | 0.9 | 1.1 | <0.9 | 0.9 |
| A264T | 1.1 | 1.1 | 1.0 | 0.9 | 1.0 | 1.1 | 0.9 |
| E265A | 1.0 | <0.9 | 1.1 | 1.0 | 1.1 | <0.9 | <0.9 |
| E265M | 1.0 | <0.9 | 1.3 | 0.9 | 1.1 | <0.9 | <0.9 |
| E265N | 1.0 | <0.9 | 1.3 | <0.9 | 1.0 | <0.9 | <0.9 |
| E265Q | 1.0 | <0.9 | 1.1 | 0.9 | 1.1 | <0.9 | <0.9 |
| A266L | 1.1 | 1.0 | <0.9 | 1.0 | 1.0 | 0.9 | <0.9 |
| A266M | 1.1 | 0.9 | 0.9 | 1.0 | 1.0 | <0.9 | 1.1 |
| A266N | 1.1 | 1.0 | 1.0 | <0.9 | 0.9 | 0.9 | <0.9 |
| A266Q | 1.0 | 0.9 | 1.1 | 0.9 | 0.9 | <0.9 | <0.9 |
| A266R | 1.0 | <0.9 | 1.3 | 0.9 | 0.9 | <0.9 | <0.9 |
| T268A | 1.0 | 0.9 | 1.0 | 0.9 | 1.1 | 1.0 | 1.2 |
| T268C | 1.1 | 1.0 | 0.9 | 1.0 | 1.0 | 1.0 | 1.2 |
| T268D | 1.0 | 1.1 | 0.9 | 0.9 | <0.9 | 1.0 | 1.4 |
| T268E | 0.9 | 1.1 | <0.9 | 0.9 | <0.9 | 1.1 | 1.4 |
| R269H | 1.0 | 1.1 | <0.9 | 0.9 | <0.9 | 1.2 | 1.5 |
| R269P | 1.0 | 1.0 | <0.9 | 0.9 | <0.9 | 1.1 | 1.3 |
| R269W | 1.0 | 0.9 | <0.9 | <0.9 | <0.9 | 0.9 | 1.4 |

The following variants showed improved performance index (PI value of ≥1.1) compared to parent enzyme Bgi02446-S039E on one of the following assays: BMI HDL cleaning, BMI HDD cleaning, PAS-38 ADW cleaning, Crème brûlée ADW cleaning, or stability in Tris-EDTA buffer: T003V, V004T, I008V, T009A/C/E/G/H/K/M/N/Q/S/W/Y, R010A/K/M/N/Q/W, V011A/I/S/T, Q012A/C/D/E/G/M/N/R/S/T/V/W, P014D, A015D/E/F/H/I/K/M/P/Q/V/W/Y, V016L/M/S, H017C/E/F/G/I/L/N/V/W/Y, N018A/C/D/E/F/G/L/M/Q/T, R019A/C/D/E/F/H/I/K/L/N/Q/S/T/W/Y, G020A/C/D/M/N/T, S024A/E, G025A/C/D/E/M/N, V026A/I, R027K, S033T, S036A/C/E/I/L/M/Q/T/V, N042C/D/E/M/Q, 1043L, R044C/E/F/G/H/I/K/L/N/Q/S/T/V/W/Y, A047I/Y, V0S0I, G052A/C/D/H/L/M/N/S/T/Y, P054A/C/G/L/M/N/T/V, T055A/C/D/E/H/M/N/S/Y, A057D/E/H/M/N/Q/T, L059A/C/D/E/M/N/Q/T, N060S, T069S, S076A/D/E/F/H/K/L/M/N/R/T/Y, V082A, P084D/F/H/Y, N085S, G095A/N, A096M/Q. N097E/H/K, S101T, V102L/M, G104A/D/H/M/N/T/V/W/Y, 110SV, Q107K/M, E110L, A113T/V, T114V, NIISE/H/Q, N116E/H, H118D/E/N, A120V, M122L, F128G, P129A/H/N/Y, S131A/D/E/I/M/N/P/Q/T/V, L133M, R135A/E/F/H/I/K/L/M/S/T/V/W/Y, A136M, V137L, Y139E/S, T141E/H/N, S142A/D/E/H/M/N/Q, R143E/H/M/N/Q/V, D144E/N, V145C, V147C, 1148L/V, A150M, N154D, S156A/C/D/N/T, G157A/C/D/E/N/Q, S158A/C/F/L/M/N/Q/T/V/W/Y, V159L, G160A/C/D/M/S/T, Y161W, R164A/K/M/Q/Y, A166D/E/I/P/Q/V, N167E, M169L, A170G, T174V, Q176A/C/D/E/L/M/N/S, N177A/C/D/E/G/H/K/L/M/Q/S/W/Y, N178D, R179A/C/E/F/G/H/I/K/M/Q/S/V/W/Y, R180K, N182A/C/D/E/G/H/I/K/L/P/Q/S/T/V/W/Y, Y186F, T188A/C/D/E/I/L/M/N/Q/S/V/W/Y, G189C/D/E, 1190M, D191E, 1192C/M, V193A/M, N198D/E, Q200H/I/K/M/V/Y, R207K/L/N/Q/T, V209P, S210C/D/E/F/G/L/N/P/Q/Y, M211E/K/L/Q/R, N212A/C/Q/S, T218C/S, A224V, L227M/Q, V228L, Q230E, R231C/E/H/I/L/N/Q/S/T, Y232F/H/Q/R/W, S234A/D/E/M/T/W/Y, N236D/G/S/T, T238A/D/E/M/V, Q239D/E/L/M/N/T, N242A, K245E, N246A/L/S, T247E/Q, T249C/D/E/F/I/L/S/Y, N250D/S/T, N253D/E/P, S254P/Y, S255A/C/D/E/F/I/M/N/V/W, Q256C/E/F/H/L/M/W/Y, F257C/M, S259D/E/M/N, V262L, N263D/Q, A264T, E265A/M/N/Q, A266L/M/N/Q/R, T268A/C/D/E, and R269H/P/W.

The following variants showed improved HDL cleaning performance index (PI value of ≥1.1) compared to parent enzyme Bgi02446-S039E on BMI stain: I008V, V011S, Q012A/C/D/E/G/M/N/S/T/V, P014D, V016M, H017C/I/N/W, N018T, R019A/D/F/H/I/L/Q/S/W/Y, S024A/E, G025M/N, N042D/E/M, R044E/G/I/N/T, G052T, P054T/V, TO55E, L059D/E, N060S, T069S, A096Q, N115E, F128G, P129H, S131D, R.135E/F/H/I/S/T/V, V137L, Y139E/S, T141E/H/N, R143E/H/M/N/Q/V, S156C, G157D/E, S158C/T/V, Y161W, R164M/Q/Y, A166V, N167E, Q176D/E/M/N/S, N177C/E, R179I/S/V/W, N182D/E/P/Q/T, T188D/E/S/V, 1190M, V193M, N198D, R207K/N/T, S210D/E, M211E/Q, R231I/S, S234D, N236D, T238D, N246S, T249D, N250D/T, and R269H.

The following variants showed improved HDD cleaning performance index (PI value of ≥1.1) compared to parent enzyme Bgi02446-S039E on BMI stain: T003V, T009Q/W, Q012R/W, A015M/Q, V016M, S024A, N042M, P054N, A057M/Q, L059N, S076R, G104A, S131A/M/P/Q, S142N/Q, D144E, V145C, V147C, G157A/Q. S158A/N/Q/T, G160A, A166Q, Q176A, N177Q, Y186F, I190M, M211Q, N212A, A224V, L227Q, Y232F/Q/R, S234A, T238A, S255N, Q256M, F257M, S259M, E265M/N/Q, and A266Q/R.

The following variants showed improved ADW cleaning performance index (PI value of ≥1.1) compared to parent enzyme Bgi02446-S039E on one of the PAS-38 assays: T009H/K/N/W, V011A/I, Q012A/M/N/R/S/V, A015F/I/K/V, V016L/M, H017F/G/I/L/N/V/W, N018F, R019C/K/L/Q, G020A/D/M/N/T, S024A, G025A/D/N, S036A/L, G052D/H, P0S4A/G/L/M/V, T055A/D/H/S/Y, L059A/M/N, N060S, T069S, S076K/L, G095N, A096Q, N097K, V102L/M, Q107K, E110L, A113T, H118D, A120V, M122L, F128G, P129A/H/N/Y, S131M/N/P, A136M, R143N, D144N, V145C, G157A/D, S158Q/T, V159L, G160D/M/S, A166I, A170G, Q176L, N177A/D/G/K/L/M/S/Y, R179A/K, N182A/E/D/S/Y, T188M, D191E, R207L, S210E/G/Q, M211E/Q/R, T218S, L227M, Y232F/W, Q256L/Y, N263Q, E265A/M/Q, and T268A.

The following variants showed improved ADW cleaning performance index (PI value of ≥1.1) compared to parent enzyme Bgi02446-S039E on one of the Crème Brûlée assays: T009A/C/E/M/N/Y, R010A/K/M/N/Q/W, V011A/T, Q012A/C/D/E/M, P014D, A015D/E/H/I/M/V/W/Y, V016L/M, H017C/E, N018C/D/E/M, R019A/C/D/E/F/H/I/K/L/N/Q/S/T/W/Y, G020C/D, S024A/E, G025A/C/D/E/M/N, V026A, R027K, S036C/E/Q/V, N042C/D/E, I043L, R044C/E/G/H/I/L/N/Q/S/T, G052A/C/D/L/M/N, P054A/C/L/M/V, T055A/C/D/E/M, A057D/E, L059A/C/D/E/M/N/Q/T, N060S, S076D/E/N, V082A, P084D, A096Q, N097E/H, G104A/D/H/N/V/Y, N115H, N116E, F128G, P129H, S131D/E, R135A/E/F/H/I/K/L/M/S/T/V/W/Y, Y139E, T141E, S142D/E, R143E, D144E, V147C, I148L, N154D, S156A/C/D/N/T, G157C/D/E, S158C/L/Q/T/Y, V159L, R164A/K/M/Q/Y, A166D/E, N167E, M169L, T174V, Q176A/C/D/E/N, N177C/D/E, N178D. R179A/C/E/F/G/H/I/K/M/Q/S/V/W/Y, R180K, N182C/D/E, T188C/D/E, G189C/D/E, V193A/M, N198D/E, R207K/L/N/Q/T, V209P, S210C/D/E/L/N/Y, M211E/K/L/Q, N212C/Q, V228L, Q230E, R231C/E/L/N/Q, Y232F, S234D/E/T/W/Y, N236D/T, T238A/D/E/M/V, Q239D/E/M/N, K245E, N246A/L, T247E/Q, T249C/D/E/L/Y, N250D, N253D/E/P, S254Y, S255A/C/D/E, Q256C/E/Y, F257C, S259D/E/M/N, V262L, N263D, T268C/D/E, and R269H/P/W.

The following variants showed improved cleaning performance index (PI value of ≥1.1) compared to parent enzyme Bgi02446-S039E on at least one PAS-38 assay and at least one crème brûlée assay: T009N, V011A, Q012A/M, A01SI/V, V016L/M, R019C/K/L/Q, G020D, S024A, G025A/D/N, G052D, P054A/L/M/V, T055A/D, L059A/M/N, N060S, A096Q, F128G, P129H, G157D, S158Q/T, V159L, N177D, R179A/K, N182D, R207L, S210E, M211E/Q, Y232F, and Q256Y.

The following variants showed improved stability (PI value of ≥1.1) compared to parent enzyme Bgi02446-S039E in Tris-EDTA buffer: T003V, V004T, I008V, T009A/E/G/H/K/N/Q/S/W/Y, R010Q, V0IIA, Q012A/C/G/M/N/T, A015F/H/M/P/Q/W, V016S, H017C/E/F/I/L/N/V/W/Y, N018A/D/E/L/M/Q, R019C/D/Y, G020C/D/M/N, S024A/E, G025C/D/N, V0261, R027K, S033T, S036A/C/I/L/M/Q/V, N042C/D/E/M/Q, R044C/E/F/G/H/I/K/L/N/Q/S/T/V/W/Y, A047I/Y, V050I, G052A/M/N/S/T/Y, P054N/V, T055C/D/E/N, A057E/H/M/N/Q/T, L059N, S076A/D/E/F/H/K/L/M/N/R/T/Y, V082A, P084D/F/H/Y, N085S, G095A/N, A096M, N097K, S101T, V102L/M, G104M/N/T/V/W, I105V, Q107M, A113V, T114V, N115Q, N116E/H, H118D/E/N, S131A/D/E/I/M/N/P/Q/T/V, L133M, R135A/H/I/K/L/M/S/T/V/W/Y, A136M, S142A/D/E/H/M/N/Q, R143E/H/M/N/Q, V147C, I148V, A150M, S156N/T, G157A/C/N, S158C/F/L/M/N/Q/T/V/W/Y, V159L, G160A/C/M/S/T, A166D/E/P/Q, A170G, Q176C/M, N177A/C/D/H/L/M/Q/W/Y, R179M/Q, R180K, N182A/C/E/G/H/I/K/L/P/Q/S/T/V/W/Y, T188A/C/D/E/I/L/M/N/Q/V/W/Y, G189D, I192C/M, V193M, Q200H/I/K/M/V/Y, V209P, S210E/F/P, M211K, N212S, T218C/S, V228L, Q230E, R231C/E/H/N/T, Y232F/H, S234D/M, N236D/G/S/T, T238A/D/E/M/V, Q239E/L/M/T, N242A, N246A/L/S, T249E/F/I/L/S/Y, N250D/S, N253D/E, S254P, S255C/D/E/F/I/M/V/W, Q256C/E/F/H/W/Y, A264T, A266L/M/N, and T268C.

The following variants showed improved performance index (PI value of ≥1.1) compared to parent enzyme Bgi02446-S039E in ADW cleaning on at least one PAS-38 assay or at least one crème brûlée assay and improved stability (PI value of ≥1.1) in Tris-EDTA buffer: T009A/E/H/K/N/W/Y, R010Q, V011A, Q012A/C/M/N, A015F/H/M/W, H017C/E/F/I/L/N/V/W, N018D/E/M, R019C/D/Y, G020C/D/M/N, S024A/E, G025C/D/N, R027K, S036A/C/L/Q/V, N042C/D/E, R044C/E/G/H/I/L/N/Q/S/T, G052A/M/N, P054V, T055C/D/E, A057E, L059N, S076D/E/K/L/N, V082A, P084D, G095N, N097K, V102L/M, G104N/V, NI16E, H118D, S131D/E/M/N/P, R135A/H/I/K/L/M/S/T/V/W/Y, A136M, S142D/E, R143E/N, V147C, S156N/T, G157A/C, S158C/L/Q/T/Y, V159L, G160M/S, A166D/E, A170G, Q176C, N177A/C/D/L/M/Y, R179M/Q, R180K, N182A/C/E/S/Y, T188C/D/E/M, G189D, V193M, V209P, S210E, M211K, T218S, V228L, Q230E, R231C/E/N, Y232F, S234D, N236D/T, T238A/D/E/M/V, Q239E/M, N246A/L, T249E/L/Y, N250D, N253D/E, S255C/D/E, Q256C/E/Y, and T268C.

The following variants showed improved performance index (PI value of ≥1.1) compared to parent enzyme Bgi02446-S039E in HDL or HDD cleaning on BMI stain and improved stability (PI value of ≥1.1) in Tris-EDTA buffer: T003V, I008V, T009Q/W, Q012A/C/G/M/N/T, A015M/Q, H017C/I/N/W, R019D/Y, S024A/E, G025N, N042D/E/M, R044E/G/I/N/T, G052T, P054N/V, TOSSE, A057M/Q, L059N, S076R, S131A/D/M/P/Q, R135H/I/S/T/V, S142N/Q, R143E/H/M/N/Q, V147C, G157A, S158C/N/Q/T/V, G160A, A166Q, Q176M, N177C/Q, N182E/P/Q/T, T188D/E/V, V193M, S210E, Y232F, S234D, N236D, T238A/D, N246S, and N250D.

The following variants with a negative charge change showed improved performance index (PI value of ≥1.1) compared to parent enzyme Bgi02446-S039E in at least one of the Crème Brûlée assays: T009C/E/Y, R010A/K/M/N/Q/W, Q012C/D/E, P014D, A015D/E/Y, H017C/E, N018C/D/E, R019A/C/D/E/F/H/I/K/L/N/Q/S/T/W/Y, G020C/D, S024E, G025C/D/E, R027K, S036C/E, N042C/D/E, R044C/E/G/H/I/L/N/Q/S/T, G052C/D, P054C, T055C/D/E, A057D/E, L059C/D/E, S076D/E, P084D, N097E, G104D/Y, N116B, S131D/E, R135A/E/F/H/I/K/L/M/S/T/V/W/Y, Y139E, T141E, S142D/E, R143E, V147C, N154D, S156C/D, G157C/D/E, S158C/Y, R164A/K/M/Q/Y, A166D/E, N167E, Q176C/D/E, N177C/D/E, N178D, R179A/C/E/F/G/H/I/K/M/Q/S/V/W/Y, R180K, N182C/D/E, T188C/D/E, G189C/D/E, N198D/E, R207K/L/N/Q/T, S210C/D/E/Y, M211E, N212C, Q230E, R231C/E/L/N/Q, S234D/E/Y, N236D, T238D/E, Q239D/E, K245E, T247E, T249C/D/E/

Y, N250D, N253D/E, S254Y, S255C/D/E, Q256C/E/Y, F257C, S259D/E, N263D, T268C/D/E, and R269H/P/W.

The following variants with a negative charge change showed improved performance index (PI value of ≥1.1) compared to parent enzyme Bgi02446-S039E in the HDL BMI assay: Q012C/D/E, P014D, H017C/I/N/W, R019A/D/F/H/I/L/Q/S/W/Y, S024E, N042D/E, R044E/G/I/N/T, T055E, L059D/E, N115E, S13ID, R135E/F/H/I/S/T/V, Y139E, T141E, R143E/H/M/N/Q/V, S156C, G157D/E, S158C, R164M/Q/Y, N167E, Q176D/E, N177C/E, R179I/S/V/W, N182D/E, T188D/E, N198D, R207K/N/T, S210D/E, M211E, R2311/S, S234D, N236D, T238D, T249D, N250D, and R269H.

The following variants with a positive charge change showed improved performance index (PI value of ≥1.1) compared to parent enzyme Bgi02446-S039E in the HDD BMI assay: Q012R, S076R, Y186F, Y232F/Q/R, E265M/N/Q, and A266R.

EXAMPLE 4

*B. gibsonii* Subtilisin Sites with Surface Charge Modification Benefits

The three-dimensional structure of the *B. gibsonii* variant subtilisin BSP-00801 (SEQ ID NO: 18 in patent application WO2016205755) was used to examine sites where beneficial substitutions were identified by the study described in this application. FIG. 1 illustrates the spatial positions of a subset of the beneficial sites listed in Table 4. The main chain fold of the *B. gibsonii* BSP-00801 subtilisin is schematically represented in light gray, the catalytic triad (residues Asp 32, His 62 and Ser 215, numbered according to SEQ ID NO: 1) is shown as gray spheres. The core of this subtilisin fold includes a seven-stranded paralled beta-sheet, with several alpha-helices packed against the sheet on either side of it. In particular, two neighboring parallel alpha helices are packed on one side of the sheet—the first of these two helices spans residues 103 to 114 and the second helix spans residues 131 through 143.

FIG. 1 highlights the following sites depicted as black sticks: 76, 84, 97, 104, 115, 116, 131, 135, 139, 141, 142, 143, 156, 157, 231, and 234 (numbered according to SEQ ID NO: 1). These sites are surface exposed, in loops or in one of the abovementioned helices, and are suitable for modifications altering enzyme surface properties, such as electrostatic charge and hydrophobicity, potentially leading to variants with improved cleaning performance. Moreover, multiple sites, namely 104, 115, 116, 131, 135, 139, 141, 142, 143 (numbered according to SEQ ID NO: 1), are located on the same side of the molecule, residing on, or immediately adjacent to, the two neighboring parallel alpha helices mentioned above.

Substitutions at these positions that introduce an overall negative net charge relative to the parent subtilisin (under the conditions such as pH in the application) exhibit improved cleaning performance, as shown in Table 4. At some positions, such as positions R135 and R143, the overall negative charge relative to the parent subtilisin is introduced by replacing a positively charged amino acid, while at other positions, the overall negative charge relative to the parent is introduced by a substitution with a negatively charged amino acid.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

We claim:

1. A subtilisin variant comprising an amino acid sequence having a glutamate (E) residue at position 39 and further comprising an amino acid substitution X211E/Q/R wherein the subtilisin variant has at least 85% sequence identity to SEQ ID NO: 1; and
    wherein the amino acid positions of the variant are numbered by correspondence with the amino acid sequence of SEQ ID NO: 1.

2. The subtilisin variant according to claim 1, wherein said variant
    (i) is isolated;
    (ii) has proteolytic activity; or
    (iii) comprises a combination of (i) to (ii).

3. The subtilisin variant claim 1, wherein said variant comprises an amino acid sequence with 86%, 87%, 88%, 89%, 90%, 91%, 92%, 93%, 94%, 95%, 96%, 97%, 98%, 99% or less than 100% amino acid sequence identity to the amino acid sequence of SEQ ID NO: 1.

4. The subtilisin variant of claim 1, wherein said variant has one or more improved property when compared to a parent or reference subtilisin; wherein the improved property is selected from improved cleaning performance in detergent, improved stability; and combinations thereof.

5. The subtilisin variant of claim 4, wherein the improved property is (i) improved cleaning performance in detergent, wherein said variant has a blood-milk-ink (BMI), crème brûlée and/or egg stain cleaning performance index (PI)≥1.1 compared to the subtilisin having the amino acid sequence of SEQ ID NO: 1; and/or
(ii) improved stability, wherein said variant has a stability PI≥1.1 compared to the subtilisin having the amino acid sequence of SEQ ID NO: 1.

6. An enzyme composition comprising one or more subtilisin variant according to claim 1.

7. The enzyme composition according to claim 6, wherein said enzyme composition is an enzyme granule.

8. The composition according to claim 6, further comprising (i) one or more other enzymes selected from acyl transferases, amylases, alpha-amylases, beta-amylases, alpha-galactosidases, arabinases, arabinosidases, aryl esterases, beta-galactosidases, beta-glucanases, carrageenases, catalases, chondroitinases, cutinases, endo-beta-mannanases, exo-beta-mannanases, esterases, exo-mannanases, galactanases, glucoamylases, hemicellulases, hyaluronidases, keratinases, laccases, lactases, ligninases, lipases, lipolytic enzymes, lipoxygenases, mannanases, metalloproteases, nucleases, oxidases, oxidoreductases, pectate lyases, pectin acetyl esterases, pectinases, pentosanases, perhydrolases, peroxidases, phenoloxidases, phosphatases, phospholipases, phytases, polyesterases, polygalacturonases, additional proteases, pullulanases, reductases, rhamnogalacturonases, cellulases, tannases, transglutaminases, xylan acetyl-esterases, xylanases, and xylosidases; (ii) one or more surfactants; (iii) one or more ions selected from calcium and zinc; (iv) one or more adjunct material; (v) one or more stabilizers; (vi) from about 0.001% to about 1.0 weight % of the subtilisin variant; (vii) one or more bleaching agents; and/or (viii) combinations thereof.

\* \* \* \* \*